United States Patent
Geu Flores et al.

(10) Patent No.: US 9,096,863 B2
(45) Date of Patent: Aug. 4, 2015

(54) BIOSYNTHETIC ENGINEERING OF GLUCOSINOLATES

(75) Inventors: Fernando Geu Flores, Cambridge (MA); Morten Thrane Nielsen, Copenhagen (DK); Michael Daigaard Mikkelsen, Copenhagen (DK); Barbara Ann Halkier, Copenhagen (DK); Morten Emil Møldrup, Copenhagen (DK)

(73) Assignee: University of Denmark, Copenhagen (DK)

( * ) Notice: Subject to any disclaimer, the term of this patent is extended or adjusted under 35 U.S.C. 154(b) by 270 days.

(21) Appl. No.: 12/919,929

(22) PCT Filed: Feb. 27, 2009

(86) PCT No.: PCT/IB2009/000500
§ 371 (c)(1),
(2), (4) Date: Aug. 27, 2010

(87) PCT Pub. No.: WO2009/106985
PCT Pub. Date: Sep. 3, 2009

(65) Prior Publication Data
US 2011/0016582 A1 Jan. 20, 2011

Related U.S. Application Data

(60) Provisional application No. 61/031,914, filed on Feb. 27, 2008.

(51) Int. Cl.
*C12N 15/82* (2006.01)
*C07K 14/415* (2006.01)

(52) U.S. Cl.
CPC .......... *C12N 15/8243* (2013.01); *C07K 14/415* (2013.01)

(58) Field of Classification Search
None
See application file for complete search history.

(56) References Cited

PUBLICATIONS

Naur et al, 2003, Plant Phys.,133:63-72.*
Grubb et al, 2006, Trends in Plant Sci., 11:89-100.*
Kliebenstein et al, 2001, Plant Phys., 126:811-825.*
Kristensen et al, 2005, PNAS, 102:1779-1784.*
Naur et al, 2003, Plant Phys., 133:63-72.*
Hansen et al, 2001, J. Biol. Chem., 276:11078-11085.*
Piotrowski et al, 2004, J. Biol. Chem., 279:50717-50725.*
Kopriva, 2006, Ann. Of Botany, 97:479-495.*
Mikkelsen et al, 2004, Plant J., 37:770-777.*
Mikkelesen et al, 2003, Plant Physiol. 131:773-779.*
Kroymann et al, 2001, Plant Physiol., 127:1077-1088.*
Schuster et al, 2006, The Plant Cell, 18:2664-2679.*
Textor et al, 2007, Plant Physiol., 144:60-71.*
Nozawa et al, 2005, Biosci. Biotech. Biochem., 69:806-810.*
Zhang et al, 2006, Plant Cell, 18:1524-1536.*
Hansen et al, 2007, Plant J., 50:902-910).*
Hansen et al., CYP83B1 is the Oxime-metabolzing Enzyme in the Glucosinolate Pathway in *Arabidopsis*, The Journal of Biological Chemistry, 2001, 276(27), pp. 24790-24796.
Mikkelsen et al., Microbial production of indolyiglucosinolate through engineering of a multi-gene pathway in a versatile yeast expression platform, Metabolic Engineering, 2012, 14, pp. 104-111.
Zang et al., "Metabolic Engineering of Aliphatic Glucosinolates in Chinese Cabbage Plants Expressing *Arabidopsis* MAM1, CYP79F1, and CYP83A1", BMB Reports, Jun. 30, 2008, vol. 41, No. 6, pp. 472-478.
Mikkelsen et al., "Metabolic Engineering of Valine- and Isoleucine-Derived Glucosinolates in *Arabidopsis* Expressing CYP7902. from Cassava", Plant Physiology, vol. 131, No. 2, Feb. 2003, pp. 773-779.
Chen et al., "Update on Glucosinolate Metabolism and Transport", Plant Physiology and Biochemistry, vol. 39, No. 9, Sep. 1, 2001, pp. 743-758.
Nafisi et al., "Cytochromes P450 in the Biosynthesis of Glucosinolates and Indole Alkaloids", Phytochemistry Reviews, vol. No. 5, No. 2-3, Oct. 28, 2006, pp. 331-346.
Geu-Flores et al., Towards Engineering Glucosinolates Into Non-Cruciferous Plants, Planta, vol. 229, No. 2, Jan. 2009, pp. 261-270.
Geu-Flores et al., "Glucosinolate Engineering Indentifies Gamma-Glutamyl Peptidase", Nature Chemical Biology, vol. 5, No. 8, Aug. 2009, pp. 575-577.

* cited by examiner

*Primary Examiner* — Ashwin Mehta
*Assistant Examiner* — Jason Deveau Rosen
(74) *Attorney, Agent, or Firm* — Kilpatrick Townsend & Stockton LLP

(57) ABSTRACT

The invention provides methods and materials, such as newly characterized genes, and novel processes, for converting a host from a phenotype whereby the host is unable to carry out glucosinolate (GSL) biosynthesis or chain elongation from an amino acid GSL-precursor to a phenotype whereby the host carries out said biosynthesis or elongation.

18 Claims, 15 Drawing Sheets

Figure 1:
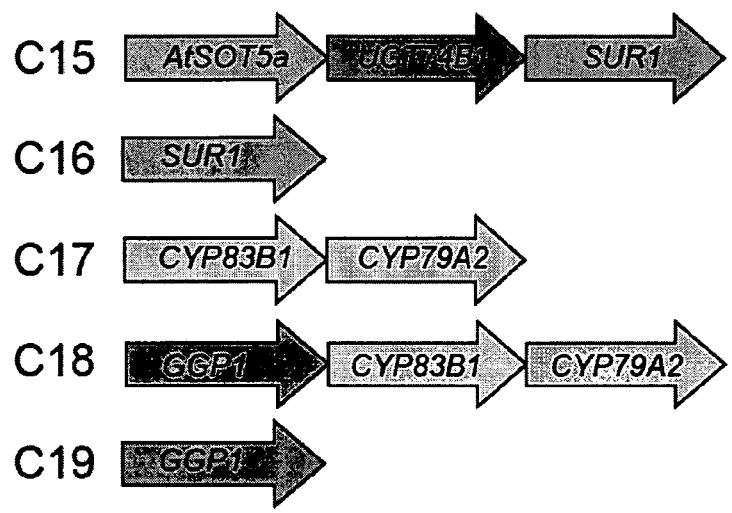

|  | At4g30530 | At4g30540 | At4g30550 | At2g23960 | At2g23970 |
|---|---|---|---|---|---|
| At4g30530 |  | 61 | 68 | 72 | 68 |
| At4g30540 | 61.8 |  | 63 | 58 | 64 |
| At4g30550 | 66.5 | 61.7 |  | 64 | 76 |
| At2g23960 | 71.8 | 56.3 | 62 |  | 64 |
| At2g23970 | 67.7 | 63.7 | 74.8 | 62.3 |  |

BIOSYNTHETIC ENGINEERING OF GLUCOSINOLATES

CROSS REFERENCE TO RELATED APPLICATIONS

This application is the U.S. National Phase of PCT/IB2009/000500 filed on Feb. 27, 2009 which claims the benefit of U.S. Application No. 61/031,094 filed on Feb. 27, 2008, both of which are incorporated herein by reference.

TECHNICAL FIELD

The present invention relates generally to genes and polypeptides which have utility in reconstituting or modifying glucosinolate (GSL) production or hydrolysis in host cells. The invention further relates to systems, methods and products employing the same.

BACKGROUND ART

Biosynthesis of GSLs

Glucosinolates are amino acid-derived secondary metabolites present in the Brassicales order, including the agriculturally important cruciferous vegetables, e.g. broccoli, and oilseed rape.

The molecule consists of a 'GSL skeleton' and a variable side chain derived from an amino acid. In the majority of Capparalean families, GSLs have phenolic side chains derived from phenylalanine (PHE) and branched aliphatic side chains, derived from valine and leucine. However, the predominant GSLs in the Brassicaceae possess side chains derived from chain elongated forms of methionine (MET) and PHE. Lower amounts of GSLs with indolylic side chains derived from tryptophan (TRP) also occur. The MET derived ('aliphatic') GSLs exhibit considerable variation in the length and structure of the side chain.

The biosynthesis of aliphatic GSLs can be considered in three parts:

Firstly, the development of chain elongation homologues of MET.

Secondly the synthesis of the GSL skeleton. This is called 'core biosynthesis', and includes at least five different enzymatic steps. The enzymes involved include two cytochromes P450 enzymes from the CYP79 and CYP83 families, which respectively catalyze the conversion of precursor amino acids to the corresponding oximes, followed by oxidation of the oximes to reactive compounds. In a sulfur donation step, which may be either non-enzymatic or involve a glutathione-5-transferase-type of protein, S-alkyl thiohydroximates are formed. The last three enzymatic steps include a C—S lyase, which converts S-alkylthiohydroxamates to thiohydroxamates, a glucosyltransferase, which glucosylates thiohydroxamates to yield desulfoglucosinolates, and a sulfotransferase, which adds a sulfate moiety to desulfoglucosinolates to produce GSLs. Each of the mentioned enzymatic steps is catalyzed by different enzymes of a gene family, with the possible exception of the C—S lyase step, which may have functional homologues although only the SUR1 gene has been characterized (see e.g. Mikkelsen et al (2004) Plant J.; Mikkelsen M D, Naur P, and Halkier B A (2004) 37, 770-777)

Thirdly side chain modifications.

Figure 10:
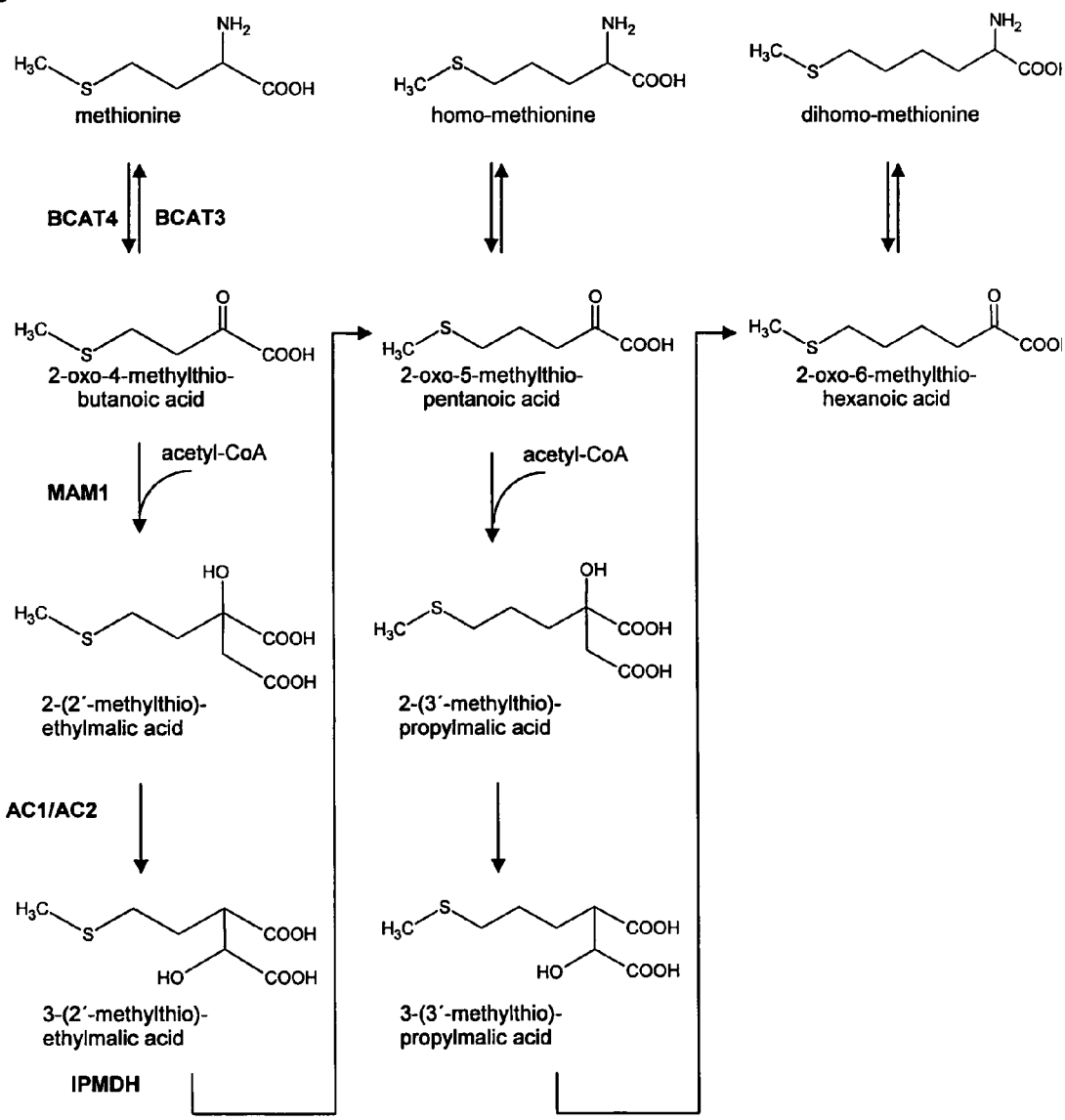

Taking the glucosinolate 4-methyl-sulfinyl-butyl glucosinolate (4-MSB) as an example, 4-MSB is derived from dihomomethionine (DHM), which is produced from MET through chain-elongation mechanisms similar to those of the branched-chain amino acid biosynthesis (FIG. 10). This procedure requires five distinct activities, of which three (MAM1, BCAT4 and BCAT3) have been characterized (Schuster et al., 2006; Kroymann et al., 2001: Knill et al., 2007). Secondly, DHM is then converted to 4-methylthiobutyl glucosinolate (4-MTB). This requires a minimum of five distinct activities, which have been characterized previously (FIG. 11; Hansen et al., 2001; Bak and Feyereisen, 2001; Mikkelsen et al., 2004; Piotrowski et al., 2004). Finally, 4-MTB is converted to 4-MSB through one of several flavin-containing monooxygenases (Hansen et al., 2007; prior filed unpublished PCT/IB2007/002588).

As an example of a glucosinolate that does not undergo aminoacid chain elongation or secondary modifications in its biosynthesis, benzylglucosinolate (BGSL) is directly synthesized from PHE via the core structure pathway.

GSLs and their Economic and Biological Importance

Aliphatic GSLs in cruciferous crops are of economic and biological importance, largely as a result of hydrolytic products released upon tissue disruption. GSLs and their breakdown products are often collectively referred to as 'mustard oils'. GSLs are degraded by endogenous myrosinases, or by microbial organisms in the gut. Isothiocyanates derived from methylsulfinylalkyl GSLs via the activity of myrosinases are associated with protection from carcinogens (Zhang et al. (1992). Proc. Natl. Acad. Sci. USA 89, 2399-2403). In particular, 4-methylsulphinylbutyl isothiocyanate (sulphoraphane), derived from the corresponding GSL 4-MSB (glucoraphanin), has previously been found to be a potent inducer of "phase 2" detoxifying enzymes, which have a role in detoxification of exogenous compounds (Zhang et al. (1992) The Plant Cell 18: 1524-1536; Juge et al., 2007). The corresponding heptyl- and octyl-GSLs have also been found to hold cancer preventive properties—for example 7-methylthioheptyl glucosinolate (7-MSH) and 8-methylthiooctyl glucosinolate (8-MSO) are potent cancer-preventive agents (Rose et al (2000). Carcinogenesis 21, 1983-1988).

Furthermore, sulphoraphane has been found to have an effect on bacteria that cause ulcers and stomach cancer (Fahey et al. (2002) PNAS 99, 7610-7615).

Moreover, many aliphatic GSLs have been implicated in mediating plant-herbivore interactions (Giamoustaris A & Mithen, R. F. (1995) Ann Appl Biol. 126, 347-363).

Additionally, GSLs and plants containing them have a role in biofumigation, wherein (for example) hydrolysis of glucosinolates in *Brassica* green manure or rotation crops leads to the release of biocidal compounds into the soil and the suppression of soil-borne pests and pathogens (J. A. Kirkegaard and M. Sawar, Plant and Soil, 201, 71-89, 1998).

Although glucosinolate-derived isothiocyanates have been known for decades as antibacterial compounds, interest in their use as therapeutic agents has become evident following identification of several human pathogens as effective targets, among them *Escherichia coli, Staphylococcus aureus*, and more recently *Helicobacter pylori*. Since isothiocyanates are unstable compounds, production of glucosinolates as their stable precursors is an attractive alternative to their direct production. Glucosinolates can be purified from natural sources, but their purification is complicated by the fact that different glucosinolates generally co-occur in a single plant tissue.

Unfortunately commercially important GSLs are found in only relatively small number of commonly grown species— for example 4-MSB has been found in a limited number of species in only five families of the Brassicales order. Other potentially interesting GSLs are also not widespread.

Thus it can be seen that the characterisation of activities involved in the GSL biosynthetic or metabolic pathways would provide a contribution to the art, as would the ability to modify the nature of amount of GSLs produced by organisms, or produce GSLs in novel hosts in which they do not naturally occur.

A paper published after the presently claimed priority date (Geu-Flores et al. "Towards engineering glucosinolates into non-cruciferous plants" Planta (2009) 229:261-270) reports the transfer of the last three steps of the benzylglucosinolate pathway (comprising the C—S lyase, glycosyltransferase and sulfotransferase) from *Arabidopsis* to tobacco.

SUMMARY OF THE INVENTION

The present inventors have successfully engineered the entire GSL biosynthetic pathway into heterologous organisms which are not otherwise GSL producers. This is the first description of heterologous production of glucosinolates achieved by co-expression of biosynthetic genes.

As part of the invention the inventors have reconstituted amino acid chain elongation in *Nicotiana benthamiana* (the first step, above), to produce DHM.

They have further reconstituted biosynthesis of short chain-elongated MET-derived glucosinolates (the second step, above), to produce 4-MTB. This has been in vivo coupled to the DHM biosynthesis. The production of long chain GSLs has also been demonstrated.

They have also coupled glucosinolate biosynthesis to secondary modifying enzymes. This has been demonstrated with a flavin-containing monooxygenase that oxidizes methyl-thio-alkyl glucosinolates to methyl-sulfinyl-alkyl glucosinolates, thereby converting 4-MTB to 4-MSB.

Additionally, they have also demonstrated synthesis of phenolic GSLs (benzylglucosinolate, BGSLs) and indole-based GSLs in *N. benthamiana*.

Furthermore, the present inventors have identified genes in *Arabidopsis thaliana* coding for polypeptides affecting GSL biosynthesis. For example they have newly characterised a gamma-glutamyl peptidase ($\gamma$-GP, termed herein GGP1) which has been shown to boost glucosinolate production several-fold. In vivo and in vitro activities of the recombinant enzyme are disclosed herein.

The present inventors have demonstrated the invention by co-infiltration of as many as ten different *Agrobacterium tumefaciens* strains into *N. benthamiana* at the same time, which is an approach not previously demonstrated in the literature, but which unexpectedly led to expression of the relevant genes in concert. More than one type of GSL has been simultaneously generated.

The methods and materials described herein can be used, inter alia, to produce recombinant host organisms (for example plants or microorganisms) which can produce GSLs even though they are not naturally produced by the wild-type host.

The methods and materials described herein can be used, inter alia, to generate stable crop-plants that accumulate specific glucosinolates and where appropriate, GSL degradation products. This may assist in integrated pest management and reduce chemical input in the form of pesticides, which is as an important step towards attaining a sustainable agriculture.

Engineering specific glucosinolates into edible crops according to the present invention could also help reduce the general incidence of certain types of cancer. Following human consumption, glucosinolates are converted to isothiocyanates by the gut microflora.

De novo engineering of glucosinolates according to the present invention can produce plants or microorganisms containing high amounts of a single glucosinolate, as well as glucosinolate mixtures, to be used as food additives or as cheap sources of therapeutic isothiocyanates.

DETAILED DESCRIPTION OF THE INVENTION

Reconstitution of Biosynthetic Pathways

As shown in the Examples below for the first time, the biosynthetic pathway leading to chain-elongated amino acids (such as DHM) and GSLs (such as 4-MSB and BGSLs) can be unexpectedly transferred to host species which do not naturally produce these compounds.

Amino Acid Chain Elongation

Thus in one aspect of the invention there is provided a method of converting a host from a phenotype whereby the host is unable to carry out chain elongation of an amino acid which is a GSL precursor to a phenotype whereby the host is able to carry out said chain elongation, which method comprises the step expressing a heterologous nucleic acid within the host or one or more cells thereof, following an earlier step of introducing the nucleic acid into the host or an ancestor of either, wherein the heterologous nucleic acid comprises a plurality of nucleotide sequences each of which encodes a polypeptide which in combination have amino acid chain elongation activity.

In another aspect of the invention there is provided a host cell transformed with a heterologous nucleic acid which comprises a plurality of nucleotide sequences each of which encodes a polypeptide which in combination have amino acid chain elongation activity, wherein expression of said nucleic acid imparts on the transformed host the ability to carry out chain elongation of the amino acid which is a GSL precursor.

The nucleotides may be on the same or different heterologous nucleic acid constructs. Methods of transforming appropriate hosts are described in more detail below.

In any embodiments described herein, one or more of the nucleic acids or sequences may include a targetting sequence to a sub-cellular compartment e.g. be targeted to the chloroplast in a plant. For expression in organism without chloroplasts, the target sequence may be removed prior to expression.

It will be understood that in any embodiment of the present invention referring to a specific gene or polypeptide, including in respect of a biosynthetic activity such as chain elongation or GSL biosynthesis, substantially homologous variants of the specific sequences may likewise be used provided that they provide the relevant biological activity. For example any of the enzymes or genes listed in Table 2 may be replaced by substantially homologous variants having the same or similar activity.

Likewise the activities may be replaced by variants or homologues with similar activities which differ in respect of substrate specificity, to thereby alter the nature of products generated—for example Cyp79A2 may be replaced with Cyp79B2 and so on.

Figure 12:
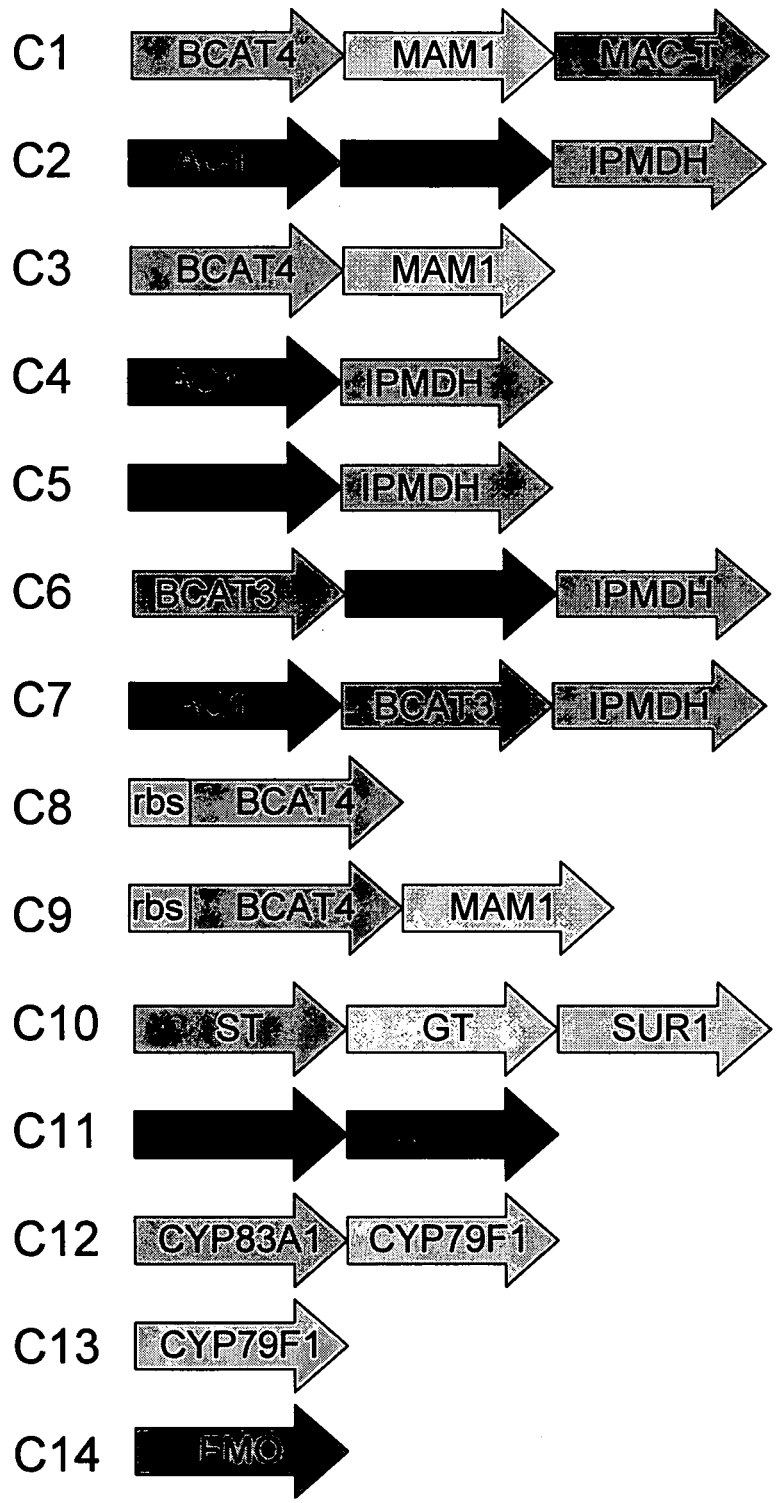

Some of the constructs and genes used by the inventors in support and exemplification of this aspect of the invention are shown in FIG. 12.

As described in the Examples below, a minimum of two genes (a transaminase such as BCAT4 and a condensation enzyme such as MAM1) was sufficient for DHM biosynthesis. However as described below a redundancy of genes in DHM biosynthesis lead to much higher levels For DHM-biosynthesis, transformed plant-hosts such as *N. benthamiana* are clearly capable of supporting certain reactions such as those catalyzed by the aconitases, the IPMDH and possibly that of BCAT3. However, these activities are much less effective in DHM-biosynthesis than those of the *Arabidopsis* genes used in the Examples herein, which are shown to generate approximately 1000-fold more DHM.

As most of the chain-elongating enzymes are localized in the chloroplast, it is believed that compartmentalization could in principle be important. Specifically, targeting BCAT4 to the chloroplast by adding the rubisco small subunit chloroplast targeting signal to the BCAT4 N-terminus did not by itself increase DHM production. As shown in the Examples, and referring to FIG. 12, the most efficient combination for DHM production was C1+C2+C9, with a DHM to 2o6 ratio of approximately 35. Interestingly, C1+C3+C6 produced a comparable total level of DHM and 2o6, but with a ratio of less than 0.5. This suggests that there may be a spatial separation of the transaminase and 2o6.

In one embodiment of the present invention the chain elongated amino acid is an n-homo-methionine, more preferably DHM.

Preferably the nucleic acid encodes at least a transamination enzyme (e.g. BCAT4) and a condensation enzyme (MAM1 or MAM3).

In one embodiment the nucleic acid encodes: BCAT4 and MAM1 or MAM3.

In one embodiment the nucleic acid encodes: BCAT4, MAM1 or MAM3, AC1 or AC2, IPMDH, and MAC-T In one embodiment the nucleic acid encodes: BCAT4, MAM1 or MAM3, AC1, AC2, IPMDH, and MAC-T In one embodiment the host is non-plant and nucleic acid encoding BCAT3 also used.

In one embodiment the BCAT4 is targeted to the chloroplast.

MAM1 is preferred for biosynthesis of short chain-elongated MET derivatives as described above.

However MAM3 is a homologue of MAM1 that has been shown to catalyze the same reaction, but leading to formation of chain-elongated METs up to hexahomomethionine (Textor et al., 2007). Therefore, by using MAM3 in an analogous way, long-chain elongated METs may be produced. These may be converted to the corresponding glucosinolates in the manner exemplified for 4-MTB and 3-MTP production below without further changes (see Examples 2 and 8).

It will be understood that whereas MAM3 from *Arabidopsis* has a preference for producing penta- and hexa-homomethionine, other MAM3 genes from other species may be used to produce e.g. predominantly tri- and quatro-homomethionine or even longer chain METs, e.g. nona-homomethionine as the corresponding sulphinyl-glucosinolate has been described (Fahey et al., 2001).

Thus in one embodiment the n-homo-methionine is penta- or hexa-homomethionine. In this case the nucleic acid may encode MAM3 from *A. thaliana* instead of MAM1 in the embodiments described above.

In another embodiment the n-homo-methionine is tri- or quatro-homomethionine, or nona-homomethionine. In this case the nucleic acid may encode MAM3 from other *Brassica* species instead of MAM1 in the embodiments described above.

In addition to aliphatic amino acids, it is known that aromatic amino acids can also be chain elongated to generate aromatic GSLs.

Thus, for example, phenylethyl glucosinolate is produced from a chain-elongated phenylalanine precursor. It will this be understood that this glucosinolate may be produced in a manner analogous to the chain-elongation of MET.

Thus in one embodiment the chain elongated amino acid is homo-phenylalanine.

Aliphatic GSL Biosynthesis

In addition to demonstrating that chain elongation could be conferred on a 'non-native' host, the present inventors further demonstrated that a minimum of five additional genes was sufficient for 4-MSB biosynthesis (CYP79F1, CYP83A1, SUR1, GT, ST). However use of an additional two genes for 4-MSB biosynthesis (GGP1, GSTF11) lead to much higher product levels. GGP1 is discussed in more detail hereinafter.

CYP79F1 is able to metabolize most chain-extended METs. CYP79F2 has been shown to be specific for penta- and hexa-homomethionine (Chen et al., 2003). Therefore, when using MAM3 to produce long-chain METs, substituting CYP79F1 with CYP79F2 would most likely produce less of the short-chain MET-derived glucosinolates, and more of the long-chain MET-derived glucosinolates.

Thus in one aspect of the invention there is provided a method of converting a host from a phenotype whereby the host is unable to carry out GSL biosynthesis from a chain elongated amino acid precursor to a phenotype whereby the host is able to carry out said GSL biosynthesis, which method comprises the step expressing a heterologous nucleic acid within the host or one or more cells thereof, following an earlier step of introducing the nucleic acid into the host or an ancestor of either, wherein the heterologous nucleic acid comprises a plurality of nucleotide sequences each of which encodes a polypeptide which in combination have said GSL biosynthesis activity, In another aspect of the invention there is provided a host cell transformed with a heterologous nucleic acid which comprises a plurality of nucleotide sequences each of which encodes a polypeptide which in combination have said GSL biosynthesis activity, wherein expression of said nucleic acid imparts on the transformed host the ability to carry out GSL biosynthesis from a chain elongated amino acid precursor.

In one embodiment the GSL is an aliphatic GSL, for example a short chain-elongated MET-derived glucosinolate such as 3-MTP or 4-MTB.

In this embodiment the nucleic acid may encode: CYP83A1, CYP79F1, ST; GT and SUR1.

In this embodiment the nucleic acid may also encode: GGP (e.g. GGP1) and\or GST (e.g. GSTF11).

In embodiments where the aliphatic GSL is a medium chain-elongated MET-derived glucosinolates (e.g. penta- and hexa-homomethionine) and CYP79F2 may be used instead of CYP79F1.

In embodiments where the aliphatic GSL is a valine- and isoleucine-derived glucosinolate CYP79D2 or CYP79D1 may be used instead of CYP79F1.

Other nucleic acids appropriate to the production of longer aliphatic GSLs such as 7-MSH or 8-MSO may be selected by those skilled in the art in the light of the present disclosure.

Aromatic GSL Biosynthesis

In the light of the disclosure herein, production of homophenylalanine-derived phenylethyl-glucosinolate may be achieved by substitution of homologous genes with the ones specific for homophenylalanine, and by introduction of the chain elongation genes specific for the conversion of PHE to homophenylalanine.

Thus in one embodiment the GSL may be aromatic, such as phenylethyl-glucosinolate.

As described in the Examples below, benzylglucosinolate (BGSL) have been produced in *N. benthamiana* using constructs carrying CYP79A2, CYP83B1 and SUR1.

For aromatic GSLs other than BGSLs, CYP79A2 may be replaced with CYP79B2 or B3 (for indole GSL) or CYP79A1 (for tyrosine-derived p-hydroxybenzyl GSL (pOHBGSL)).

In Examples below indole-3-yl-methyl glucosinolate (I3G) is prepared in a non-native host at high concentration using CYP79B2.

BGSL production was significantly increased when UGT74B1 and AtST5a were also expressed.

BGSL production was significantly increased (7× fold) when At4g30530 (termed herein 'GGP1') was also expressed. Indeed BGSL production is also possible with the combination CYP79A2, CYP83B1 and GGP1 alone.

Other Genes Effecting GSL Synthesis

As noted above, a final step in the GSL core pathway requires a sulfotransferase, which adds a sulfate moiety to desulfoglucosinolates to produce GSLs. The co-factor required for this step is PAPS (adenosine 3'-phosphate 5'-phosphosulfate).

PAPS is biosynthesized from ATP (adenosine-5'-triphosphate) and inorganic sulphate ($SO_4^{2-}$) in two enzymatic steps. First, ATP sulfurylase (ATPS) sulfates ATP to form APS (adenosine 5'-phosphosulfate). Second, APS kinase (APK) phosphorylates APS to form PAPS. The phosphate donor for this reaction is another molecule of ATP (Kopriva 2006).

Figure 19:
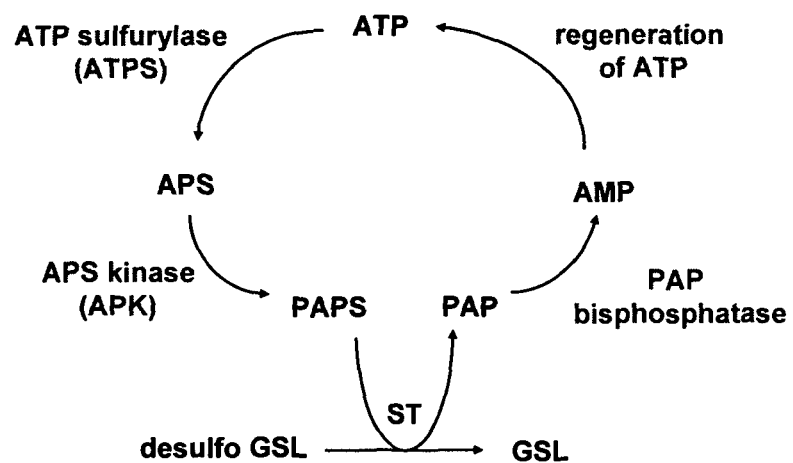

After sulfation, the by-product PAP (adenosine 3',5'-bisphosphate) can be hydrolysed to AMP (adenosine-5'-monohosphate) by a PAP bisphosphatase. This reaction is biologically important not only because it removes PAP, which is an inhibitor of sulfotransferase reactions (Klein et al, 2006), but also because AMP can be regenerated to form ATP, leading to only one ATP consumed per cycle of sulfation (FIG. 19).

Since PAPS is found in all known organisms, in certain embodiments of the invention (where the native PAPS flux is sufficient for the required sulfotransferase activity) there will be no requirement to introduce genes involved in PAPS biosynthesis and regeneration genes.

Nevertheless these genes may be preferred where it is believed that desulfoglucosinolates (or derivatives thereof) would otherwise occur.

In such embodiments of the invention, in addition to the other genes described herein, it may be preferable to introduce additional genes involved in PAPS biosynthesis and/or regeneration. In the plant *Arabidopsis thaliana*, these genes can be identified making use of publicly available co-expression databases (see example 11). The genes identified in this way (e.g. APK1 or APK2, coding for APK enzymes, or SAL1, coding for a PAP bisphosphatase) code for proteins predicted to have chloroplast transit peptides. Therefore, the co-expression of a PAPS/PAP antiporter can also be benefitial for the heterologous production of GSLs plants. Accordingy, and in general, in the relevant aspects of the invention concerning production of GSLs, nucleic acids encoding one or more or all of: an ATPS enzyme; an APK enzyme; a PAP bisphosphatase; a PAPS/PAP antiporter, may be utilised.

As an alternative to a PAPS/PAP antiporter, the chloroplast targeting peptide of these genes can be removed. It will likewise be appreciated by those skilled in the art that proteins performing similar functions from other organisms in which PAPS biosynthesis occurs in the cytosol or nucleus, like the nematode *Urechis caupo*, in which the ATPS and APK proteins are fused in a single bi-functional protein (Rosenthal and Leustek, 1995), can be used. These approaches may be particularly preferred when engineering GSLs in microorganisms.

Genes Effecting Secondary Modifications to Core GSLs

Several secondary modifications of the core-glucosinolate structure occur in nature, thereby yielding many different glucosinolates with different biological activities from a single precursor glucosinolate.

For example flavin-containing monooxygenases are described in Hansen et al., 2007 and prior filed unpublished PCT/IB2007/002588 which oxidize 3-MTP and 4-MTB to 3-MSP and 4-MSB, respectively. Specifically, these two FMOs from *A. thaliana* (encoded by At1g62560 (SEQ ID NO: 94) and At1g65860 (SEQ ID NO: 95)) have been characterised by the inventors as catalyzing this reaction. Additionally, At1g62570 (SEQ ID NO: 96) and At1g62540 (SEQ ID NO: 97) are part of a sub-cluster with At1g62560 (SEQ ID NO: 94) and At1g65860 (SEQ ID NO: 95), and are therefore believed to also catalyse the production of sulphinylalkyl GSLs.

Although one or more endogenous *N. benthamiana* activities are able to convert 4-MTB to 4-MSB, addition of the FMO At1g65860 (SEQ ID NO: 95) lead to complete conversion of 4-MTB to 4-MSB. The above mentioned FMOs are believed to likewise support this reaction.

As demonstrated herein, this activity can also conveniently be transferred to hosts not normally synthesizing the core GSLs. Thus it will be understood by those skilled in the art that further different glucosinolates with distinct biological activities could be produced, by use of nucleic acid encoding FMOs, and\or additional or alternative GSL modifying enzymes.

Thus the AOP2 gene has been shown to convert 3-MSP and 4-MSB to 2-propenyl-glucosinolate (sinigrin) and 3-butenyl-glucosinolate, respectively (Kliebenstein et al., 2001). Therefore it will be appreciated in the light of the present disclosure, that with addition of the AOP2 gene, and without any further modifications of the procedure, 3-MSP and 4-MSB (and longer methyl-sulfinyl-alkyl GSLs) may be converted in the host to 2-propenyl-glucosinolate and 3-butenyl-glucosinolate (and longer alkenyl GSLs), respectively.

The AOP3 gene has been shown to convert 3-MSP to 3-hydroxypropyl-glucosinolate (Kliebenstein et al., 2001). Therefore it will be appreciated n the light of the present disclosure, that with addition of the AOP3 gene, and without any further modifications of the procedure, 3-MSP, 4-MSB and longer methyl sulfinyl-alkyl glucosinolates may be converted in the host to their hydroxy-counterparts, e.g. 4-MSB would be converted to 4-hydroxybutyl-glucosinolate.

The alkenyl-glucosinolates produced from sulfinylalkyl-glucosinolates by AOP2 may be further hydroxylated by the unidentified activity commonly referred to as GS-OH (Kliebenstein et al., 2001), producing hydroxyl-alkenyl glucosinolates. Thus in the light of the present disclosure hydroxyl-alkenyl glucosinolates may be generated by addition of AOP2 and the GS-OH activity to the other modifications provided herein.

The hydroxy-glucosinolates (hydroxyl-alkyl and hydroxy-alkenyl) can be further modified by addition of a benzoyloxy group. This may be achieved by use of a previously describe Co-A benzoyl-ligase BZO1 (At1g65880, Kliebenstein et al., 2007) and appropriate Co-A benzoyl conjugating enzyme.

Thus in the light of the present disclosure it can be seen that adding these two activities (AOP2 and the GS-OH) to the described procedure may result in production of benzoyloxy-alkenyl glucosinolates. Similarly, adding BZO1, the Co-A benzoyl conjugating activity and AOP3 to the described procedure can be expected to result in production of benzoyloxy-alkyl glucosinolates.

Other glucosinolate-modifying activities, like methoxylation of indole glucosinolate, may also be co-expressed with the relevant core biosynthesis genes to produce new glucosinolates.

Hydrolysis of GSLs

Upon tissue damage, e.g. by wounding by herbivores or pathogens, glucosinolates are hydrolyzed by myrosinases to produce a series of bioactive compounds, which includes primarily isothiocyanates and nitriles.

The factors 'ESP' and 'ESM', which respectively favours and modify epithionitrile formation, are discussed by Zhang et al. (2006) The Plant Cell 18: 1524-1536 and Matusheski et al. (2006) J Agric Food Chem 54: 2069-2076.

In the light of the present disclosure it can be seen that adding activities involved in degradation of the glucosinolates (where that is desirable) may also be achieved—for example myrosinase may be preferred in heterologous hosts intended to function as bio-fumigants, or where the glucosinolates are produced to increase resistance to microbial pathogens and/or herbivores.

Other Genes Affecting Chain Elongations and/or GSL Synthesis

It will be understood by those skilled in the art, in the light of the present disclosure, that additional genes may included over and above those demonstrated above, to provide additional activities and\or improve expression or activity. These include those expressing co-factor or helper proteins, or other factors.

For example, highly related, transcription factors of the MYB-type from *A. thaliana* (encoded by At5g61420, At5g07690, and At5g07700) have been shown to be regulators of aliphatic GSLs, and are described in prior filed unpublished PCT/IB2007/002588. Where metabolic engineering according to the present invention is being carried out in plant hosts, it may be preferred to express these also, especially if the genes in question are used with their endogenous promoters to facilitate a more physiologically natural level of expression.

Certain Preferred Embodiments

In one embodiment the following genes are introduced into a host:
BCAT4, MAM1, AC1, AC2, IPMDH, MAC-T, cBCAT4, CYP79F1, CYP83A1, GSTF11, SUR1, GGP1, UGT74C1, AtST5b and FMO.

In another embodiment the following genes are introduced into a host:
BCAT4, MAM3, AC1, AC2, IPMDH, MAC-T, cBCAT4, CYP79F1, CYP83A1, GSTF11, SUR1, GGP1, UGT74C1, AtST5b and $FMO_{GS-OX5}$ In another embodiment the following genes are introduced into a host:
CYP79B2, CYP83B1, GSTF9, SUR1, GGP1, UGT74B1, AtST5a.

DEFINITIONS AND PRACTICE OF THE PRESENT INVENTION

Some aspects of the invention as it relates to heterologous reconstitution of the biosynthetic pathways discussed above will now be discussed in more detail.

The term "heterologous" is used broadly in this aspect to indicate that the gene/sequence of nucleotides in question (e.g. encoding GSL-biosynthesis modifying polypeptides) have been introduced into said cells of the host or an ancestor thereof, using genetic engineering, i.e. by human intervention. Nucleic acid heterologous to a host cell will be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

"Transformed" in this context means that the nucleotide sequences of the heterologous nucleic acid alter one or more of the cell's characteristics and hence phenotype e.g. with respect to GSL biosynthesis. Such transformation may be transient or stable.

Thus a host may be converted to the phenotypes described above by transforming it with heterologous nucleic acid as described above by introducing the nucleic acid into the host cell via a vector and causing or allowing recombination between the vector and the host cell genome to introduce a nucleic acid according to the present invention into the genome.

As one aspect of the invention there is disclosed a method employing the co-infiltration of a plurality of *Agrobacterium tumefaciens* strains each carrying one or more of the heterologous nucleic acids discussed above for concerted expression thereof in a biosynthetic pathway discussed above e.g. where at least 5, 6, 7, 8, 9 or 10 different *Agrobacterium tumefaciens* strains are co-infiltrated e.g. each carrying a gene of Table 2 or homolog thereof.

The invention further encompasses a host cell transformed with nucleic acid or a vector as described above (e.g. comprising the GSL-biosynthesis modifying nucleotide sequences) especially a plant or a microbial cell. In the transgenic host cell (i.e. transgenic for the nucleic acid in question) the transgene may be on an extra-genomic vector or incorporated, preferably stably, into the genome. There may be more than one heterologous nucleotide sequence per haploid genome.

Generally speaking, following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

Plants which include a plant cell according to the invention are also provided.

In addition to the regenerated plant, the present invention embraces all of the following: a clone of such a plant, seed, selfed or hybrid progeny and descendants (e.g. F1 and F2 descendants). The invention also provides a plant propagule from such plants, that is any part which may be used in reproduction or propagation, sexual or asexual, including cuttings, seed and so on. It also provides any part of these plants, which in all cases include the plant cell or heterologous GSL-biosynthesis modifying DNA described above.

Other preferred hosts include microorganisms such as *Escherichia coli*, *Saccharomyces cerevisiae* or *Aspergillus nidulans*.

As an alternative to microorganisms, cell suspension cultures of GSL-producing plant species, including also the moss *Physcomitrella patens* may be cultured in fermentation tanks. Overexpression of regulators of the metabolon (e.g. MYB factors) can activate the metabolon in this undifferentiated state (see for example Grotewold et al. (Engineering Secondary Metabolites in Maize Cells by Ectopic Expression of Transcription Factors, Plant Cell, 10, 721-740, 1998) which discloses the production of high amounts of deoxyflavonoids in undifferentiated maize cell suspension culture by overexpression of one or two transcription factors).

The methods of the present invention will generally include the use of the newly characterised nucleic acids of the invention (defined below) optionally in conjunction with the manipulation of other genes affecting GSL biosynthesis known in the art.

The methods described above may be used to generate a chain elongated amino acid which is a GSL precursor and\or a GSL and\or a GSL hydrolysis product in a heterologous host.

The methods used herein may be used, for example, to increase levels of GSL in the host for improved nutraceutical potential, or increasing biofumigative activity or potential, or for the purposes of purification. Thus the present invention includes a method of altering any one or more of these characteristics in a host comprising use of a method as described herein.

The GSL precursor and\or a GSL and\or a GSL hydrolysis product will be non-naturally occurring in the species into which they are introduced.

GSLs from the plants of the plants or methods of the invention may be isolated and commercially exploited.

Thus the methods above will usually form a part of, possibly one step in, a method of producing a GSL or GSL hydrolysis product in a host. The method may comprise the steps of culturing the host (where it is a microorganism) or growing the host (where it is a plant) and then harvesting it and purifying the product therefrom. The product thus produced forms a further aspect of the present invention. The utility of GSLs or GSL hydrolysis products is described above. Uses may include as pharmaceuticals or nutriceuticals (e.g. in respect of protection from carcinogens or imparting other cancer or ulcer protective properties); use in mediating plant-herbivore interactions; use in other anti-bacterial agents, and so on.

Newly Characterized Genes of the Invention

Figure 4:
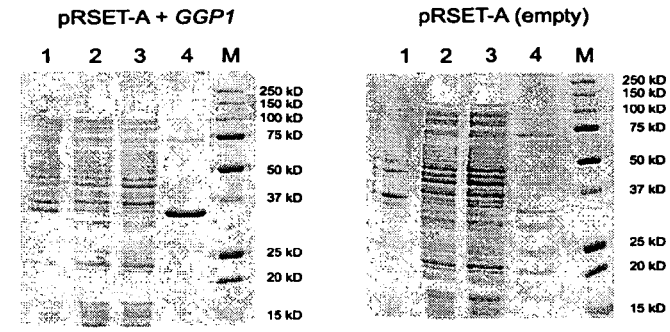
Figure 4:
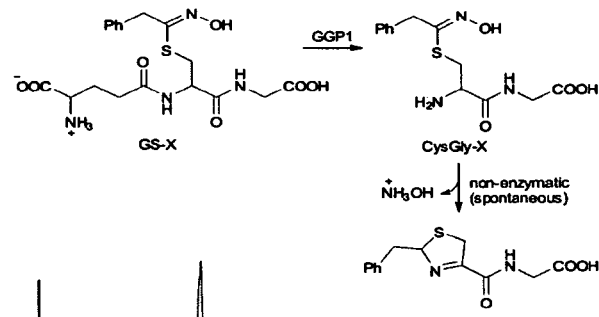
Figure 4:
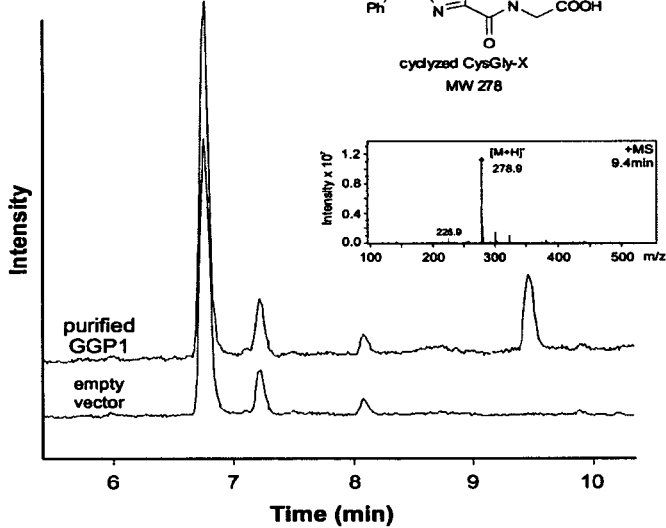
Figure 4:
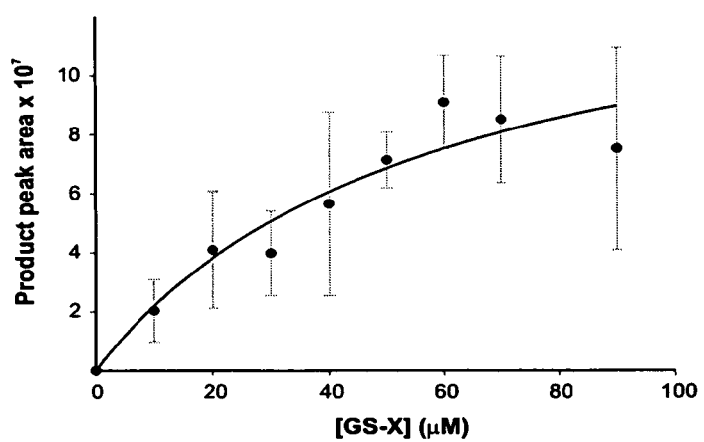

As noted above, in support of the present invention, the inventors have further identified genes in *Arabidopsis* coding for polypeptides which affect GSL biosynthesis. For example they have shown that the protein encoded by At4g30530 (GGP1 protein) is able to cleave of gamma-glutamyl peptide bonds. In particular recombinant GGP1 has been shown to cleave the gamma-glutamyl residue of a synthetic glutathione-conjugate (S-(phenylacetohydroxymoyl)-L-glutathione; GS-X; FIG. 4) and gamma-glutamyl-p-nitroanilide (GPNA; see FIG. 5).

As noted above it can also boost glucosinolate production several-fold when expressed alongside other heterologous genes in a host organism.

Additionally the inventors have established that phylogenetically this gene is closely related to other genes from *Arabidopsis*, including At4g30540, At2g23960, At2g23970, and At4g30550. The GGP1 gene also appears to have close relatives in other plant species, specially in those containing glucosinolates, like for example, the gene AAK50344 from *Brassica carinata*.

TABLE 1a genes in the newly characterized GGP family of the invention

| Name\biological activity | AGI identifier | Abbreviation used herein | SEQ ID (cDNA) | SEQ ID (protein) |
|---|---|---|---|---|
| GGP1-γ-glutamyl peptidase | At4g30530 | γGP | 1 | 2 |
| γGP homologue | At4g30550 | | 3 | 4 |
| γGP homologue | At2g23960 | | 5 | 6 |
| γGP homologue | At2g23970 | | 7 | 8 |
| γGP homologue | At4g30540 | | 9 | 10 |
| γGP homologue | AAK50344 | | 11 | 12 |

Thus the deduced amino acid sequences of these accessions (GGP polypeptides) are set out as SEQ ID NOs: 2, 4, 6, 8, 10 and 12. Thus in one aspect of the invention, there is disclosed isolated nucleic acid encoding any of these polypeptides. The cDNA sequences of these accessions are set out as SEQ ID NOs: 1, 3, 5, 7 9, 11. Other nucleic acids of the invention include those which are degeneratively equivalent to these.

Figure 2:
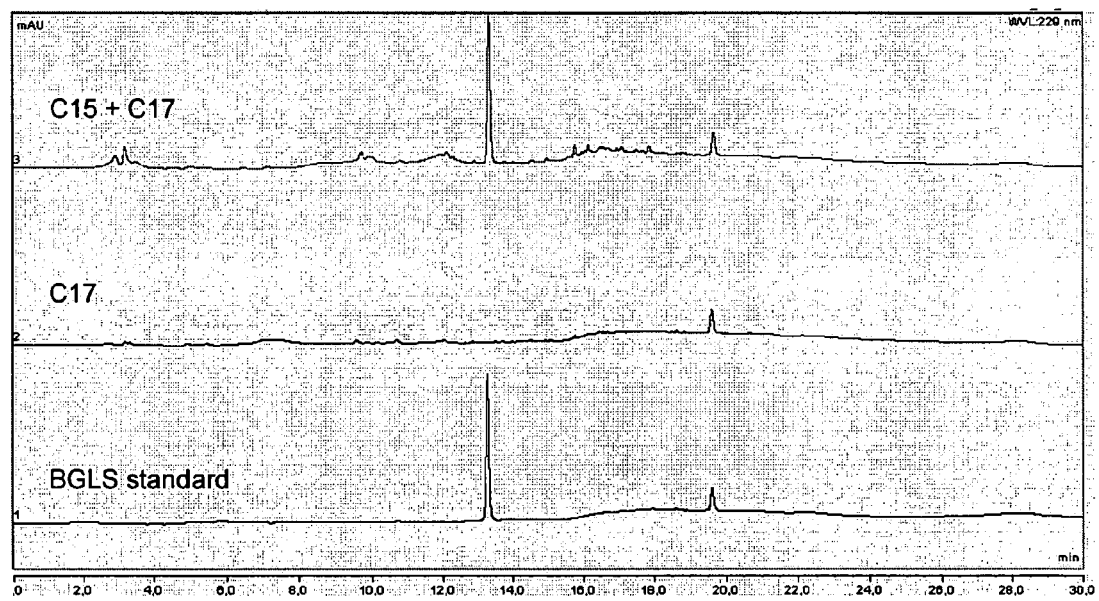

A phylogenetic tree is shown in FIG. 2. In terms of the relationship between the encoded proteins using BLASTp, the minimal identity is 58%. Thus a preferred mutual identity within the group of GGPs of the present invention is at least 60%. Variants of the GGP sequences of the invention are discussed in more detail hereinafter.

In all aspects of the present invention, preferred GGP sequences are those corresponding to GGP1 and At4g30550.

GGP polypeptides have the biological activity of GGP i.e. the ability to cleave gamma-glutamyl peptide bonds. This can be demonstrated, for example, by use of a synthetic glutathione-conjugate e.g. GS-X or GPNA. Specifically, an assay may be performed as in the materials and methods described below, optionally by measurement of cyclized Cys-Gly conjugate using LC-MS (for cleavage of GS-X) or p-nitroanilide (PNA) using UV-VIS spectroscopy (for cleavage of GPNA). GGP variants may preferably have one of these activities (or at least 50, 60, 70, 80, 90, 95, 96, 97, 98, 99% of this activity) of SEQ ID NO: 2. The GGP genes described herein and variants thereof form aspects of the present invention, as described below.

Nucleic acid according to the present invention may include cDNA, RNA, genomic DNA and modified nucleic acids or nucleic acid analogs (e.g. peptide nucleic acid). Where a DNA sequence is specified, e.g. with reference to a figure, unless context requires otherwise the RNA equivalent, with U substituted for T where it occurs, is encompassed. Nucleic acid molecules according to the present invention may be provided isolated and/or purified from their natural environment, in substantially pure or homogeneous form, or free or substantially free of other nucleic acids of the species of origin, and double or single stranded. Where used herein, the term "isolated" encompasses all of these possibilities. The nucleic acid molecules may be wholly or partially synthetic. In particular they may be recombinant in that nucleic acid sequences which are not found together in nature (do not run contiguously) have been ligated or otherwise combined artificially. Nucleic acids may comprise, consist, or consist essentially of, any of the sequences discussed hereinafter.

Aspects of the invention further embrace isolated nucleic acid comprising a sequence which is complementary to any of those discussed hereinafter.

Other Newly Characterized Penes of the Invention

Other aspects of the invention relate to the following newly characterized genes:

TABLE 1b other newly characterized genes of the invention

| Name\biological activity | AGI identifier | Abbreviation used herein | SEQ ID (cDNA) | SEQ ID (protein) |
|---|---|---|---|---|
| Aconitase (isomerisation) | At2g43100 | AC1 | 13 | 14 |
| Aconitase (isomerisation) | At3g58990 | AC2 | 15 | 16 |
| Isopropylmalate dehydrogenase (oxidative decarboxylation) | At1g31180 | IPMDH | 17 | 18 |
| methylthioalkyl alfa-ketoacid chloroplastidic transporter (MAC transporter) | At4g12030 | MAC-T | 19 | 20 |
| Glutathione-S-transferase 11 | At3g03190 | GSTF11 | 21 | 22 |

Figure 11:
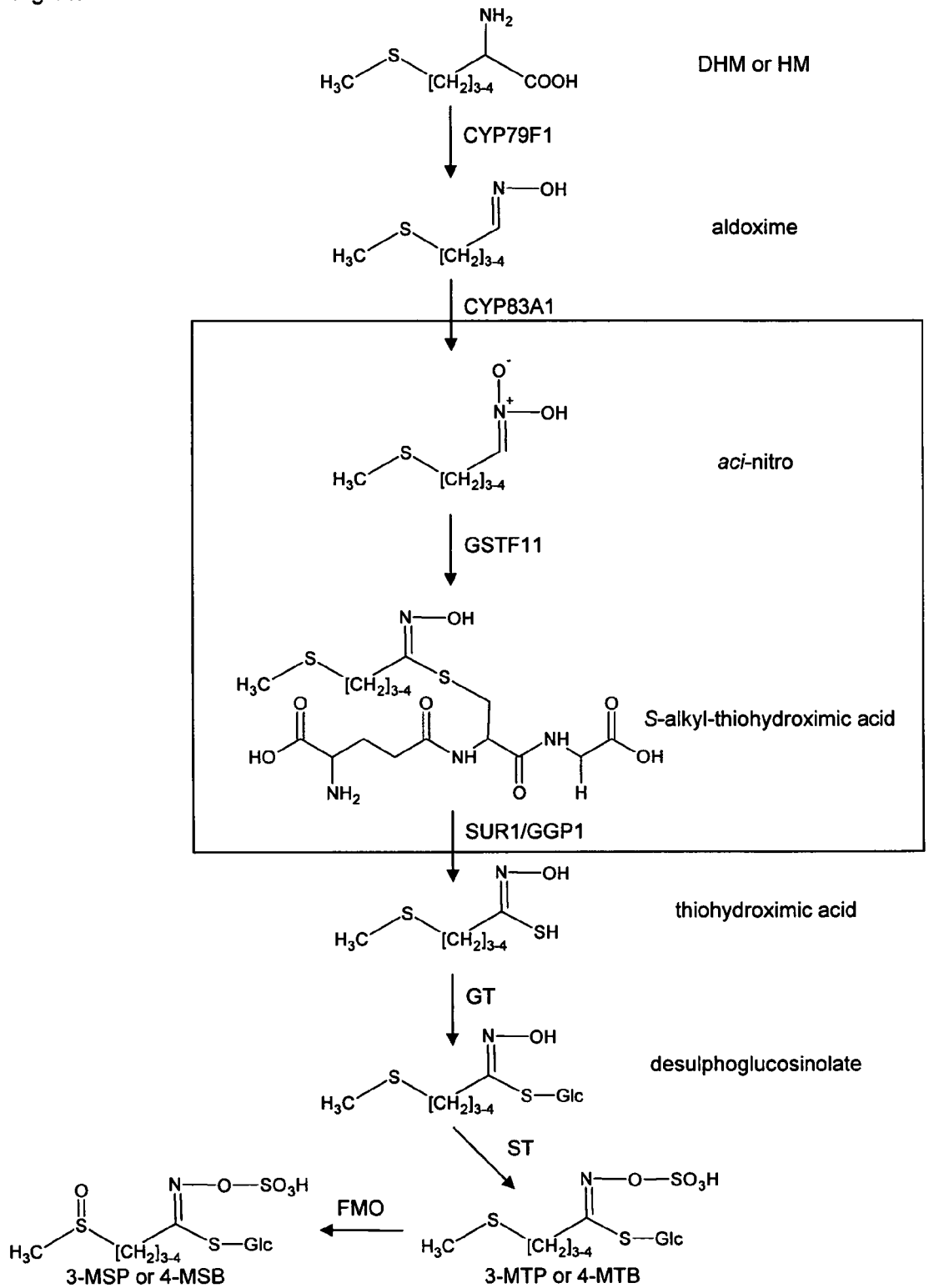

The relevant biological activities may be assayed based on the reactions shown in FIG. 11.

Alternatively they can be assayed by activity in vivo as described in the Examples i.e. by introduction of a plurality of heterologous constructs to generate GSLs or intermediates, which can be assayed by LC-MS or the like.

For example the biological activities of AC1, AC2, IPMDH and MAC-T can be assayed as per Example 1, by comparing constructs which differ in the relevant activity, and measuring products (e.g. DHM) or intermediates (such as 204, 205, 206).

The above newly characterised GSL-modifying genes and variants thereof form aspects of the present invention, as described below.

Thus in one aspect of the invention, there is disclosed isolated nucleic acid encoding any of these polypeptides (14, 16, 18, 20 or 22). Preferably this may have the sequence of 13, 15, 17, 19 or 21. Other nucleic acids of the invention include those which are degeneratively equivalent to these.

For brevity, collectively the sequences encoding the GGP and other activities described above may be described herein as "GSL genes of the invention" or the like. Likewise the encoded polypeptides are termed "GSL polypeptides of the invention". It will be appreciated that where this term is used generally, it also applies to any of these sequences individually.

In a further aspect of the present invention there are disclosed nucleic acids which are variants of the GSL genes of the invention discussed above.

A variant nucleic acid molecule shares homology with, or is identical to, all or part of the GSL genes or polypeptides of the invention discussed above.

They further share the relevant biological activity of the GSL genes of the invention as described above.

Such variants, as with the specific sequences discussed herein, may be used to alter the GSL content of a plant, as assessed by the methods disclosed herein. For instance a variant nucleic acid may include a sequence encoding a functional polypeptide (e.g. which may be a variant of any of SEQ ID Nos 2, 4, 6, 8, 10, 12, 14, 16, 18, 20, or 22 above and which may cross-react with an antibody raised to said polypeptide). Alternatively they may include a sequence which interferes with the expression or activity of such a polypeptide (e.g. sense or anti-sense suppression of a GSL-gene of the invention).

Variants may also be used to isolate or amplify nucleic acids which have these properties.

Generally speaking variants may be:

(i) Novel, naturally occurring, nucleic acids, isolatable using the sequences of the present invention. They may include alleles (which will include polymorphisms or mutations at one or more bases) or pseudoalleles (which may occur at closely linked loci to the GSL genes of the invention). Also included are paralogues, isogenes, or other homologous genes belonging to the same families as the GSL genes of the invention. Also included are orthologues or homologues from other plant species.

Thus, included within the scope of the present invention are nucleic acid molecules which encode amino acid sequences which are homologues of GSL genes of the invention of *Arabidopsis thaliana*. Homology may be at the nucleotide sequence and/or amino acid sequence level, as discussed below. A homologue from a species other than *A. thaliana* encodes a product which causes a phenotype similar to that caused by the *A. thaliana* GSL genes of the invention. In addition, mutants, derivatives or alleles of these genes may have altered, e.g. increased or decreased, enzymatic activity or substrate specificity compared with wild-type.

(ii) Artificial nucleic acids, which can be prepared by the skilled person in the light of the present disclosure. Such derivatives may be prepared, for instance, by site directed or random mutagenesis, or by direct synthesis. Preferably the variant nucleic acid is generated either directly or indirectly (e.g. via one or more amplification or replication steps) from an original nucleic acid having all or part of the sequence of a GSL gene of the invention.

Also included are nucleic acids corresponding to those above, but which have been extended at the 3' or 5' terminus.

The term 'variant' nucleic acid as used herein encompasses all of these possibilities. When used in the context of polypeptides or proteins it indicates the encoded expression product of the variant nucleic acid.

Some of the aspects of the present invention relating to variants will now be discussed in more detail.

Sequence identity may be assessed as using BLASTp (proteins) or Megablast (nucleic acids) from NCBI using default settings, as used in the Examples.

Variants of the sequences disclosed herein preferably share at least 55%, 56%, 57%, 58%, 59%, 60%, 65%, or 70%, or 80% identity, most preferably at least about 90%, 95%, 96%, 97%, 98% or 99% identity. Such variants may be referred to herein as "substantially homologous".

In a further aspect of the invention there is disclosed a method of producing a derivative nucleic acid comprising the step of modifying any of the GSL genes of the present invention disclosed above.

Changes may be desirable for a number of reasons. For instance they may introduce or remove restriction endonuclease sites or alter codon usage.

Alternatively changes to a sequence may produce a derivative by way of one or more (e.g. several) of addition, insertion, deletion or substitution of one or more nucleotides in the nucleic acid, leading to the addition, insertion, deletion or substitution of one or more (e.g. several) amino acids in the encoded polypeptide.

Such changes may modify sites which are required for post translation modification such as cleavage sites in the encoded polypeptide; motifs in the encoded polypeptide for phosphorylation etc. Leader or other targeting sequences (e.g. membrane or golgi locating sequences) may be added to the expressed protein to determine its location following expression if it is desired to isolate it from a microbial system.

Other desirable mutations may be random or site directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation. Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. altered stability or specificity.

Nucleic acid fragments may have utility in probing for, or amplifying, the sequence provided or closely related ones. Suitable lengths of fragment, and conditions, for such processes are discussed in more detail below.

The fragments may encode particular functional parts of the polypeptide (i.e. encoding a biological activity of it). Thus the present invention provides for the production and use of fragments of the full-length GSL polypeptides of the invention disclosed herein, especially active portions thereof. An "active portion" of a polypeptide means a peptide which is less than said full length polypeptide, but which retains its essential biological activity.

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

Particular regions, or domains, or active portions of GSL genes or polypeptides of the invention may have utility in their own right as follows, if they share the biological activity of the parent protein. For example an active portion of an GGP-polypeptide of the present invention retains the ability to catalyse the cleavage of gamma-glutamyl peptide bonds.

The provision of sequence information for the GSL genes of the invention of *A. thaliana* enables the obtention of homologous sequences from other plant species. In particular, homologues may be easily isolated from *Brassica* spp (e.g. *Brassica nigra, Brassica napus, Brassica oleraceae, Brassica rapa, Brassica carinata, Brassica juncea*) as well as even remotely related cruciferous species. GSLs are also found in the genus *Drypetes*.

Thus a further aspect of the present invention provides a method of identifying and cloning i.e. genes which encode GSL-biosynthesis modifying polypeptides from plant species other than *A. thaliana* which method employs a GSL gene of the present invention. As discussed above, sequences derived from these may themselves be used in identifying and in cloning other sequences. The nucleotide sequence information provided herein, or any part thereof, may be used in a data-base search to find homologous sequences, expression products of which can be tested for ability to influence a plant characteristic. Alternatively, nucleic acid libraries may be screened using techniques well known to those skilled in the art and homologous sequences thereby identified then tested.

The present invention also extends to nucleic acid encoding an GSL-modifying polypeptide-encoding homologue obtained using all or part of a nucleotide sequence shown as SEQ ID Nos 1, 3, 5, 7, 9, 11, 13, 15, 17, 19, and 21 (or the corresponding genomic sequences of the relevant accessions). These encoded products will share a biological activity with the respective polypeptides described above (SEQ ID Nos 2, 4, 6, 8, 10, 12, 14, 16, 18, 20 and 22.)

In another embodiment the nucleotide sequence information provided herein may be used to design probes and primers for probing or amplification. An oligonucleotide for use in probing or PCR may be about 30 or fewer nucleotides in length (e.g. 18, 21 or 24). Generally specific primers are upwards of 14 nucleotides in length. For optimum specificity and cost effectiveness, primers of 16-24 nucleotides in length may be preferred. Those skilled in the art are well versed in the design of primers for use in processes such as PCR. If required, probing can be done with entire restriction fragments of the gene disclosed herein which may be 100's or even 1000's of nucleotides in length. Small variations may be introduced into the sequence to produce 'consensus' or 'degenerate' primers if required.

Such probes and primers form one aspect of the present invention.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the single stranded DNA fragments on the filter and binding determined. DNA for probing may be prepared from RNA preparations from cells. Probing may optionally be done by means of so-called 'nucleic acid chips' (see Marshall & Hodgson (1998) Nature Biotechnology 16: 27-31, for a review).

In one embodiment, a variant encoding a GSL-biosynthesis modifying polypeptide in accordance with the present invention is obtainable by means of a method which includes:
(a) providing a preparation of nucleic acid, e.g. from plant cells. Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as are described hereinafter,
(b) providing a nucleic acid molecule which is a probe or primer as discussed above,
(c) contacting nucleic acid in said preparation with said nucleic acid molecule under conditions for hybridisation of said nucleic acid molecule to any said gene or homologue in said preparation, and, (d) identifying said gene or homologue if present by its hybridisation with said nucleic acid molecule. Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

Preliminary experiments may be performed by hybridising under low stringency conditions. For probing, preferred conditions are those which are stringent enough for there to be a simple pattern with a small number of hybridizations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989):

$T_m$=81.5° C.+16.6 Log [Na+]+0.41 (% G+C)−0.63 (% formamide)−600/#bp in duplex

As an illustration of the above formula, using [Na+]=[0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80-90% identical, hybridization overnight at 42° C. in 0.25M $Na_2HPO_4$, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M $Na_2HPO_4$, pH 7.2, 6.5% SDS, 10% dextran sulfate and a final wash at 60° C. in 0.1×SSC, 0.1% SDS.

Thus this aspect of the present invention includes a nucleic acid including or consisting essentially of a nucleotide sequence of complementary to a nucleotide sequence hybridisable with any encoding sequence provided herein. Another way of looking at this would be for nucleic acid according to this aspect to be hybridisable with a nucleotide sequence complementary to any encoding sequence provided herein.

In a further embodiment, hybridization of a nucleic acid molecule to a variant may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of a GSL gene of the present invention are employed. Using RACE PCR, only one such primer may be needed (see "PCR protocols; A Guide to Methods and Applications", Eds. Innis et al, Academic Press, New York, (1990)).

Thus a method involving use of PCR in obtaining nucleic acid according to the present invention may include:
(a) providing a preparation of plant nucleic acid, e.g. from a seed or other appropriate tissue or organ,
(b) providing a pair of nucleic acid molecule primers useful in (i.e. suitable for) PCR, at least one of said primers being a primer according to the present invention as discussed above,
(c) contacting nucleic acid in said preparation with said primers under conditions for performance of PCR,
(d) performing PCR and determining the presence or absence of an amplified PCR product.

The presence of an amplified PCR product may indicate identification of a variant.

In all cases above, if need be, clones or fragments identified in the search can be extended. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence.

If a putative naturally occurring homologous sequence is identified, its role in GSL biosynthesis can be confirmed, for instance by methods analogous to those used in the Examples below, or by generating mutants of the gene (e.g. by screening the available insertional-mutant collections) and analyzing the GSL content of the plants. Alternatively the role can be inferred from mapping appropriate mutants to see if the homologue lies at or close to an appropriate locus.

In a further embodiment, antibodies raised to a GSL polypeptide or peptide of the invention can be used in the identification and/or isolation of variant polypeptides, and then their encoding genes. Thus, the present invention provides a method of identifying or isolating a GSL-biosynthesis modifying polypeptide, comprising screening candidate polypeptides with a polypeptide comprising the antigen-binding domain of an antibody (for example whole antibody or a fragment thereof) which is able to bind a GSL polypeptide of the invention, or preferably has binding specificity for such a polypeptide. Methods of obtaining antibodies are described hereinafter.

Candidate polypeptides for screening may for instance be the products of an expression library created using nucleic acid derived from a plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid.

As used hereinafter, unless the context demands otherwise, the term "GSL-biosynthesis modifying nucleic acid" is intended to cover any of the GSL-genes of the present invention and variants thereof described above, particularly those variants encoding polypeptides sharing the biological activity of a GSL-polypeptide of the invention. The term "GSL-biosynthesis modifying polypeptide" should be interpreted accordingly.

In each case the preferred GSL-biosynthesis modifying nucleic acid are SEQ ID Nos 1, 3, 5, 7, 9, 11, 13, 15, 17, 19 and 21. The preferred GSL-biosynthesis modifying polypeptide are SEQ ID Nos 2, 4, 6, 8, 10, 12, 14, 16, 18, 20 and 22.

The present invention provides for inter alia reduction or increase in GSL quality or quantity in plants. This allows for production of better seed quality (e.g. in *Brassica napus*), increase of cancer preventive GSL's in cruciferous salads such as e.g. *Eruca sativa*, enhancement of herbivore and pathogen resistance in cruciferous crop plants, and increase of biofumigation potential.

As noted above, important dietary GSLs such as 4-MSB are only found in fairly low levels in many vegetables, including *Brassica* vegetables and other cruciferous salads (McNaughton et al. 2003, British Journal Of Nutrition 90(3): 687-697). It is therefore desirable to generate plants with a higher content of 4-MSB. Such plants can be used either directly in human consumption or they will be a good source for extraction of 4-MSB. Thus, for example, GSL-biosynthesis modifying nucleic acids may be transformed into plants such as *Brassica* vegetables and other cruciferous salads to increase the level of sulphoraphane present when the plants are consumed.

In different embodiments, the present invention provides means for manipulation of total levels of GSLs in plants such as oilseeds and horticultural crucifers through modification of GSL biosynthesis, e.g. by up or down regulating GSL-biosynthesis modifying nucleic acids.

In one aspect of the present invention, the GSL-biosynthesis modifying nucleic acid described above is in the form of a recombinant and preferably replicable vector.

"Vector" is defined to include, inter alia, any plasmid, cosmid, phage or *Agrobacterium* binary vector in double or single stranded linear or circular form which may or may not be self transmissible or mobilizable, and which can transform a prokaryotic or eukaryotic host either by integration into the cellular genome or exist extrachromosomally (e.g. autonomous replicating plasmid with an origin of replication).

Generally speaking, those skilled in the art are well able to construct vectors and design protocols for recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992.

Specifically included are shuttle vectors by which is meant a DNA vehicle capable, naturally or by design, of replication in two different host organisms, which may be selected from actinomycetes and related species, bacteria and eucaryotic (e.g. higher plant, mosses, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. yeast and bacterial, or plant cell. The vector may be a bi-functional expression vector which functions in multiple hosts. In the case of genomic DNA, this may contain its own promoter or other regulatory elements (optionally in combination with a heterologous enhancer, such as the 35S enhancer discussed in the Examples below). The advantage of using a native promoter is that this may avoid pleiotropic responses. In the case of cDNA this may be under the control of an appropriate promoter or other regulatory elements for expression in the host cell By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Thus nucleic acid according to the invention may be placed under the control of an externally inducible gene promoter to place expression under the control of the user. An advantage of introduction of a heterologous gene into a plant cell, particularly when the cell is comprised in a plant, is the ability to place expression of the gene under the control of a promoter of choice, in order to be able to influence gene expression, and therefore GSL biosynthesis, according to preference. Furthermore, mutants and derivatives of the wild-type gene, e.g. with higher or lower activity than wild-type, may be used in place of the endogenous gene.

Thus this aspect of the invention provides a gene construct, preferably a replicable vector, comprising a promoter (optionally inducible) operably linked to a nucleotide sequence provided by the present invention, such as the GSL-biosynthesis modifying gene.

Particularly of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148). Suitable vectors may include plant viral-derived vectors (see e.g. EP-A-194809).

Suitable promoters which operate in plants include the Cauliflower Mosaic Virus 35S (CaMV 35S). Other examples are disclosed at pg 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate). Positive selection system such as that described by Haldrup et al. 1998 Plant molecular Biology 37, 287-296, may be used to make constructs that do not rely on antibiotics.

The present invention also provides methods comprising introduction of such a construct into a plant cell or a microbial (e.g. bacterial, yeast or fungal) cell and/or induction of expression of a construct within a plant cell, by application of a suitable stimulus e.g. an effective exogenous inducer.

In a further aspect of the invention, there is disclosed a host cell containing a heterologous construct according to the present invention, especially a plant or a microbial cell.

The discussion of host cells above in relation to reconstitution of GSL biosynthesis in heterologous organisms applies mutatis mutandis here.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention (e.g. comprising the GSL-biosynthesis modifying nucleotide sequence) especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Plants which include a plant cell according to the invention are also provided.

In addition to plants in which it is desired to reconstitute GSL biosynthesis de novo as described above, preferred plant species of this aspect may be those in which it is preferred to modify GSL biosynthesis by introduction of a GSL-biosynthesis modifying nucleic acid of the invention e.g. where such biosynthesis occurs naturally e.g. Brassicales and Drypetes.

The most important crops for modification of meal quality are oilseed forms of *Brassica* spp. (e.g. *B. napus*, *B. rapa* (syn *B. campestris*), *B. juncea*, *B. carinata*).

For enhancement of flavour and cancer preventive properties the most important species are *B. oleracea* (including e.g. Broccoli and Cauliflower), horticultural forms of *B. napus* (e.g. swedes [=rutabaga, spp. napobrassica], oil seed rape] and *B. rapa* (including both turnips and chinese cabbage [=pakchois]), cruciferous salads (including e.g. *Eruca sativa* and *Diplotaxis tenuifolia*) and horticultural forms of *Raphanus* (e.g. Radish (*Raphanus sativa*)).

The plant background may preferably be one in which the breakdown of GSLs is directed (naturally, or by genetic manipulation) towards isothiocyanates to get e.g. sulforophane.

GSLs may also be modified in condiment mustard forms of Sinapis alba (white/yellow mustard), *B. juncea* (brown/Indian mustard) and *B. nigra* (black mustard). All of these species are targets for enhancement of pest and disease resistance via GSL modification. Modifications for enhanced disease and pest resistance includes modifications to leaf and root GSLs to enhance the biofumigation potential of crucifers when used as green manures and as break crops in cereal rotations.

The levels of GSLs in commercially grown broccoli are relatively low compared to those found in salad crops such as rocket (*Eruca Sativa* and *Diplotaxis tenuifolia*) which accumulates 4-MSB (Nitz et al 2002, Journal Of Applied Botany-Angewandte Botanik 76(3-4): 82-86; McNaughton et al. 2003, British Journal Of Nutrition 90(3): 687-697). Rocket is one particular preferred target.

Plant backgrounds such as those above may be natural or transgenic e.g. for one or more other genes relating to GSL biosynthesis.

For plants in which it is desired to down-regulate GSL-biosynthesis modifying genes (e.g. with antisense, amiRNA or hairpin silencing constructs—see below) the preferred backgrounds are those which have the GS-OH locus leading to pro-goitrin.

In addition to the regenerated plant, the present invention embraces all of the following: a clone of such a plant, seed, selfed or hybrid progeny and descendants (e.g. F1 and F2 descendants). The invention also provides a plant propagule from such plants, that is any part which may be used in reproduction or propagation, sexual or asexual, including cuttings, seed and so on. It also provides any part of these plants, which in all cases include the plant cell or heterologous GSL-biosynthesis modifying DNA described above.

The present invention also encompasses the expression product of any of the coding GSL-biosynthesis modifying nucleic acid sequences disclosed and methods of making the expression product by expression from encoding nucleic acid therefore under suitable conditions, which may be in suitable host cells.

Use of a recombinant GGP or other GSL-biosynthesis modifying polypeptide of the invention, or variant thereof, to catalyse its respective biological activity (as described in Table 1a or 1b above) forms another aspect of the invention.

In addition to use of the nucleic acids of the present invention for production of functional GSL-biosynthesis modifying polypeptides the information disclosed herein may also be used to reduce the activity of GSL-biosynthesis modifying activity in cells in which it is desired to do so.

This may be desirable, for instance, to prevent the accumulation of undesirable GSLs in plants (such as 2-hydroxy-3-butenyl glucosinolate (progoitrin) in rapeseed).

Down-regulation of expression of a target gene may be achieved using anti-sense technology.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of the gene silencing or co-suppression technology may be found in WO95/34668 (Biosource); Angell & Baulcombe (1997) The EMBO Journal 16, 12:3675-3684; and Voinnet & Baulcombe (1997) Nature 389: pg 553.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition.

It may be advantageous to include the initiating ATG codon, and perhaps one or more nucleotides upstream of the initiating codon. A further possibility is to target a conserved sequence of a gene, e.g. a sequence that is characteristic of one or more genes, such as a regulatory sequence.

The sequence employed may be about 500 nucleotides or less, possibly about 400 nucleotides, about 300 nucleotides, about 200 nucleotides, or about 100 nucleotides. It may be possible to use oligonucleotides of much shorter lengths, 14-23 nucleotides, although longer fragments, and generally even longer than about 500 nucleotides are preferable where possible, such as longer than about 600 nucleotides, than about 700 nucleotides, than about 800 nucleotides, than about 1000 nucleotides or more.

It may be preferable that there is complete sequence identity in the sequence used for down-regulation of expression of a target sequence, and the target sequence, although total complementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a variant of such a sequence in the terms described above. The sequence need not include an open reading frame or specify an RNA that would be translatable.

Further options for down regulation of gene expression include the use of ribozymes, e.g. hammerhead ribozymes, which can catalyse the site-specific cleavage of RNA, such as mRNA (see e.g. Jaeger (1997) "The new world of ribozymes" Curr Opin Struct Biol 7:324-335, or Gibson & Shillitoe (1997)"Ribozymes: their functions and strategies form their use" Mol Biotechnol 7: 242-251.)

Anti-sense or sense regulation may itself be regulated by employing an inducible promoter in an appropriate construct.

Double stranded RNA (dsRNA) has been found to be even more effective in gene silencing than both sense or antisense strands alone (Fire A. et al Nature, Vol 391, (1998)). dsRNA mediated silencing is gene specific and is often termed RNA interference (RNAi) (See also Fire (1999) Trends Genet. 15: 358-363, Sharp (2001) Genes Dev. 15: 485-490, Hammond et al. (2001) Nature Rev. Genes 2: 1110-1119 and Tuschl (2001) Chem. Biochem. 2: 239-245).

RNA interference is a two step process. First, dsRNA is cleaved within the cell to yield short interfering RNAs (siRNAs) of about 21-23 nt length with 5' terminal phosphate and 3' short overhangs (~2 nt) The siRNAs target the corresponding mRNA sequence specifically for destruction (Zamore P. D. Nature Structural Biology, 8, 9, 746-750, (2001)

Thus in one embodiment, the invention provides double stranded RNA comprising a sequence encoding part of a GSL polypeptide of the present invention or variant (homologue) thereof, which may for example be a "long" double stranded RNA (which will be processed to siRNA, e.g., as described above). These RNA products may be synthesised in vitro, e.g., by conventional chemical synthesis methods.

RNAi may be also be efficiently induced using chemically synthesized siRNA duplexes of the same structure with 3'-overhang ends (Zamore P D et al Cell, 101, 25-33, (2000)). Synthetic siRNA duplexes have been shown to specifically suppress expression of endogenous and heterologeous genes in a wide range of mammalian cell lines (Elbashir S M. et al. Nature, 411, 494-498, (2001)).

Thus siRNA duplexes containing between 20 and 25 bps, more preferably between 21 and 23 bps, of the GSL-genes of the present invention sequence form one aspect of the invention e.g. as produced synthetically, optionally in protected form to prevent degradation. Alternatively siRNA may be produced from a vector, in vitro (for recovery and use) or in viva Accordingly, the vector may comprise a nucleic acid sequence encoding a GSL-gene of the present invention (including a nucleic acid sequence encoding a variant or fragment thereof), suitable for introducing an siRNA into the cell in any of the ways known in the art, for example, as described in any of references cited herein, which references are specifically incorporated herein by reference.

In one embodiment, the vector may comprise a nucleic acid sequence according to the invention in both the sense and antisense orientation, such that when expressed as RNA the sense and antisense sections will associate to form a double stranded RNA. This may for example be a long double stranded RNA (e.g., more than 23 nts) which may be processed in the cell to produce siRNAs (see for example Myers (2003) Nature Biotechnology 21:324-328).

Alternatively, the double stranded RNA may directly encode the sequences which form the siRNA duplex, as described above. In another embodiment, the sense and antisense sequences are provided on different vectors.

Another methodology known in the art for down-regulation of target sequences is the use of "microRNA" (miRNA) e.g. as described by Schwab et al 2006, Plant Cell 18, 1121-1133. This technology employs artificial miRNAs, which may be encoded by stem loop precursors incorporating suitable oligonucleotide sequences, which sequences can be generated using well defined rules in the light of the disclosure herein. Thus, for example, in one aspect there is provided a nucleic acid encoding a stem loop structure including a sequence portion of one of the target GSL-genes of the invention of around 20-25 nucleotides, optionally including one or more mismatches such as to generate miRNAs (see e.g. the website of Weigel World). Such constructs may be used to generate transgenic plants using conventional techniques.

These vectors and RNA products may be useful for example to inhibit de novo production of the GSL polypeptides of the present invention in a cell. They may be used analogously to the expression vectors in the various embodiments of the invention discussed herein.

Thus the present invention further provides the use of any of the sequence above, for example: variant GSL-biosynthesis modifying nucleotide sequence, or its complement (e.g. in the context of any of the technologies discussed above); double stranded RNA with appropriate specificity as described above; a nucleic acid precursor of siRNA or miRNA as described above; for down-regulation of gene expression, particularly down-regulation of expression of the GSL-biosynthesis modifying gene or homologue thereof, preferably in order to modify GSL biosynthesis in a plant.

As shown in the Examples below, analysis of a double knockout in MYB28 and MYB29 identified an emergent property of the system since the very, very low level of aliphatic glucosinolates in these plants could not be predicted by the chemotype of the single knockouts. Thus the MYB regulatory genes disclosed herein appear to have evolved both overlapping and specific regulatory capacities, and appear to be the main regulators of aliphatic glucosinolates in *Arabidopsis*.

Thus double- or even triple-knockouts (or other down-regulated mutants) may be preferred in manipulating phenotypes, in the relevant aspects of the invention described herein.

The GSL-genes of the present invention and variants thereof may be used in combination with any other gene, such as transgenes involved in GSL biosynthesis or other phenotypic trait or desirable property. This is described in more detail above in relation to the aspects of the invention concerning reconstitution of biosynthesis. By use of a combination of genes, plants or microorganisms (e.g. bacteria, yeasts or fungi) can be tailored to enhance production of desirable precursors, or reduce amounts of undesirable metabolism.

Up- and down-regulation of the activity of GSL polypeptides of the present invention and variants thereof enables modifications to be made to meal quality of oilseeds crucifers, cancer preventive activity and flavour of horticultural crucifers, and/or resistance to herbivores and pathogens and biofumigative activity.

Methods of the invention may be used to produce non-naturally occurring chain elongated amino acids which are GSL precursors which are non-naturally occurring in the species into which they are introduced—these products forming a further aspect of the present invention.

Methods of the invention may be used to produce non-naturally occurring GSLs, or GSLs which are non-naturally occurring in the species into which they are introduced—these products forming a further aspect of the present invention.

Methods used herein may be used, for example, to increase levels of any of the GSLs discussed herein (e.g. methylsulfinylalkyl GSL) for improved nutraceutical potential or increased methylthioalkyl GSL for improved flavour or increasing biofumigative activity or potential. The methods of the present invention may include the use of GSL-biosynthesis modifying nucleic acids of the invention, optionally in conjunction with the manipulation (e.g. over-expression or down-regulation) other genes affecting GSL biosynthesis known in the art.

The invention further provides a method of influencing or affecting GSL biosynthesis (e.g. via the biosynthesis of chain elongated amino acids which are GSL precursors) in a host such as a plant, the method including causing or allowing transcription of a heterologous GSL-biosynthesis modifying nucleic acid sequence as discussed above within the cells of the plant. The step may be preceded by the earlier step of introduction of the GSL-biosynthesis modifying nucleic acid into a cell of the plant or an ancestor thereof.

For example the invention provides various methods of influencing a GSL biosynthetic catalytic activity in a cell (preferably a plant cell). The methods comprise the step of modifying in that cell the activity (e.g. nature or concentration) of an enzyme capable of catalysing cleave of gamma-glutamyl peptide bonds or providing another biological activity described in Table 1a or 1b above.

Such methods will usually form a part of, possibly one step in, a method of producing a GSL or a chain-elongated amino acid, or modifying the production of a GSL or a chain-elongated amino acid, in a host such as a plant. Preferably the method will employ a nucleic acid encoding an GSL modifying polypeptide of the present invention (e.g., in Table 1a or 1b) or variant thereof, as described above.

The methods of the present invention embrace both the in vitro and in vivo production, or manipulation, of one or more GSLs or chain-elongated amino acids. For example, polypeptides such as those in Table 1a or 1b) or variants thereof may be employed in fermentation via expression in microorganisms such as e.g. *E. coli*, yeast and filamentous fungi and so on. As noted above, the newly characterised GSL-related sequences of the present invention may be used in these organisms in conjunction with known biosynthetic genes.

As discussed in more detail below, in this and other aspects of the invention, when used in vitro the enzyme will generally be in isolated, purified, or semi-purified form. Optionally it will be the product of expression of a recombinant nucleic acid molecule.

Likewise the in vivo methods will generally involve the step of causing or allowing the transcription of, and then translation from, a recombinant nucleic acid molecule encoding the enzyme.

Thus in further aspects of the present invention there are disclosed:

A method of producing a GSL or a chain-elongated amino acid, or modifying the production of a GSL or a chain-elongated amino acid, said method comprising use of a nucleic acid molecule encoding a polypeptide of Table 1a or 1b or variant thereof, as described above.

A method of producing a GSL or a chain-elongated amino acid, or modifying the production of a GSL or a chain-elongated amino acid, said method comprising use of a polypeptide of Table 1a or 1b or variant thereof, as described above.

A method of producing a GSL or a chain-elongated amino acid, or modifying the production of a GSL or a chain-elongated amino acid, said method comprising use of a plant, plant cell, or microorganism transformed with a nucleic acid molecule encoding a polypeptide of Table 1a or 1b or variant thereof, as described above.

A method of producing a GSL or a chain-elongated amino acid, or modifying the production of a GSL or a chain-elongated amino acid, said method comprising use of a plant, plant cell, or microorganism expressing a heterologous polypeptide of Table 1a or 1b or variant thereof, as described above.

Corresponding methods for producing GSL-degradation products, or modifying the production of GSL degradation products, are likewise disclosed.

As described in the introduction, GSL compounds play a role in seed quality, cancer preventive properties, herbivore and pathogen resistance, biofumigation activity and so on. Thus the present invention includes a method of altering any one or more of these characteristics in a plant, comprising use of a method as described hereinbefore. Specific examples include alteration of flavour or nutritional (or 'nutraceutical') value of a plant or plant product.

Much of the foregoing discussed has been concerned with the genetic modification of plants by use of artificial recombinant nucleic acids. However the disclosure of the GSL-genes of the present invention also provides novel methods of plant breeding and selection, for instance to manipulate phenotype such as meal quality of oilseeds crucifers, anticarcinogenic activity and flavour of horticultural crucifers, and/or resistance to herbivores and pathogens.

A further aspect of the present invention provides a method for assessing the GSL phenotype of a plant, the method comprising the step of determining the presence and/or identity of a GSL-biosynthesis modifying allele therein comprising the use of a nucleic acid as described above. Such a diagnostic test may be used with transgenic or wild-type plants, and such plants may or may not be mutant lines e.g. obtained by chemical mutagenesis.

The use of diagnostic tests for alleles allows the researcher or plant breeder to establish, with full confidence and independent from time consuming biochemical tests, whether or not a desired allele is present in the plant of interest (or a cell thereof), whether the plant is a representative of a collection of other genetically identical plants (e.g. an inbred variety or cultivar) or one individual in a sample of related (e.g. breeders' selection) or unrelated plants.

The present disclosure provides sufficient information for a person skilled in the art to obtain genomic DNA sequence for any given new or existing allele (e.g. the various homologues discussed above) and devise a suitable nucleic acid- and/or polypeptide-based diagnostic assay. DNA genomically linked to the alleles may also be sequenced for flanking markers associated with the allele. The sequencing polymorphisms that may be used as genetic markers may, for example, be single nucleotide polymorphisms, multiple nucleotide polymorphisms or sequence length polymorphisms. The polymorphisms could be detected directly from sequencing the homologous genomic sequence from the different parents or from indirect methods of indiscriminantely screening for visualizable differences such as CAPs markers or DNA HPLC.

In designing a nucleic acid assay account is taken of the distinctive variation in sequence that characterises the particular variant allele.

For example GSL genes of the invention or homologues thereof can be used in marker assisted selection programmes to reduce antinutritional GSL in seed meals of Brassica oilseed crops (e.g. *B. napus, B. rapa* (syn *B. campestris*), *B. juncea, B. carinata*), to enhance cancer preventive GSL in *Brassica* vegetables crop and other cruciferous salads and to modify plant-herbivore interactions.

For example, markers developed from the homologues for use in breeding increased levels of methylsulfinylalkyl GSL for improved nutraceutical potential or increased methylthioalkyl GSL for improved flavour. As noted above, breeding may also be used to alter disease resistance and biofumigation potential resulting in a better breaking crop e.g. in previously uncultivated or disease-infested land.

Thus in one embodiment of the present invention, a method is described which employs the use of DNA markers derived from or associated with GSL genes of the present invention (or homologues thereof from Brassicas and other cruciferous plants) that segregate with specific GSL profiles. In one embodiment of this method, the use of the DNA markers, or more specifically markers known as flanking QTLs (quantitative trait loci) are used to select the genetic combination in Brassicas that leads to elevated levels of methylsulfinylalkyl GSLs.

Thus aspects of the invention embrace the selective increase of cancer preventive GSL derivatives in cruciferous crop species, and to cruciferous crop species with enhanced levels of cancer preventive GSL derivatives and in particular edible *Brassica* vegetables and cruciferous salads with elevated levels of the cancer preventive GSL derivatives methylsulfinylalkyl isothiocyanate. The present invention also provides methods for selection of genetic combinations of broccoli containing high levels of cancer preventive GSL derivatives and methods to evaluate the cancer preventive properties of these genetic combinations.

In a breeding scheme based on selection and selfing of desirable individuals, nucleic acid or polypeptide diagnostics for the desirable allele or alleles in high throughput, low cost assays as provided by this invention, reliable selection for the preferred genotype can be made at early generations and on more material than would otherwise be possible. This gain in reliability of selection plus the time saving by being able to test material earlier and without costly phenotype screening is of considerable value in plant breeding.

Nucleic acid-based determination of the presence or absence of one or more desirable alleles may be combined with determination of the genotype of the flanking linked genomic DNA and other unlinked genomic DNA using established sets of markers such as RFLPs, microsatellites or SSRs, AFLPs, RAPDs etc. This enables the researcher or plant breeder to select for not only the presence of the desirable allele but also for individual plant or families of plants which have the most desirable combinations of linked and unlinked genetic background. Such recombinations of desirable material may occur only rarely within a given segregating breeding population or backcross progeny. Direct assay of the locus as afforded by the present invention allows the researcher to make a stepwise approach to fixing (making homozygous) the desired combination of flanking markers and alleles, by first identifying individuals fixed for one flanking marker and then identifying progeny fixed on the other side of the locus all the time knowing with confidence that the desirable allele is still present.

Accordingly in this embodiment of the present invention one potential method to produce a GSL-biosynthesising plant having elevated levels of methylsulfinylalkyl GSLs is described which comprises:

I.) Preparing F1 hybrid plants;

II.) Analyzing F1 hybrids by screening with DNA markers derived from or associated with GSL genes of the present invention (or homologues thereof), and selecting hybrids for backcrossing with one parental line;

III.) Analysis of DNA markers derived from or associated with GSL genes of the present invention (or homologues thereof) in individual plants of the B1 (Backcross 1) generation and selection of lines with the optimum GSL genotype as related to the DNA markers derived from or associated with GSL genes of the present invention;

IV.) One or two further rounds of DNA marker assisted backcrossing with selection of plants as per II to generate production quality germplasm.)

This method is only an example and not all inclusive. DNA marker assisted selection utilizing DNA markers derived from or associated with GSL genes of the present invention (or homologues thereof) can be successfully utilized in any genetic crossing scheme to optimize the efficiency of obtaining the desired GSL phenotype.

Purified protein according to the present invention, or a fragment, mutant, derivative or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunizing a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80-82). Antibodies may be polyclonal or monoclonal.

As an alternative or supplement to immunizing a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with the desired function (in accordance with embodiments disclosed herein), comprising screening candidate polypeptides with a polypeptide comprising the antigen-binding domain of an antibody (for example whole antibody or a suitable fragment thereof, e.g. scFv, Fab) which is able to bind a polypeptide or fragment, variant or derivative thereof according to the present invention or preferably has binding specificity for such a polypeptide. Specific binding members such as antibodies and polypeptides comprising antigen binding domains of antibodies that bind and are preferably specific for a polypeptide or mutant, variant or derivative thereof according to the invention represent further aspects of the present invention, particularly in isolated and/or purified form, as do their use and methods which employ them.

Candidate polypeptides for screening may for instance be the products of an expression library created using nucleic acid derived from an plant of interest, or may be the product of a purification process from a natural source. A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridization to candidate nucleic acid, or by searching computer sequence databases, as discussed further below.

Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic.

The invention will now be further described with reference to the following non-limiting Figures and Examples. Other embodiments of the invention will occur to those skilled in the art in the light of these.

Any title and sub-title in the description herein is for convenience only and should not be interpreted as limiting the disclosure in any way.

The disclosure of all references cited herein, inasmuch as it may be used by those skilled in the art to carry out the invention, is hereby specifically incorporated herein by cross-reference.

FIGURES

FIG. 1.
Constructs used for biosynthesis of benzylglucosinolate.
AtST5a: cDNA of At1g74100
UGT74B1: cDNA of At1g24100
SUR1: cDNA of At2g20610
CYP83B1: cDNA of At4g31500
CYP79A2: cDNA of At5g05260
GGP1: cDNA of At4g30530
The different cDNAs of the individual constructs are joined by 2A coding sequences to allow their expression as independent proteins from a single promoter.

FIG. 2.
Glucosinolate analysis in N. benthamiana leaves infiltrated with construct C17 alone, or combination C15+C17. Representative chromatograms of individual samples from the HPLC analysis are shown. For the combination C15+C17, an extra peak is evident. This peak's UV spectrum is identical to that of a BGSL standard (not shown), and the retention time is the same than for the standard.

Figure 3:
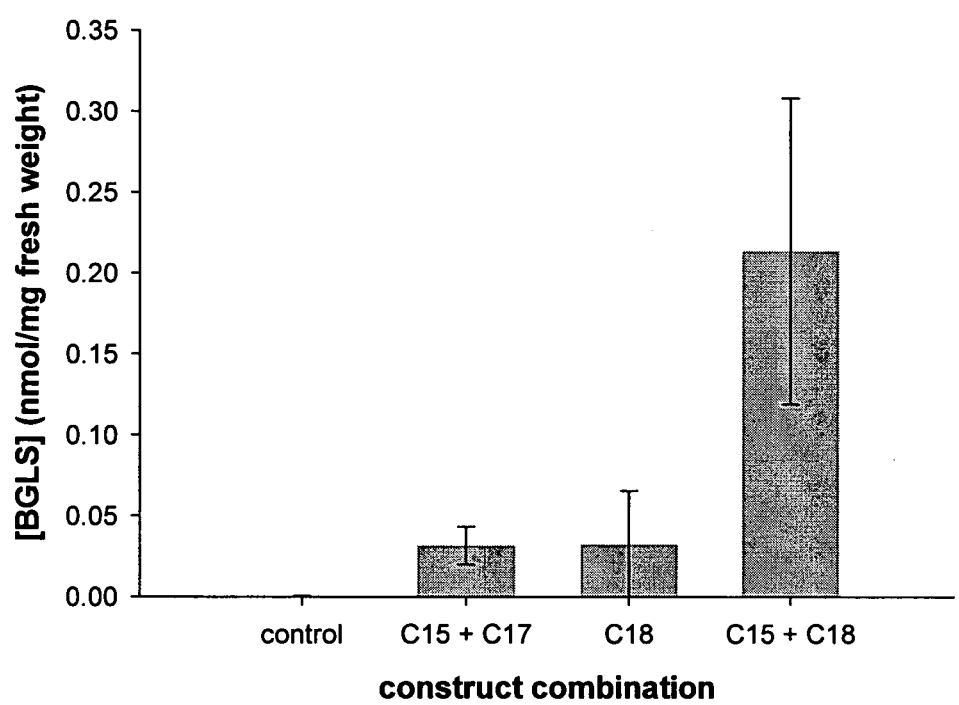

FIG. 3.
BGSL production in N. benthamiana leaves infiltrated with construct combinations C15+C17 (five genes altogether), C15+C18 (five genes plus GGP1), C18 alone (CYP79A2, CYP83B1, and GGP1), and a control infiltration. Leaves were harvested and analyzed for BGSL 7 days post infiltration (dpi). Each column represents the average of eight independent samples, and error bars show standard deviation.

FIG. 4.
Characterization of GGP1. (a) Expression and purification of GGP1. His-tagged GGP1 was expressed in E. coli from the pRSET-A vector upon induction with IPTG. The SDS-PAGE gel to the left shows the purification process through a His-tag affinity column. The gel to the right shows a similar process, but using an empty pRSET-A vector as negative control. For both gels, lane 1 was loaded with a crude soluble protein extract, lane 2 with the flow-through after loading the affinity column, lane 3 with the flow-through of the washing step, and lane 4 with the purified protein eluted with 500 mM imidazole. The expected MW of the tagged protein is 31.5 kD. (b) Scheme of the enzymatic reaction. In the absence of SUR1, the hydrolysis product (a Cys-Gly-conjugate) is expected to undergo non-enzymatic cyclization (Hansen et al., 2001). (c) LC-MS analysis of reaction mixtures containing 20 µM GS-X and either 200 ng of purified GGP1 or 200 ng protein from the imidazole eluate of the negative control (empty vector). The analysis was performed after 20 min of reaction, and the total ion chromatograms are shown. The MS spectrum of the product peak is embedded, which presents an $[M+H]^+$ mass of 278.9, corresponding to the cyclized Cys-Gly conjugate. (d) Determination of $K_m$ using GS-X as substrate. The average of four technical replicates is shown, and the error bars represent 95% CIs. The data was fitted to the hyperbolic curve shown, from which the $K_m$ value of 56.6±19 µM (SE) was inferred assuming Michaelis-Menten kinetics FIG. 5
In vitro activity of recombinant GGP1 against gamma-glutamyl-p-nitroanilide (GPNA). The generation of cleaved product (p-nitroanilide) was measured at 6 different time-points by the change in absorption at 405 nm. The data points in the graph are an average of two replicates in which the variation was no higher than 15% (compared to the average). The regression lines presented are of second order for the assays with GGP1 and of first order for the control assays. The graph shows that assays with a crude extract containing recombinant GGP1 present a much higher activity (around 10 times higher in the linear part of the GGP1 curve) than assays with a control extract.

Figures 5, 6:
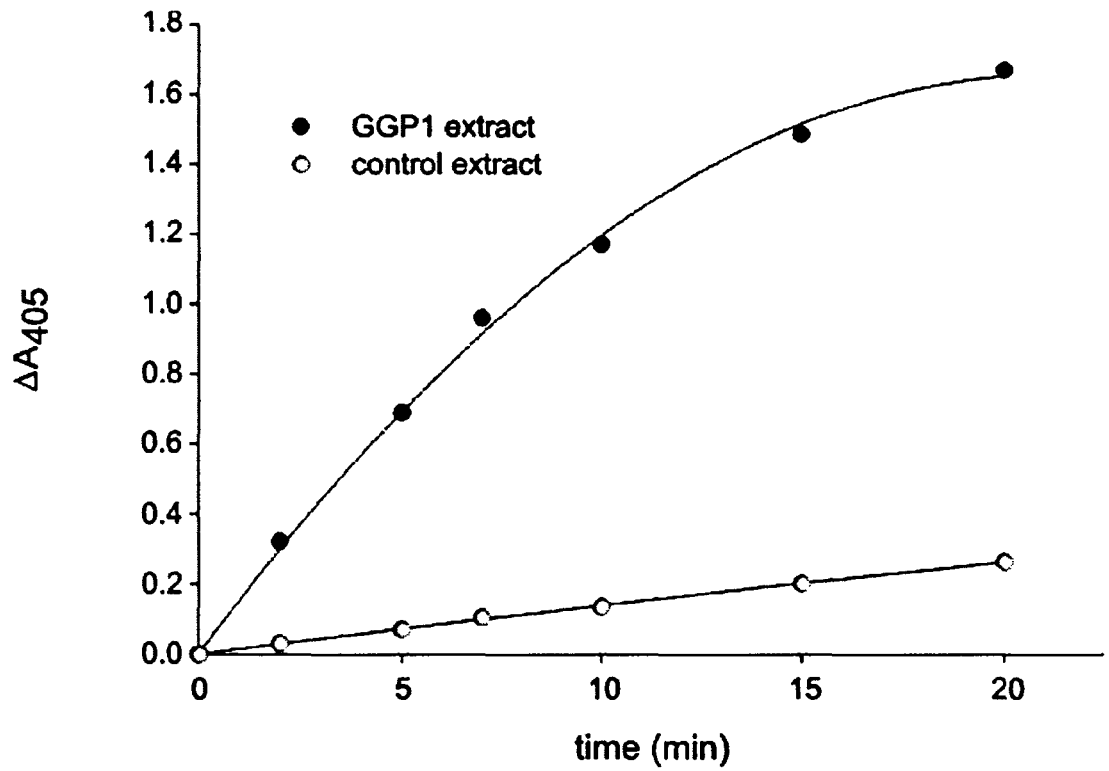

FIG. 6.
Amino acid identity of GGP1 family members in A. thaliana. Amino acid sequences were aligned by pairwise alignment using either clustalW or BLASTp algorithms. Results from clustalW are displayed in the lower left diagonal and BLASTp in the upper right diagonal.

Figure 7:
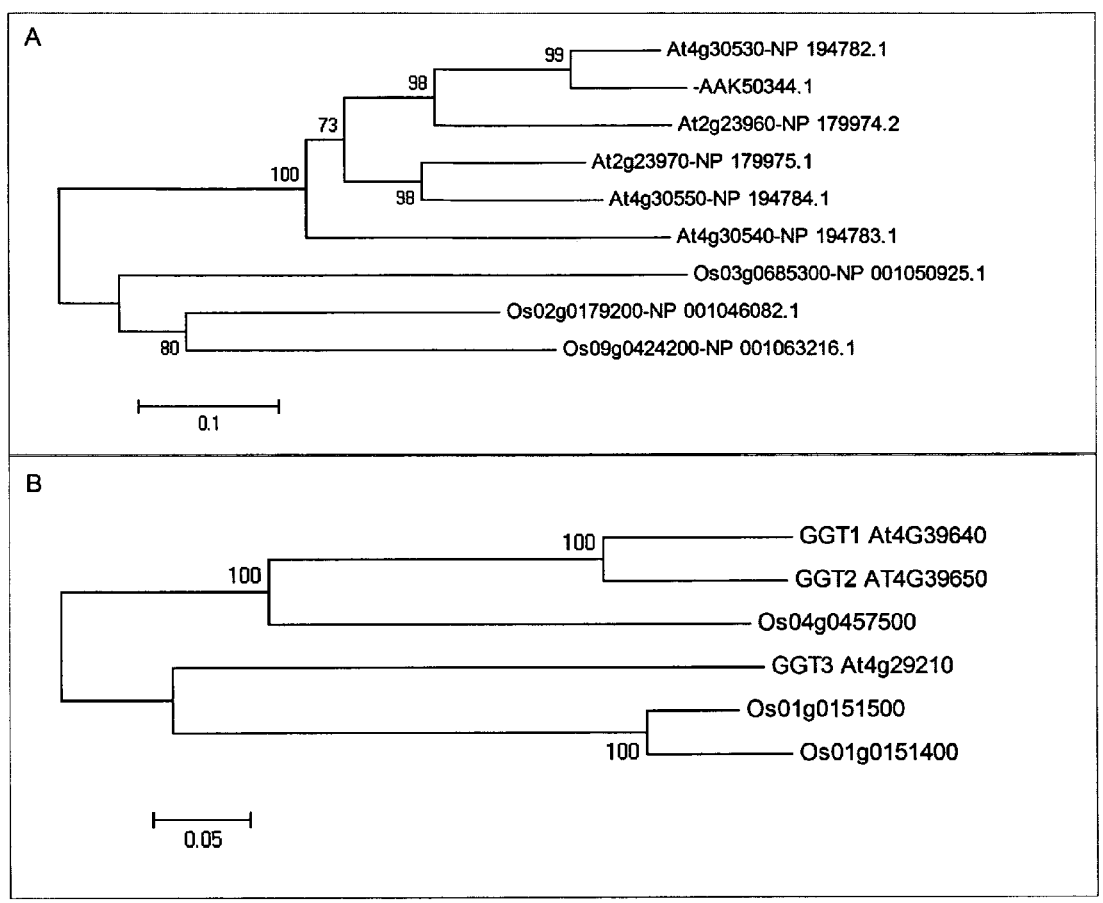

FIG. 7.
Phylogenic trees of GGP and GGT-family proteins from Brassica species and Rice (Oryza sativa): Trees are presented as bootstrap consensus phylograms. Evolutionary distance is indicated in lover left corner. Bootstrap analysis used 1000 replicates and percentage values are presented at the nodes. A. Phylogram of GGP family. AAK50344=unknown protein from Brassica carinata. B. Phylogram of GGT family.

Figure 8:
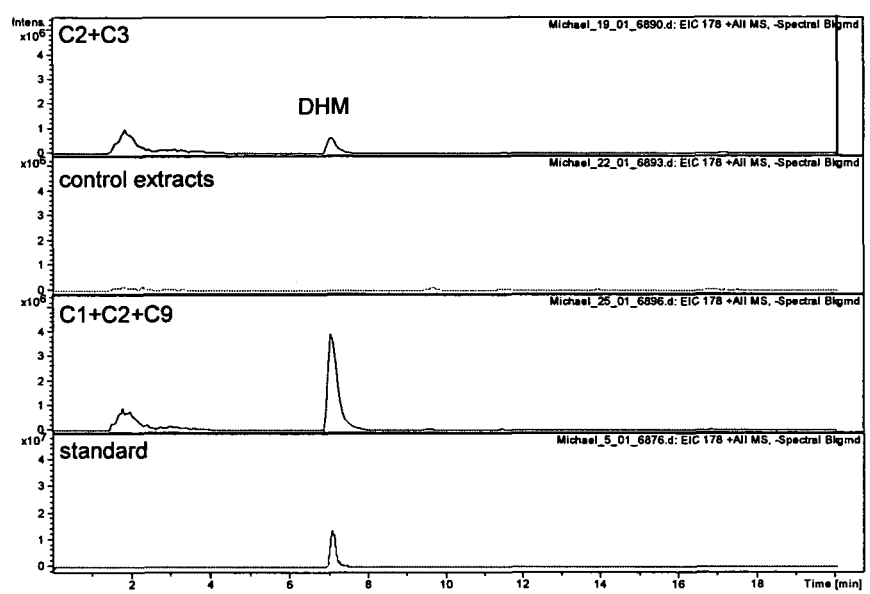

FIG. 8.
DHM biosynthesis in N. benthamiana.
Total N. benthamiana extracts were analyzed by LC-MS. In the selected ion trace (m/z=178), a new peak, co-migrating with a DHM-standard was found. The dominant ion in this peak had an m/z ratio of 178, corresponding to DHM.

FIG. 9.

a) Extracted ion traces corresponding to the short chain MET-derived desulphoglucosinolates: 350 (3-MTP), 366 (3-MSP), 364 (4-MTB), 380 (4-MSB).

b) Extracted ion traces corresponding to chain-extended ILE\LEU-derived GSLs.

FIG. 10.

Chain-elongation of MET. MET is deaminated by BCAT4. The 2-oxo-acid is conjugated with acetyl-CoA by MAM1, isomerized by one of two redundant aconitases, and finally decarboxylated by isopropylmalate dehydrogenase, thereby yielding a chain-elongated t-oxo acid. This compound may be trans-aminated to form homo-methionine or go through one additional cycle of chain-elongation to form 2-oxo-6-methylthiohexanoic acid, which is trans-aminated to DHM.

FIG. 11.

Glucosinolate biosynthesis from DHM or HM. Compounds in the box are unstable. The aci-nitro-compound is a hypothetical intermediate.

FIG. 12.

Constructs used for biosynthesis of DHM and 4-MSB.

MAC-T: Methylthioalkyl α-ketoacid chloroplastidic transporter At4g12030

IPMDH: 3-isopropylmalate dehydrogenase At1g31180,

AC1: Aconitase At2g43100, AC2: Aconitase At3g58990, rbs: Rubisco small subunit targeting sequence, FMO: Flavin containing monooxygenase, At1g65860 (SEQ ID NO: 95)

ST: Sulfotransferase, At1g74090, GGP: γ-glutamyl peptidase, At4g30530

FIG. 13.

Time-course study of the accumulation of BGSL (a) and GS-X (b) in leaves co-expressing ORF1 and ORF2, in the presence or absence of GGP1. Mean concentrations are plotted at each time point (n=7-8), and error bars represent 95% Cls.

FIG. 14.

LC-MS analysis of glucosinolates extracts. A) LC-profile, extracted ion chromatogram of the following masses: 366, 380, 394, 408, 422 and 436. Top: control N. benthamiana infiltrated with only the P19 suppressor strain. Bottom: N. benthamiana infiltrated with A. tumefaciens strains harboring constructs containing BCAT4, MAM3, AC1, AC2, IPMDH, cBCAT4, MAC-T, CYP79F1, CYP83A1, GSTF11, GGP1, SUR1, UGT74C1, AtST5b, $FMO_{GS-OX5}$, P19. B) Mass spectra of the respective glucosinolates.

FIG. 15.

Production of I3G in N. benthamiana. A) LC-profile, extracted ion chromatogram of m/z 391. Top: Control plants infiltrated with only the P19 suppressor strain. Bottom: N. benthamiana infiltrated with Agrobacterium harboring the following genes: CYP79B2, CYP83B1, SUR1, GGP1, GSTF9, UGT74B1, AtST5a, and the P19 suppressor strain. B) Mass spectrum of the I3G peak.

FIG. 16.

HPLC analysis of purified intact I3G subsequently derivatized to desulpho-I3G. A) UV absorbance at 229 nm and acetonitrile elution gradient. B) UV-spectrum of the I3G peak (7.6 min).

FIG. 17.

LC-MS analysis of N. benthamiana infiltrated with BGSL and I3G biosynthetic genes. A) LC-MS profile, extracted ion chromatograms of m/z 352 and 391. Top: Control plants infiltrated with only the P19 suppressor strain. Bottom: N. benthamiana infiltrated with Agrobacterium harboring the following genes: CYP79A2, CYP79B2, CYP83B1, SUR1, GGP1, GSTF9, UGT74B1, AtST5a, and the P19 suppressor strain. B) Mass spectrum of the I3G and BGSL peaks.

FIG. 18.

Reconstitution of aromatic GSL biosynthesis in stable transgenic tobacco plants. a) Wildtype tobacco plants (WT) were transformed with construct C15. To select the best C15 line, four different lines were fed PATH through cut petioles, and the PATH-to-BGSL conversion was measured. The graph bars show the mean percentage of conversion of 7 leaves of a particular genotype [four C15 transgenic lines and a WT plant], and error bars represent standard deviations. b) The best C15 line (C15-27.1) was transformed with construct C18, and four C15+C18 transgenic lines produced BGSL without any feeding of intermediates. The graph bars show the mean amount of BGSL in young (first leaf bigger than 10 cm in length) and old (third leaf from the bottom) leaves of four different three month-old transgenic C18+C15 lines. Error bars represent standard deviations.

FIG. 19.

Scheme showing generation and recycling of PAPS (adenosine 3'-phosphate 5'-phosphosulfate).

SEQUENCES

The following genes were employed in Exemplification of the present invention. Those in bold are newly characterised in the present specification. Those with SEQ ID NO.s are set out for ease of reference in an Annex to the description.

TABLE 2 genes which were employed in Exemplification of the present invention.

| gene | locus | Abbreviation | Gene transcript, or SEQ ID NO | Protein ID SEQ ID NO |
| --- | --- | --- | --- | --- |
| Branched chain amino transferase 4 | At3g19710 | BCAT4 | NM_112861.3 | NP_188605.1 |
| Branched chain amino transferase 3 | At3g49680 | BCAT3 | NM_114828.4 | NP_566923.1 |
| MAM1 | At5g23010 | MAM1 | NM_122207.2 | NP_197692.1 |
| Aconitase | At2g43100 | AC1 | 13 | 14 |
| Aconitase | At3g58990 | AC2 | 15 | 16 |
| Isopropylmalate dehydrogenase | At1g31180 | IPMDH | 17 | 18 |
| methylthioalkyl alfa-ketoacid chloroplastidic transporter (MAC transporter) | At4g12030 | MAC-T | 19 | 20 |

TABLE 2-continued genes which were employed in Exemplification of the present invention.

| gene | locus | Abbreviation | Gene transcript, or SEQ ID NO | Protein ID SEQ ID NO |
|---|---|---|---|---|
| CYP79F1 | At1g16410 | CYP79F1 | NM_101507.2/ NM_202111.1 | NP_563996.2/ NP_973840.1 |
| CYP79A2 | At5g05260 | CYP79A2 | NM_120608.1 | NP_568153.1 |
| CYP83A1 | At4g13770 | CYP83A1 | NM_117451.2 | NP_193113.1 |
| CYP83B1 | At4g31500 | CYP83B1 | NM_119299.2 | NP_194878.1 |
| γ-glutamyl peptidase | At4g30530 | GGP1 | 1 | 2 |
| Glutathione-S-transferase 11 | At3g03190 | GSTF11 | 21 | 22 |
| Sulfotransferase | At1g74090 | ST | NM_106069.2 | NP_177549.1 |
| Sulfotransferase 5a | At1g74100 | AtST5a | NM_106070.2 | NP_177550.1 |
| UDP-glucuronysyl transferase | At2g31790 | GT | NM_128737.3 | NP_180738.1 |
| UDP-glucuronosyl transferase 74B1 | At1g24100 | UGT74B1 | NM_102256.2 | NP_173820.1 |
| Superroot1 | At2g20610 | SUR1 | NM_127622.2/ NM_201760.1 | NP_179650.1/ NP_973489.1 |
| Flavin-containing monooxygenase | At1g65860 (SEQ ID NO: 95) | FMO | NM_105258.2 | NP_176761.1 |

EXAMPLES

Any methods of the invention not specifically described below may be performed by one of ordinary skill in the art without undue burden in the light of the disclosure herein.

Materials and Methods

Examples 1 and 2

Cloning

The following genes were amplified from total cDNA of *Arabidopsis* with primers situated in the UTRs into pBN1 through USER-based cloning, as described previously (Nour-Eldin et al., 2006): At3g19710, At3g49680, At5g23010, At2g43100, At3g58990, At1g31180, At4g13770, At4g30530, At3g03190, At2g31790, At2g20610. The chloroplast-targeting signal of rbcS was also cloned from cDNA.

The following genes were cloned from cDNAs cloned previously:
At4g12030 (Nour-Eldin, unpublished data), At1g16410 (Hansen et al., 2001), At4g30530 (γ-GP, Geu-Flores et al., unpublished data), At3g03190 (GSTF11, Riken clone RAFL09-80-K17), At2g20610 (Mikkelsen et al., 2004), At1g74090 (Piotrowski et al., 2004).

The FMO (At1g65860 (SEQ ID NO: 95)) was kindly provided in the plant transformation vector described previously (Hansen et al., 2007).

Genes were amplified by PCR to incorporate USER-sequences and 2A sequences. The following primers were used on the different genes as follows:

```
BCAT4 primers:
3:GGCTTAAUGAATTCATGGCTCCTTCTGCGCA (SEQ ID NO: 23)

4:ACATCTCCUGCCAACTTAAGCAAATCAAAATTCAAAGTTTGACCA
GAACCGCCCTGGCGGTCAATC (SEQ ID NO: 24)

41:GGTTTAAUCTCGAGCTATCAGCCCTGGCGGTCAATC (SEQ ID NO: 25)

42:ACTCTCTCUTACCTTATGGCTCCTTCTGCGCA (SEQ ID NO: 26)

MAM1 primers:
7:AGGAGATGUGGAATCTAACCCAGGACCTATGGCTTCATCGCTTCT
GAC (SEQ ID NO: 27)

8:ACCACAAGUCAAAAGAGAACCTCTACCTTCACCAGAACCCACATT
CGATGAAACCTGAGG (SEQ ID NO: 28)

25:GGTTTAAUCTCGAGCTATCACACATTCGATGAAACCTGAGG (SEQ ID NO: 29)

Acon1 primers:
11:GGCTTAAUGGATCCATGGCGTATTCTCTTCCTACATTTC (SEQ ID NO: 30)

12:ACATCTCCUGCCAACTTAAGCAAATCAAAATTCAAAGTTTGACC
AGAACCAGCTAATGATGGAATCATTCCCAT (SEQ ID NO: 31)

26:ACCACAAGUCAAAAGAGAACCTCTACCTTCACCAGAACCAGCTA
ATGATGGAATCATTCCCAT (SEQ ID NO: 32)
```

-continued

Acon2 primers:
15:AGGAGATGUGGAATCTAACCCAGGACCTATGGCGACTTCTCAGC
AATT (SEQ ID NO: 33)

16:ACCACAAGUCAAAAGAGAACCTCTACCTTCACCAGAACCAGCAG
AAGGAATCATGCCG (SEQ ID NO: 34)

27:GGCTTAAUGGATCCATGGCGACTTCTCAGCAATT (SEQ ID NO: 35)

IPMDH primers:
19:ACTIGTGGUGATGTCGAAGAAAATCCAGGCCCAATGGCGGCGTT
TTTGC (SEQ ID NO: 36)

20:GGTTTAAUCCGCGGTCACTAAACAGGAACTTTGGAGTCCACTG (SEQ ID NO: 37)

MAC-T primers:
23:ACTTGTGGUGATGTCGAAGAAAATCCAGGCCCAATGATGGGTGT
GATATCTCCGACTG (SEQ ID NO: 38)

24:GGTTTAAUCTCGAGCTATCACTCCTTTCTGCCATATGGT (SEQ ID NO: 39)

BCAT3 primers:
29:GGCTTAAUGGATCCATGGAGAGAGCAGCAATTCTCC (SEQ ID NO: 40)

30:ACATCTCCUGCCAACTTAAGCAAATCAAAATTCAAAGTTTGACC
AGAACCACTAAGATTCACAGTCCATTTCATGTT (SEQ ID NO: 41)

31:AGGAGATGUGGAATCTAACCCAGGACCTATGGAGAGAGCAGCAA
TTCTCC (SEQ ID NO: 42)

32:ACCACAAGUCAAAAGAGAACCTCTACCTTCACCAGAACCACTAA
GATTCACAGTCCATTTCATGTT (SEQ ID NO: 43)

rbcS primers:
43:AGAGAGAGUCTCAAACTTCTTCTTTCC (SEQ ID NO: 44)

44:GGCTTAAUGAATTCATGGCTTCCTCTATGCTCTCTTCC (SEQ ID NO: 45)

ST primers:
51:GGCTTAAUGGATCCATGGAATCAGAAACCCTAACC (SEQ ID NO: 46)

52:ACATCTCCUGCCAACTTAAGCAAATCAAAATTCAAAGTTTGACC
AGAACCTTTACCATGTTCAAGCAAGCC (SEQ ID NO: 47)

GT primers:
53:AGGAGATGUGGAATCTAACCCAGGACCTATGAGTGAAGCAAAGA
AGGGTC (SEQ ID NO: 48)

54:ACCACAAGUCAAAAGAGAACCTCTACCTTCACCAGAACCAGTCA
AAAGAGCAACAAACTCATC (SEQ ID NO: 49)

SUR1 primers:
55:ACTTGTGGUGATGTCGAAGAAAATCCAGGCCCAATGAGCGAAGA
ACAACCACAC (SEQ ID NO: 50)

56:GGTTTAAUCCGCGGTCACTACATTTCGAGATTATTATCACTCAG
TTTC (SEQ ID NO: 51)

γ-GP primers:
57:GGCTTAAUTCTAGAATGGTGGAGCAAAAGAGATACG (SEQ ID NO: 52)

58:ACCACAAGUCAAAAGAGAACCTCTACCTTCACCAGAACCGTTAG
TTGGAACTCTGCCTTTGAG (SEQ ID NO: 53)

GSTF11 primers:
59:ACTTGIGGUGATGTCGAAGAAAATCCAGGCCCAATGGTGGTCAA
AGTATATGGGC (SEQ ID NO: 54)

60: GGTTTAAUCCGCGGTCACTAATAGGCAGCCAATTCCATGA (SEQ ID NO: 55)

-continued

CYP83A1 primers:
61:GGCTTAAUTCTAGAATGGAAGATATCATCATCGGC (SEQ ID NO: 56)

62:ACCACAAGUCAAAAGAGAACCTCTACCTTCACCAGAACCATACT
TGTTCACTTTCTCTGGAACAAG (SEQ ID NO: 57)

CYP79F1 primers:
63:ACTTGTGGUGATGTCGAAGAAAATCCAGGCCCAATGATGAGCTT
TACCACATCATT (SEQ ID NO: 58)

64:GGTTTAAUGGATCCTCACTAAGGACGGAACTTTGGATAAAGG (SEQ ID NO: 59)

65:GGCTTAAUTCTAGAATGATGAGCTTTACCACATCATT (SEQ ID NO: 60)

The constructs were generated by the USER-fusion method (Geu-Flores et al., 2007) by adding the MP27 plant transformation vector to the following purified PCR fragments as described below.

Construct1: 3+4, 7+8, 11+12, construct2: 11+12, 15+16, 19+20, construct3: 3+4, 7+25, construct4: 11+26, 19+20, construct5: 16+27, 19+20, construct6: 29+30, 15+16, 19+20, construct7: 11+12, 31+32, 19+20, construct8: 41+42, 43+44, construct9: 4+42, 7+25, 43+44, construct10: 51+52, 53+54, 55+56, construct11: 57+58, 59+60, construct12: 61+62, 63+64, construct13: 64+65. Construct 14 only contained the FMO, and has been described previously (Hansen et al., 2007).

The resulting fragments were mixed in approximately equal-molar ratios with the MP27-vector, USER-treated as described previously (Nour-Eldin et al., 2006), and transformed into *E. coli*. Resulting positive clones were sequenced and transformed into *Agrobacterium tumefaciens* strain C58C1 by electroporation.

Infiltration of *N. benthamiana*

*A. tumifaciens* cultures were grown at 28° C. in YEP media with 50 mg L$^{-1}$ Kanamycin and 34 mg L$^{-1}$ Rifampicilin. Cells were harvested by centrifugation, 10 minutes at 3000 g, and resuspended to a final OD of 0.75 in 10 mM MES buffer with 10 mM MgCl$_2$ and 100 µM Acetosyringone. Following a 150 minutes shaking incubation, 50 rpm at room temperature, the *agrobacterium* strains were mixed in roughly equimolar amounts and approximately one-quarter volume of the P19 suppressor-strain (Voinnet et al., 2003) was added. The *agrobacteria* were injected into the leaves of three-four weeks old *N. benthamiana* plants using a 1 mL syringe without the metal tip.

Extraction

Total metabolites were extracted from leaf disks by boiling for 3 minutes in 85% methanol. The supernatant was evaporated, resuspended in 10% methanol, filtered through a 0.22 µm filter and analyzed by LC-MS.

Glucosinolates were extracted by applying the total extract on a Sephadex DEAE A25 column, washed with 85% methanol, water, desulfated with *Helix Pomatia* sulfatase (Sigma) and eluted with water. The resulting desulphoglucosinolates were analyzed by LC-MS as described previously (Mikkelsen and Halkier, 2003).

Materials and Methods

Examples 3, 4 and 10

Cloning of Expression Constructs

The cDNAs of each gene were amplified by PCR using the following plasmid templates and a pair of the following primers:

CYP79A2 (At5g05260)
Plasmid template: pSP19g10L+'native' CYP79A2 cDNA, cloned by Wittstock and Halkier (2000)
Primers:

1) ACTTGTGGUGATGTCGAAGAAAATCCAGGCCCAATGCTCGCGTTTA
TTATAGG (SEQ ID NO: 61)

2) GGTTTAAUGCATGCACTAGTTTAGGTTGGATA CACATGTGGAGCT
(SEQ ID NO: 62)

CYP83B1 (At4g30500)
Plasmid template: pBluescript II SK+CYP83B1 cDNA, cloned by Hansen et al. (2001)
Primers:

3)
AGGAGAUGTGGAATCTAACCCAGGACCTATGGATCTCTTATTGATTATAG
CCGGTTTAGT (SEQ ID NO: 63)

4)
GGCTTAAUGAATTCACTAGTATGGATCTCTTATTGATTATAGCCGGT
(SEQ ID NO: 64)

5)
ACCACAAGUCAAAAGAGAACCTCTACCTTCACCAGAACCGATGTGTTTCG
TTGGTGCAAGAACGA (SEQ ID NO: 65)

GGP1 (At4g30530):
Plasmid template: RAFL06-16-J02 from RIKEN Bioresource Center
Primers:

6)
GGCTTAAUGAATTCACTAGTATGGTGGAGCAAAAGAGATA
(SEQ ID NO: 66)

7a)
ATCTCCUGCCAACTTAAGCAAATCAAAATTCAAAGTTTGACCAGAACCGT
TAGTTGGAACTCTGCCTT (SEQ ID NO: 67)

7b)
GGTTTAAUCGCATGCACTAGTCTAGTTAGTTGGAACTCTGCCT
(SEQ ID NO: 68)

SUR1 (At2g20610):
Plasmid template: pET9D+SUR1 cDNA, cloned by Mikkelsen et al. (2004)
Primers:

8)
GGCTTAAUATGAGCGAAGAACAACCACACGCCA (SEQ ID NO: 69)

9)
GGTTTAAUTTACATTTCGAGATTATTATCACTCAG (SEQ ID NO: 70)

-continued

10)
ATGCGGGACGTCGAGGAGAATCCTGGCCCAATGAGCGAAGAACAACCACA
CGCC (SEQ ID NO: 71)

11)
AATAACGAGCTCGGTACCTTACATTTCGAGATTATTATCACTCAGITTCA
AAGCT (SEQ ID NO: 72)

UGT74B1 (At1g24100)
Plasmid template: RAFL04-19-M06 from RIKEN Bioresource Center
Primers:

13)
ACGTGGAGCCAACCCAGGGCCTTGGTCTCATCCTCAATTTGAAAAGATGG
CGGAAACAACTCCCAAAGTG (SEQ ID NO: 73)

14)
ACCGCAGTTAGCAGACTTCCICTGCCCTCCTTCCCTAAACTCTCTATAAA
CTCGTTAATGCT (SEQ ID NO: 74)

AtST5a (At1g74100)
Plasmid template: RAFL05-13-F01 from RIKEN Bioresource Center
Primers:

15)
AATAACGAATTCCCATGGCTCACCACCACCACCACCACATGGAATCAAAG
ACAACCCAAAACGGATCC (SEQ ID NO: 75)

16)
ACTCCACGCTCCCGCCAACTTGAGAAGGTCAAAATTCAAAGTCTGGTTAT
CATGTTGAAGCAAGCCAGTATCTTTG (SEQ ID NO: 76)

PCR products were assembled into expression constructs C15-19 according to the following scheme (primers used for the PCR are indicated in parenthesis):
C15: AtST5a (15+16), UGT74B1 (13+14), and SUR1 (10+11)
C16: SUR1 (8+9)
C17: CYP79A2 (1+2) and CYP83B1 (4+5)
C18: CYP79A2 (1+2), CYP83B1 (3+5), and At4g30530 (6+7)
C19: At4g30530 (6+7b)

The structure of constructs C15-18 is presented in FIG. 1. In all the cases, the different cDNAs are joined by 2A coding sequences included in the primers.

For construct C15, the PCRs were carried out using HotMaster™ Taq DNA Polymerase (Eppendorf). The mixed PCR products were treated with Klenow and USER™ enzymes, before undergoing ligation. A secondary PCR was performed using primers AATAACGAATTCCCATGGCT (SEQ ID NO: 77) and AATAACGAGCTCGGTACCTTAC (SEQ ID NO: 78), after which the secondary PCR product was cut using EcoRI and SacI restriction enzymes and ligated to a similarly cut pGEM4Z vector (Promega). The construct was subcloned into pRT101 (Töpfer et al., 1987) using EcoRI and KpnI restriction sites, and finally subcloned into pCAMBIA2300 using PstI restriction sites.

For constructs C16-18, the PCRs were carried out using PfuTurbo $C_X$ Hotstart DNA polymerase (Stratagene). Construct C16 was cloned into pCAMBIA330035Su following the USER™ cloning strategy (Nour-Eldin et al.), and constructs C17-18 were cloned directly into the same vector using the USER™ fusion method (Geu-Flores et al.). Positive clones were selected by growthon LB agar plates containing 50 mg/ml Kanamycin. The sequence of all the expression constructs was determined by sequencing, and a single clone lacking non-silent mutations was selected per construct.

Transient Expression of Constructs in *N. benthamiana*

Expression constructs were transformed independently into *A. tumifaciens* strain C58C1 by electroporation. Cultures were grown at 28° C. in YEP media with 50 mg/L kanamycin and 34 mg/L rifampicin. Cells were harvested by centrifugation during 10 minutes at 3000 g and resuspended to a final $OD_{600}$ of 0.7 in 10 mM MES buffer with 10 mM $MgCl_2$ and 100 μM acetosyringone. Following a 150-minute-long incubation with shaking at 200 rpm and at room temperature, the *Agrobacterium* strains to be co-infiltrated were mixed in roughly equimolar amounts. When comparing unequal numbers of strains, an *Agrobacterium* strain harboring GFP in pBI121 (Haselof et al., 1997) was included to ensure equal relative $OD_{600}$. The strain mixtures were infiltrated into the leaves of 3-4 week-old *N. benthamiana* plants using a 1 mL syringe without needle. The plants were then grown under greenhouse conditions until the analysis was performed.

Glucosinolate and LC-MS Analysis

Leaves for glucosinolate analysis of C15-18 and LC-MS analysis of C15, 17 and 18 were harvested, weighted and lyophilized at seven days-post-infiltration (dpi) (C15+17, C18 and C15+18) or 8 dpi (C15+C16). For accumulation studies, leaves were harvested at two, four, six, eight and ten dpi. Leaves were lyophilized as above, tubes sealed with parafilm and stored at 5° C. until subjected to analysis. For single point studies, infiltrated leaves were harvested, weighed and analyzed several days-post-infiltration (dpi). For the time course study using C15+C17, infiltrated leaves were harvested, weighed, lyophilized and stored at 4° C. until analysis. For the time course study comparing C15+C17 with C15+C17+C19, infiltrated leaves were harvested, weighed, frozen and stored at −20° C. until analysis. Extraction of glucosinolates was as described above in respect of Examples 1 and 2. Glucosinolate analysis was performed as described in Hansen et al. (2007). Metabolite profiling was carried out by analytical LC-MS on crude cleared methanolic extracts of a fixed number of leaf discs. The instrument used was an Agilent 1100 Series LC (Agilent Technologies) coupled to a HCTplus ion trap mass spectrometer (Bruker Daltonics). One of two different analysis methods was used. Method A used a Sinergy Fusion-RP column (Phenomenex; 2.5 mM, 100 A, 2×50 mm), and a flow rate of 0.3 mL min$^{-1}$. The mobile phase composition was as follows: A, 0.1% (v/v) formic acid and 50 mM NaCl in water; B, 0.1% (v/v) formic acid in acetonitrile. The gradient program was as follows: 0 to 7.5 min, linear gradient 6% to 19% (v/v) B; 7.5 to 10 min, linear gradient 19% to 100% B. A short column wash and equilibration was performed after each injection. In method B, a Zorbax SB-C18 RRHT column (Agilent; 2.1×50 mm, 1.8 uM) was used. While the mobile phase composition was the same as in method A, the gradient program used was different: 0 to 0.5 min 2% B; 0.5 to 7.5 min, linear gradient 2% to 40% (v/v) B; 7.5 to 8.5 min, linear gradient 40% to 90% B; 8.5 to 11.5 min 90% B. A short column wash and equilibration was also performed after each injection. The flow rate was 0.2 mL min-1 but increased to 0.3 in the interval 11.2 to 13.5 min.

Identification of GGP Family Members

The annotated amino acid sequence of GGP1 (NP_194782) was used as input in a Position Specific Iterated (PSI)-BLAST search using the 'Reference Protein' (refseq_protein) database at NCBI limited to *A. thaliana* sequences. The search was terminated after the third iteration. Four homologues (At4g30540, At4g30550, At2g23960, and At2g23970) were identified.

Construction of Phylogenetic Trees

Amino acid sequences of At4g30530 (GGP1) and At4g29210 (GGT3) were aligned using clustalW from EBI, and used as query in separate PSI-BLAST analysis against all available Brassica spp. and rice (Oryza sativa, japonica cultivar group) sequences present in the refseq_protein database at NCBI. Homologous sequences were selected after the third iteration. Homologues from Brassica spp. not yet present in the refseq_protein database, were identified by standard BLASTp analysis against Brassica sequences present in the Non-redundant protein sequences' database at NCBI. Homologues sequences were aligned with ClustalX (Thompson et al., 1997) using default settings, and the phylogenetic trees were generated in Mega version 4 (Tamura et al., 2007) by the Neighbour Joining method supported by Bootstrap analysis using 1000 replicates. Multiple sequence alignments were generated using clustalW.

Construction of Sequence Identity Tables

Amino acid sequences of GGP1 (At4g30530), At4g30540, At4g30550, At2g23960 and At2g23970 were aquired from the ref_seq protein database at NCBI. Sequence identities were determined by pairwise alignment using either clustalW or BLASTp from NCBI. Default settings were applied for both algorithms.

Construction of GGP1 Bacterial Expression Vector

GGP1 was amplified from plasmid cDNA (Riken) with primers:

```
Forward:  AATAACACTCGAGATGGTGGAGCAAAAGAGATAC
          (SEQ ID NO: 79)

Reverse:  AATAACAGAATTCCTAGTTAGTTGGAACTCTGCCTTT
          (SEQ ID NO: 80)
```

The PCR product was cloned into pRSET A (Invitrogen) using restriction based cloning. pRSET A contain an N-terminal His-tag and has successfully been used for expression of GGT proteins previously (Chu et al., 2003).

Bacterial Expression of GGP1 and Purification

Recombinant GGP1 was expressed in E. coli from the vector pRSET-A (Invitrogen) as an N-terminal His-tag fusion. Cells were grown in LB medium and induced by adding 0.02 mM IPTG at an $OD_{600}$ of 0.1-0.4. After 16 hours of incubation at 18° C. and 220 rpm, cells were harvested and resuspended in binding buffer [100 mM Tris-HCl, 500 mM NaCl, 50 mM imidazole, pH 7.5] supplemented with 1 mM PMSF and 1 mM MgCl. Cell lysis was achieved by lysozyme treatment and subsequent sonication. Cell debris was spun down for 20 min at 20 000 g, and the supernatant was run through a Ni-NTA column. The column was washed with binding buffer, and bound protein was released with elution buffer [100 mM Tris-HCl, 500 mM NaCl, 500 mM imidazole, pH 7.5]. As a control, a parallel purification was performed for an empty pRSET-A vector.

In-Vitro Assay for GGP1 Activity with the Standard Substrate GPNA

In vitro assays were assembled with 200 pg of crude protein extract from a cleared E. coli lysate (before column purification) in 0.1 M Tris-HCl at pH 7.5 to a total volume of 150 μl. Assay is initiated by addition of GPNA to a final concentration of 1 mM and enzyme activity is measured by absorbance at 405 nm. Absorbance was measured with 5 minute intervals from time 0-20 minutes using a spectrophotometer.

In-Vitro Assay for GGP1 Activity with GS-X 200 ng of purified GGP1 or 200 ng of control protein were assayed in a final volume of 100 μL containing 20 mM Tris-HCl pH 7.5 and 20 μM GS-X. The reactions were stopped after 10 min upon addition of 300 μL methanol. After an overnight incubation at −20° C., the mixture was spun down for 20 min at 5 000 g and 200 μL of the supernatant were evaporated and redisolved in 50 μL of 75% methanol. Analysis was performed using the LC-MS/MS method previously described. For the determination of $K_m$, similar assays were performed using a range of GS-X concentrations spanning from 10 to 90 μM. The linearity of the assay using 10 μM GS-X was confirmed both with respect to time and amount of protein. The $K_m$ value was inferred from the hyperbolic curve (single, rectangular) that the data was fitted to using Sigma Plot.

Example 1

Reconstitution of Chain Elongated MET Biosynthesis in N. benthamiana

Co-Expression Analysis

Five distinct activities are required to elongate MET to DHM, however, not all of these activities have been characterized.

CYP79F1 and CYP83A1 were used as query sequences in the AttedII co-expression database.

TABLE 3 results of co-expression analysis

| gene | locus | Abbreviation |
|---|---|---|
| Branched chain amino transferase 4 | At3g19710 [1, 2] | BCAT4 |
| Branched chain amino transferase 3 | At3g49680 [1, 2] | BCAT3 |
| MAM1 | At5g23010 [1, 2] | MAM1 |
| Aconitase | At2g43100 [1] | AC |
| Aconitase | At3g58990 [1] | AC |
| Isopropylmalate dehydrogenase | At1g31180 [1] | IPMDH |
| Methylthioalkyl α-ketoacid chloroplastidic transporter - MAC-transporter | At4g12030 [1] | MAC-T |
| CYP79F1 | At1g16410 [2, 3] | CYP79F1 |
| CYP83A1 | At4g13770 [2, 3] | CYP83A1 |
| γ-glutamyl peptidase | At4g30530 [3] | GGP1 |
| Glutathione-S-transferase 11 | At3g03190 [3] | GSTF11 |
| Sulfotransferase | At1g74090 [2, 3] | ST |
| UDP-glucoronysyl transferase | At2g31790 [2, 3] | GT |
| Superroot1 | At2g20610 [2, 3] | SUR1 |
| Flavin-containing monooxygenase | At1g65860 (SEQ ID NO: 95) [2, 4] | FMO |

The following candidates for the chain elongation machinery were identified: BCAT3, BCAT4, MAM1, two aconitases, and a methylthioalkyl α-ketoacid chloroplastidic transporter that may be required for transport of METs/α-ketoacids in/out of the chloroplast. A 3-isopropylmalate dehydrogenase was found using a previous version of AttedII, but removed from the database in the recent edition due to suspected crosshybridization to a homologous probe. Genes used in this study to reconstitute the chain-elongation pathway are marked [1]. Previously characterized genes are marked [2].

Following candidates for enzymes required for conversion of DHM to 4-MSB were identified: CYP83A1, ATGSTF11, a sulfotransferase, an UDP-glucoronosyl transferase, and SUR1. Due to a very high identity to CYP79F2, CYP79F1 is not included in the current dataset used in AttedII. A previous version of AttedII showed a very high expression correlation of 0.82 between CYP79F1 and CYP83A1. Genes used in this study are marked [3]. Previously published genes are marked [2].

Furthermore, a potential γ-glutamyl peptidase, At4g30530, which strongly co-expresses with SUR1, results in increased production of benzylglucosinolate when expressed together with the benzylglucosinolate biosynthetic genes, and was therefore included in the 4-MSB/4-MTB study. An FMO previously shown to catalyze 4-MSB formation from 4-MTB was also found (marked [4]).

Reconstitution of Chain Elongation Pathway

Several combinations of these genes were arranged in multi-gene open reading frames separated by 2A auto-proteolytic sequences and infiltrated into *N. benthamiana* through transient *A. tumefaciens* mediated transformation (FIG. 12). Total extracts from plants harboring constructs 3 and 4 analyzed by LC-MS showed a new peak at 7.1 min with a dominant m/z ratio of 178, characteristics of a corresponding DHM standard (FIG. 8). This peak was absent in wildtype plants and in plants transformed with the P19 suppressor strain alone, and shows that DHM is produced.

A trace of the shorter chain-elongated homo-methionine was detected at 5.5 min, but no traces of longer chain-elongated METs could be detected (data not shown).

Of the oxo-acid intermediates, 2-oxo-6-methylthiohexanoic acid (2o6) could be detected at 14.9 min as a m/z ratio of 177, co-migrating with an authentic standard. It is unclear if the shorter oxo-acids accumulate as a peak of the same m/z ratio and retention time as 2-oxo-5-methylthiopentanoic acid (2o5) was found in both wild type and plants producing DHM and as no trace of 2-oxo-4-methylthiobutanoic acid (2o4) could be detected (data not shown). The dicarboxylic acid intermediates could not be detected.

Although C3 and C4 (FIG. 12) were sufficient to produce DHM, the levels could be significantly increased by combining several constructs with what would appear to be redundant functions.

TABLE 4

DMH and 2o6 concentrations in selected construct combinations.

| Genes | DHM (nmol/g fresh weight) |
|---|---|
| AC1, AC2, IPM | ND |
| AC1, AC2, IPM, BCAT3 | ND |
| BCAT4, MAM1 | ND |
| cpBCAT4, MAM1 | 0.056 ± 0.043 |
| BCAT4, MAM1, AC1, AC2, IPM | 0.77 ± 0.37 |
| cpBCAT4, MAM1, AC1, AC2, IPM | 53.6 ± 14.4 |
| BCAT4, MAM1, AC1, AC2, IPM, BCAT3 | 0.89 ± 0.31 |
| cpBCAT4, MAM1, AC1, AC2, IPM, BCAT3 | 54.6 ± 7.94 |
| cpBCAT4, MAM1, AC1, IPM | 7.04 ± 3.52 |
| cpBCAT4, MAM1, AC2, IPM | 51.4 ± 20.8 |
| cpBCAT4, MAM1, AC1, AC2 | 18.3 ± 8.21 |
| C1, C2, C9 | 349 ± 88.9 |
| C1, C2 | 221 ± 101 |
| cpBCAT4, MAM1, AC2, IPM, CYP79F1, CYP83A1, SUR1, GGP1, GSTF11, UGT74C1, AtST5b | ND |

As can be seen from the Table, although the MAC-T is not required for DHM biosynthesis, it does have a substantial positive effect on the accumulation of said compound.

For example, C1+C2 and C2+C9, were capable of producing low levels of DHM, with significant levels of 2o6 as a side product for C2+C9, but when the three constructs were used simultaneously, the levels of DHM increased approximately 30-fold and only minor quantities of 2o6 was produced. C1 alone was sufficient to produce trace amounts of both DHM and 206. This indicates that *N. benthamiana* harbors endogenous enzymes with aconitase- and isopropyl malate dehydrogenase activities and suggests that 2o6 can be aminated either by BCAT4 or an endogenous *N. benthamiana* activity. However, the levels of both DHM and 206 in this case were marginal and to produce meaningful quantities of DHM, the IPMDH, MAC-T, and either of the aconitases are required in addition to BCAT4 and MAM1.

Example 2

Reconstitution of Aliphatic GSL Biosynthesis in *N. benthamiana*

Figure 9A:
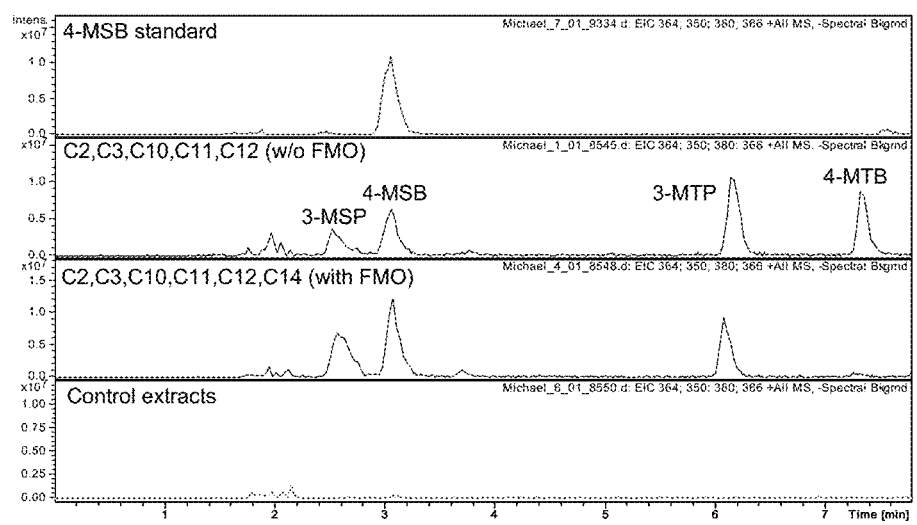

Constructs sufficient to produce DHM (see Example above) were co-infiltrated into *N. benthamiana* with constructs C10, C11, C12, with or without C14, which contains the FMO-gene. Glucosinolates were extracted and analyzed as their desulpho-derivatives by LC-MS. Peak with dominant ions of m/z ratios 350, 364, 366 and 380, respectively, corresponding to the $Na^+$-adduct of the desulphoderivatives of 3-MTP, 4-MTB, 3-MSP and 4-MSB, respectively, were identified (FIG. 9a). This shows production of the expected chain-elongated MET-derived glucosinolates. Furthermore, this shows successful reconstitution of the glucosinolate biosynthetic pathway, leading to 4-MSB.

When C14 was omitted from the infiltration mixture an approximately 50-50 ratio of 4-MTB/4-MSB was found, which indicates that *N. benthamiana* contains an endogenous activity that can oxidize 4-MTB in analogous fashion to the FMO.

The current data shows that it is possible to co-infiltrate at least seven different Aagrobacterium strains into *N. benthamina* at the same time, but as many as ten different strains have been used at the same time successfully (data not shown). This suggests that pathways containing even more genes could be reconstituted in this way.

Figure 9B:
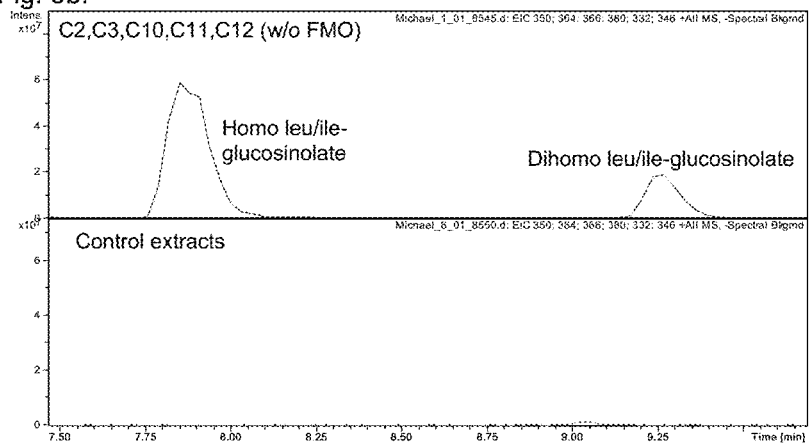

Further analysis of the glucosinolate-extracts and total-extracts revealed that in addition to the MET-derived glucosinolates, additional amino acids and glucosinolates were produced (FIG. 9b).

The amino acids appeared to be chain-elongated versions of leucine and/or isoleucine, i.e. homo-leucine/homo-isoleucine and dihomo-leucine/dihomo-isoleucine. However due to the same mass of leucine and isoleucine, it was not possible to distinguish between them.

The production of these chain-elongated leu/ile-derived amino acids in the present invention is consistent with the findings, albeit in a different context, that they accumulate when MAM1 is expressed from the 35S-promoter. The production of the corresponding glucosinolates has not been reported previously.

These glucosinolates and amino acids do not accumulate naturally in *Arabidopsis*. If it were desired to reduce or eliminate biosynthesis of these compounds in embodiments of the present invention (i.e. to enrich for 4-MSB) MAM1 could be expressed from a weaker promoter, such as the endogenous promoter, or MAM1 could be modified to alter the substrate specificity.

Example 3

Reconstitution of Aromatic GSL Biosynthesis in *N. benthamiana*

Production of Benzylglucosinolate (BGSL) in *N. benthamiana*

Different combinations of *Agrobacterium* strains individually containing constructs C15-17 (FIG. 1) were used to transiently transform *N. benthamiana* leaves. Whole leaves were harvested 7 or 8 days post infiltration (dpi) and analyzed for glucosinolates. Co-infiltration of C16 and C17, which carry altogether CYP79A2, CYP83B1 and SUR1, was sufficient to produce detectable amounts of BGSL, which reached an average of 0.6 μmol/mg fresh weight at 8 dpi. However, BGSL production was significantly increased when UGT74B1 and AtST5a were included by using construct combination C15+C17. Neither C15 nor C17 were capable of driving production of BGSL on their own at 7 dpi, whereas leaves infiltrated with the combination reached an average of 31.5 μmol/mg fresh weight at the same time point. Representative chromatograms are shown in FIG. 2.

BGSL Accumulates Stably in Transiently Transformed *N. benthamiana*

The production of BGSL in *N. benthamiana* leaves was monitored over time using plants transformed with the C15+C17 combination (FIG. 1). Infiltrated leaves were harvested and analyzed for glucosinolates at 5 different timepoints spanning 2-10 dpi. From 10 dpi and on, infiltrated leaves started wilting regardless of the construct combination used (including negative control leaves), which made quantification difficult. BGSL could be detected at 2 dpi, and accumulated through the entire study. The accumulation fitted a second order line ($R^2=0.996$) with no indication of saturation at 10 dpi (results not shown), showing that BGSL can accumulate stably in a heterologous host.

Example 4

GGP1: A Newly Characterised Gene Involved in GSL Biosynthesis

Identification of At4g30530 (GGP1) as a Candidate Gene for a Gamma-Glutamyl Cleaving Enzyme in the Biosynthesis of GSLs The comprehensive systems biology database, which is based on publicly available microarray expression data, was used to select genes that were co-regulated along with both the *Arabidopsis* genes CYP83B1 (At4g31500) and SUR1 (At2g20610, coding for the only known C—S lyase in the GSL pathway).

From the selected genes, At4g30530 coded for an unknown protein. This gene encoded a glutamine amidotransferase class-I domain. Glutamine amidotransferases are enzymatic subunits that can produce ammonia from glutamine, which can also be described as gamma-glutamylammonia (Massiere and Badet-Denisot, 1998).

Co-Expression of GGP1 Increases BGSL Production in *N. benthamiana*

The effect of GGP1 on BGSL biosynthesis in *N. benthamiana* was analyzed, and the results are presented in FIG. 3. When compared to combination C15+C17 (carrying five genes altogether), combination C15+18 (carrying five genes plus GGP1) boosted BGSL production almost seven-fold, reaching an average of 0.213 nmol/mg fresh weight at 7 dpi.

BGSL production was also observed in plants harboring C18 alone, demonstrating that BGSL production is also possible with CYP79A2, CYP83B1 and GGP1. It is remarkable that C18 alone is able to drive production of BGSL to a similar extent as the C15+17 combination, suggesting that in heterologous systems, the activity conferred by GGP1 is more crucial than the one conferred by SUR1 (see Example 3).

GGP1 Abolishes the Accumulation of Glutathione-Conjugate (GS-X) in BGSL-Producing *N. benthamiana* Plants Total methanol extracts of *N. benthamiana* leaves infiltrated with either C15+C17, C15+C18, C18 alone, or a control construct (p19) were analyzed by LC-MS. Plants infiltrated with C15+C17 (five genes altogether, without GGP1) displayed a major novel peak with an m/z ratio of 441. The peak was absent in control plants, co-migrated with synthesized glutathione-conjugate (GS-X), and presented similar MS fragmentation patterns that synthetic GS-X (results not shown). This shows that substantial amounts of precursor molecules for BGSL are not efficiently shuttled through the metabolic pathway, but accumulate as GS-X. This suggests additional enzyme activities can optimize BGSL production. Interestingly, plants infiltrated with C15+C18 (five genes plus GGP1) do not show any trace of GS-X. Furthermore, the GS-X peak was likewise absent from plants infiltrated with only C18 (data not shown), demonstrating that the activity of GGP1 is independent of the remaining biosynthetic enzymes.

The Effects of GGP1 in the Production of BGSL Over Time

Figure 13:
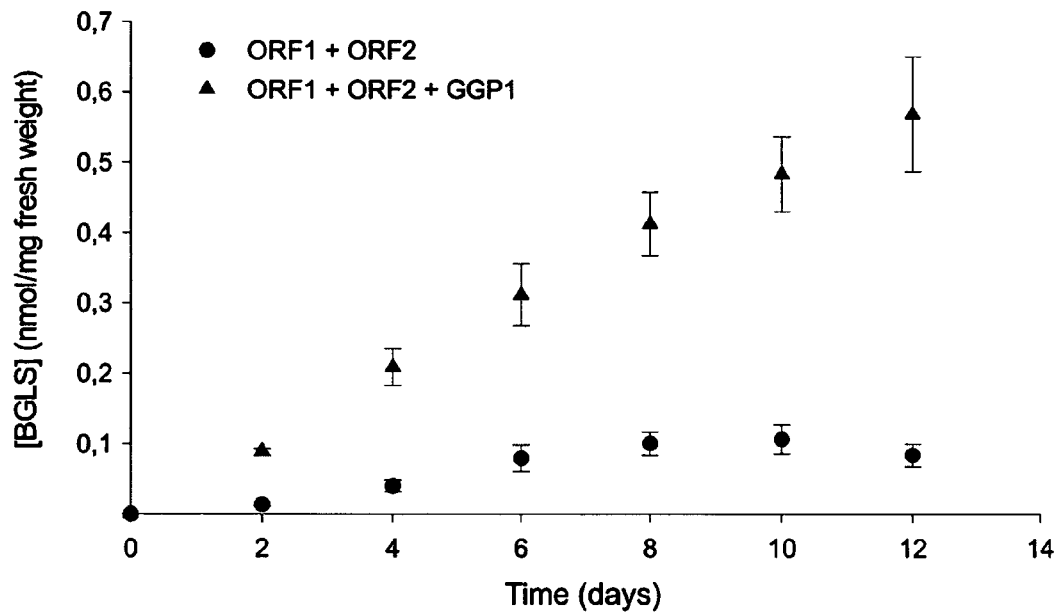
Figure 13:
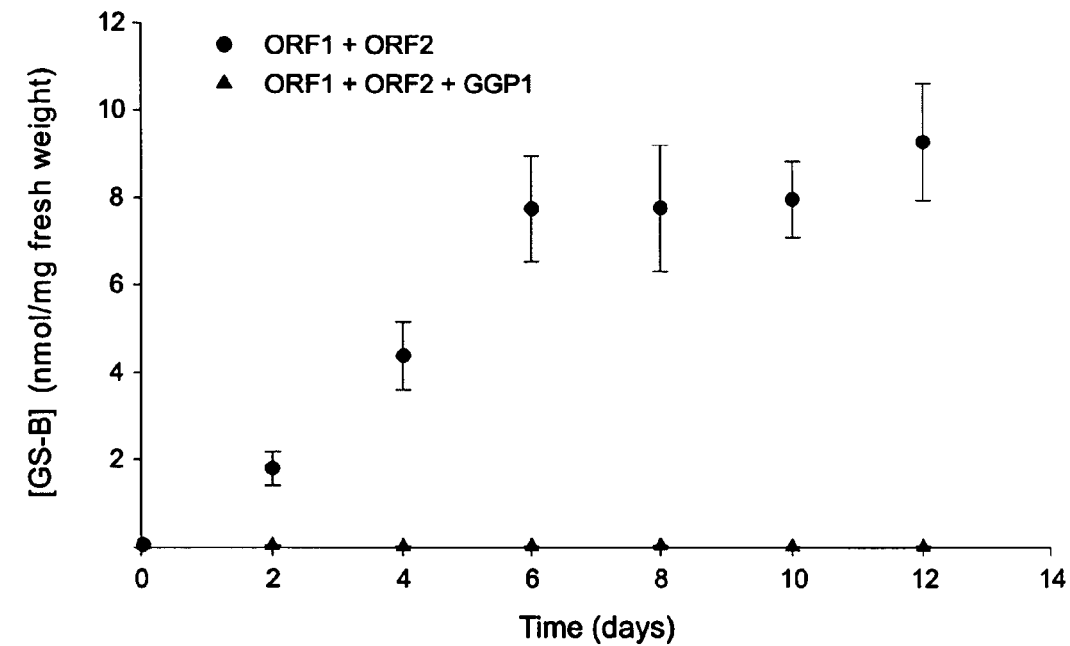
Figure 14:
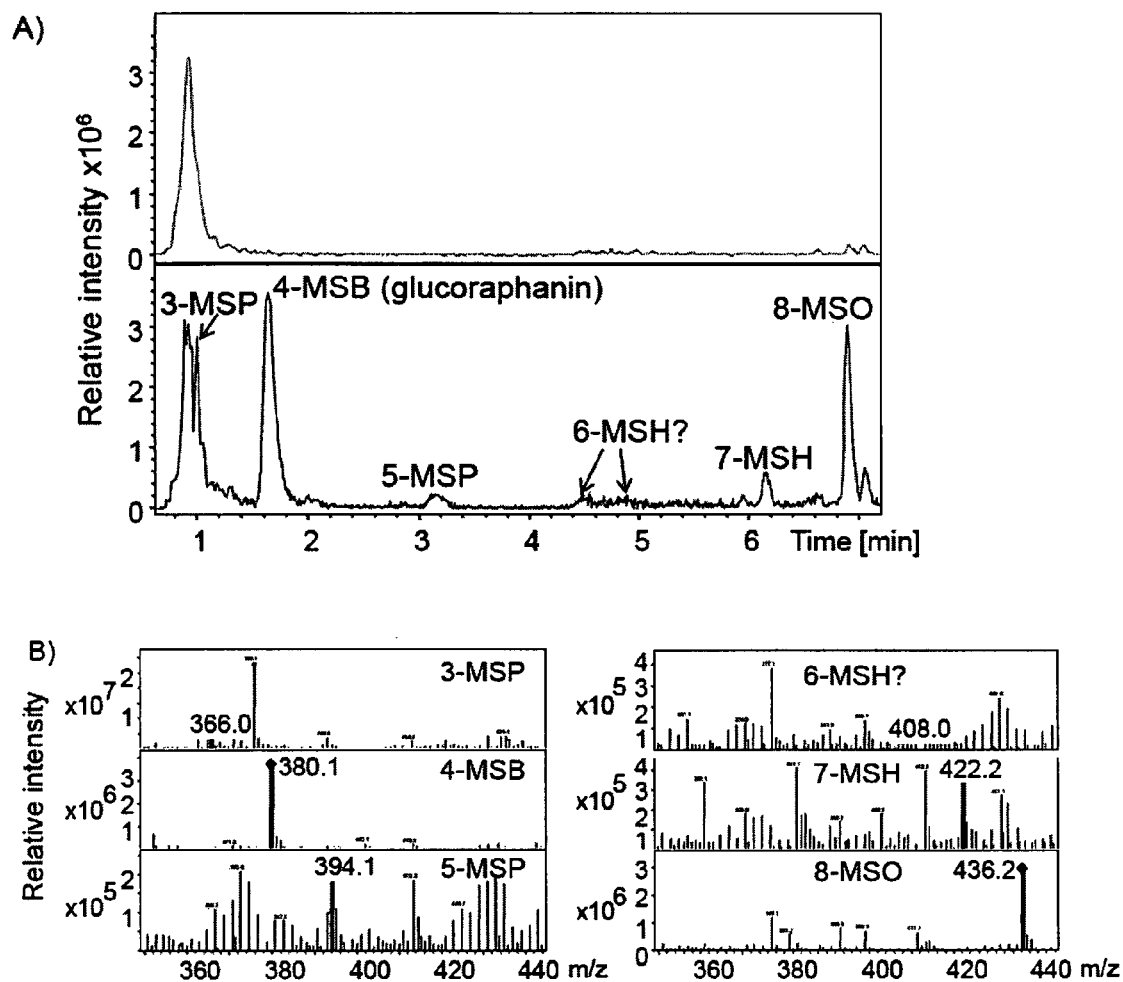
Figure 15:
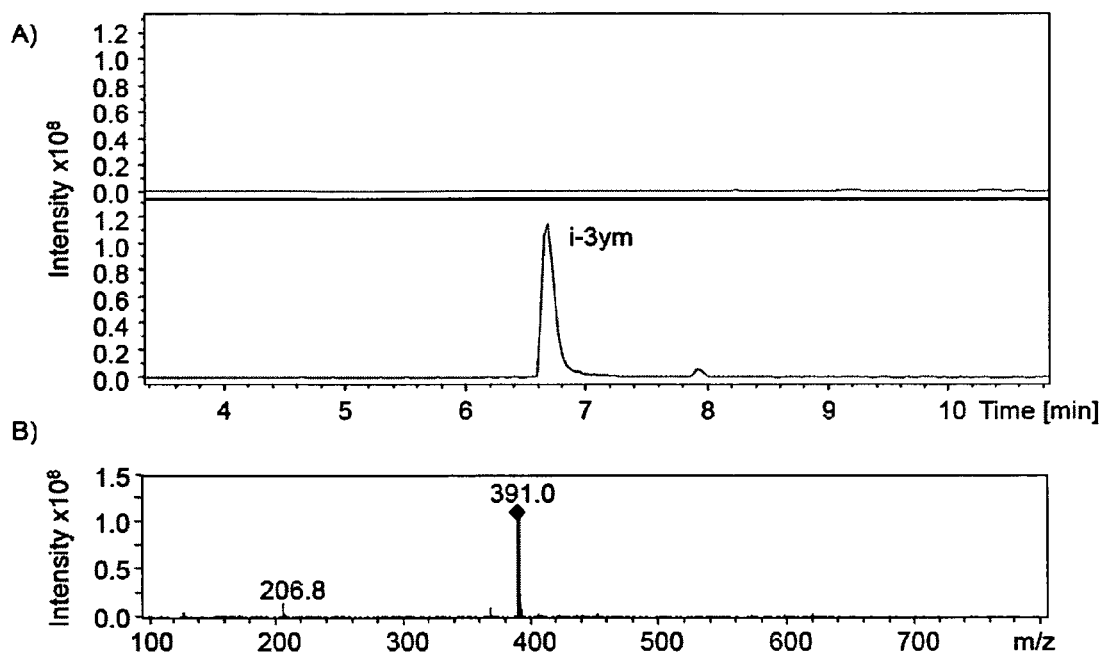
Figure 16:
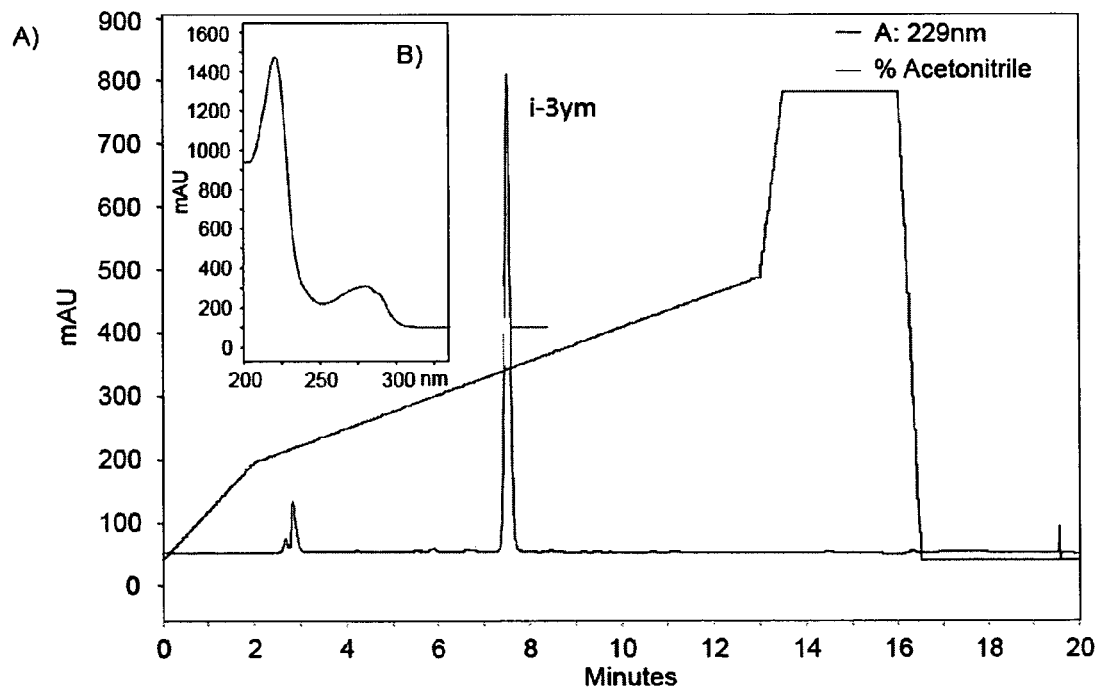
Figure 17:
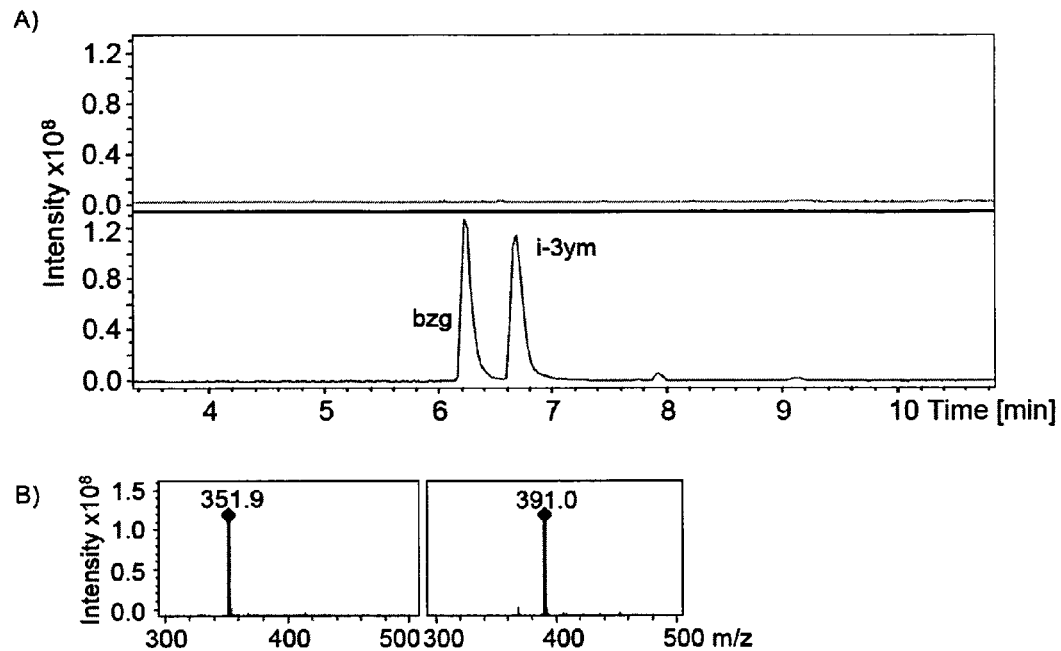

The effect of GGP1 in the production of BGSL over time was assessed using constructs C15 and C17 as basic construct mixture (5 genes altogether) in the presence or absence of C19, which carries only GGP1. The accumulation of BGSL and GS-X was measured for each case at 7 evenly spaced time points from 0 to 12 dpi. At all time points, the presence of GGP1 increased BGSL accumulation several fold and decreased GS-X accumulation drastically (FIG. 13).

GGP1 Recombinant Protein is Able to Cleave Gamma-Glutamyl Residues

Recombinant GGP1 was expressed in *E. coli*, purified (FIG. 4a) and incubated with GS-B in vitro. LC-MS/MS analysis of reaction mixtures revealed conversion of GS-X to the expected product (FIG. 4c), which was analyzed as its derivative, 'cyclized Cys-Gly-X'(FIG. 4b). This demonstrated that GGP1 hydrolyzes the gamma-glutamyl peptide bond in GS-B. The $K_m$ value was determined to be $57\pm19$ μM (SE, FIG. 4d), which demonstrates that GGP1 has high affinity for GS-X. Furthermore, FIG. 5 shows that the protein is also able to cleave the analogous residue of GPNA, which is not related to glucosinolate biosynthesis. Therefore, the biotechnological potential of GGP1 and GGP1 homologs is not restricted to glucosinolate biosynthesis.

Sequence Comparison and Expression Analysis of the GGP1 Gene Family in *Arabidopsis*

Members of the GGP family in *Arabidopsis* were identified based on sequence similarity. Four homologues of GGP1 (At4g30530) were identified: At4g30540, At4g30550, At2g23960, and At2g23970. The five protein sequences were pairwise aligned, and the relative percentages of identity are shown in FIG. 6. Alignments were made with either the clustalW (lower left diagonal) or the BLASTp (upper right diagonal) algorithms. All members of the family are highly conserved within *A. thaliana*.

According to the Gene Atlas from Genevestigator, At4g30540 is not expressed above microarray threshold levels in any part of the plant. At2g23960 only presents detectable expression in the radicle and in roots, whereas At2g23970 only does so in the stamens. In contrast, both GGP1 and At4g30550 are expressed throughout the different plant parts. However, only GGP1 presents an expression pattern (in different plant organs) that highly resembles the expression patterns of genes involved in glucosinolate biosynthesis, like CYP83B1 (At4g31500), SUR1 (At2g20610), UGT74B1 (At1g24100), and AtSOT16 (At1g74100).

Phylogenetic Comparison of the GGP and GGT Families

In plants, prior to the discovery of GGP1, cleavage of gamma-glutamyl peptide bonds was restricted to enzymes of a single family, the gamma-glutamyl transpeptidases (GGTs). One member of the GGT family, GGT3, has been reported to cleave gamma-glutamyl peptide bonds in glutathione conjugates of xenobiotics in the vacuole (Ohkama-Ohtsu et al, 2007). Amino acid sequences of GGT3 and GGP1 were compared by pairwise alignment, and homologous sequences from *Arabidopsis*, other *brassica* species and rice (*Oryza sativa*) were selected. Since no close homology was evident between GGT3 and GGP1, separate phylogenetic trees for the two families were constructed (FIG. 7). It is evident from the phylogenetic tree of the GGTs that members from *Arabidopsis* have close relatives in rice (i.e. they group together in clades). In contrast, the phylogenetic tree of the GGP family shows close relatives between *Arabidopsis* and other *Brassica* species, but not between *Arabidopsis* and rice (i.e. they correspond to different clades). This suggests that GGPs might have a *Brassica* specific function, which could be glucosinolate biosynthesis.

Sulfur Donation in the Core Biosynthesis of GSLs: A New Theory

The biosynthesis of GSLs from amino acids (core biosynthesis) involves two different cytochrome p450s (from the CYP79 and CYP83 families, respectively), a C—S lyase, a glucosyltransferase (GT) and a sulfotransferase (ST), in that order. After the CYP83 reaction, which produces an unstable intermediate, conjugation to a thiol occurs.

It was previously speculated that this thiol is cysteine (CYS), and that the conjugation happened either non-enzymatically or aided by a glutathione-S-transferase (GST) (Hansen et al., 2001). Conjugation of CYS by a GST is unprecedented and seemed unlikely, given that these families of enzymes posses a highly conserved binding domain for glutathione (and not Cys). Non-enzymatic conjugation of CYS seemed unlikely also, since the product of CYP83 is released in the cytosol, where the major thiol is GSH and not CYS.

Therefore, we speculated that incorporation of reduced sulfur into glucosinolates proceeds through a glutathione-conjugate intermediate (GS-X), and that the conjugation reaction happens either non-enzymatically or assisted by a GST. Cytosolic concentrations of GSH range from 3 to 10 mM (Leustek and Saito, 1999), and non-enzymatic conjugation of GSH to the product of CYP83B1 has been shown to occur in vitro at these concentrations (Bak and Feyereisen, 2001)

Regardless of the mechanism of glutathione conjugation, further enzymatic activities would be required to convert GS-X to a chemical compound that can serve as a substrate for the C—S lyase, which is the next enzyme in the pathway. C—S lyases possess a PLP co-factor used actively in catalysis (Bertoldi et al., 2002). The PLP cofactor binds the substrate through the substrate's alpha-amino group (Bertoldi et al., 2002), which is chemically modified in the case of GSH. Cleavage of the gamma-glutamyl residue of GSH would produce the necessary free alpha-amino group so that the rest of the biosynthesis can take place.

Example 5

Reconstitution of GSL in a Microorganism

Linear expression constructs of biosynthetic cDNAs encoding for biosynthetic activities in GSL biosynthesis are generated. For formation of chain-elongated MET, this includes amino acid transferase activity e.g. by BCAT4 or functional homologues, a condensation activity e.g. by MAM1 or functional homologues thereof, isomerization activities e.g. by aconitase 1 or functional homologues thereof, oxidative decarboxylation activities e.g. by IPMDH or functional homologues thereof, transaminase activities e.g. by BCAT3 or functional homologues thereof, and transporter activities e.g. by MAC-T or functional homologues thereof (see table 3). Targetting signal peptides may be included or excluded from the cDNAs.

For formation of MET-derived GSL, the activities include N-hydroxylating enzyme activities e.g. in the form of CYP79F1 or functional homologues thereof, oxime oxidation activities by e.g. CYP83A1 or functional homologues thereof, a GST activity e.g. by GSTF11 or functional homologues thereof, gamma glutamyl peptidase activity by e.g. GGP1 or functional homologues thereof, C—S lyase activity by SUR1 or functional homologues thereof, glucosyltransferase activity by UGT74B1 or functional homologues thereof, sulfotransferase activity by AtST5b or functional homologues thereof, and a S-oxygenating flavin monooxygease activity by $FMO_{GSOX1}$ or functional homologues thereof.

As electron donor to the cytochromes P450 may be included e.g. a NADPH cytochrome P450 reductase (At4g24520, NM_118585) or functional homologues thereof. Alternative electron donors may be cytochrome b5 (At2g46650, NM_130230.2, NP_182188.1) and NADH cytochrome b5 reductase (AT5G17770, NM_121783.4, NP_197279.1), or functional homologues thereof.

For aromatic GSL, activities which are introduced include N-hydroxylating enzyme activities e.g. in the form of CYP79A2 (for BGSL), CYP79A1 (for tyrosine-derived p-hydroxybenzyl GSL (pOHBGSL)), CYP79B2 (for indole GSL) or functional homologues thereof, oxime oxidation activities by e.g. CYP83B1 or functional homologues thereof, a GST activity e.g. by GSTF11 or functional homologues thereof, gamma glutamyl peptidase activity by e.g. GGP1 or functional homologues thereof, C—S lyase activity by SUR1 or functional homologues thereof, glucosyltransferase activity by UGT74B1 or functional homologues thereof, and sulfotransferase activity by AtST5a or functional homologues thereof. As electron donor to the cytochromes P450 is included e.g. a NADPH cytochrome P450 reductase (At4g24520, NM_118585) or functional homologues thereof.

Linear DNA fragments with expression constructs of biosynthetic cDNAs are driven by a yeast constitutive promoter (e.g. TPII) or a yeast inducible promoter (e.g. GAL1) surrounded by flanking sequences that are identical to chromosomal yeast DNA. The heterologous DNA is iteratively transformed into the yeast strain e.g. isogenic strains to CEN.PK113-7D using appropriate genetic markers well known in the art (e.g. URA3) to screen for stable integration of the genes into the yeast genome on selected medium. Cultures are grown at 28C in YEP media. Yeast cells are harvested by centrifugation in 10 min at 5000 g. Extraction of glucosinolates is as described in examples 1 and 2. Glucosinolate analysis is performed as described in Hansen et al. (2007). Metabolite profiling is carried out by analytical LC-MS on crude cleared methanolic extracts.

Constructs sufficient to produce, respectively, glucoraphanin via DHM and BGSL pOH-BGSL or indole GSL are transformed into yeast. Glucosinolates are extracted and analyzed as desulfoglucosinolates. Peaks corresponding to the $Na^+$ adduct of the desulfo derivative of S-MTP, 4-MTB, 3-MSP, 4-MSB or, respectively, BGSL, pOH-BGSL and indole GSL are found.

Example 6

Production of Stable Transgenic Plants

Constructs for Constitutive Expression in Planta

To construct 35S overexpression constructs, PCR is performed with PfuTurbo® $C_x$ Hotstart DNA polymerase on full-length-cDNA-containing clones with deoxyuridine-containing primers. The PCR products are cloned into pCAMBIA230035Su (Nour-Eldin et al., 2006) using the method described therein.

Plant Transformation.

The constructs are transformed into *A. tumefaciens* strain C58C1(Shen and Forde, 1989; Zambryski et al., 1983) and into *A. thaliana* Col-0 by *A. tumefaciens*-mediated plant transformation using the floral dip method (Clough and Bent, 1998). Transgenic plants are selected on 50 µg/ml kanamycin ½ MS plates.

Cabbage and oil-seed rape may be transformed by previously described methods (Moloney et al., (1989) Plant Cell Rep. 8, 238-242) likewise pea (Bean et al., (1997) Plant Cell Rep. 16, 513-519), potato (Edwards et al., (1995) Plant J. 8, 283-294) and tobacco (Guerineau et al., (1990) Plant Mol. Biol. 15, 127-136).

Plant Growth Conditions:

Surface-sterilized seeds are sown on 0.5×MS plates containing 50 pg/ml kanamycin and kept in darkness at 5 degrees for two days before transferal to growth chambers (HEMZ 20/240/S, Heraeus) at a photosynthetic flux of 100 µE at 20° C. and 70% relative humidity at a 16 h photoperiod. After 12-14 days on plates, the plants are transferred to a soil:vermiculite (10:1) mixture wetted with Bactimos L (Garta, Copenhagen, DK).

Example 7

Use of GGP-Encoding Genes as a Marker for Marker-Assisted Breeding Programmes

A complete or part of GGP-encoding gene nucleotide sequence is used as a DNA probe to identify restriction fragment length polymorphisms or other markers occurring between plant breeding lines of *Brassica* and other GSL-producing taxa, which possess different GGP-encoding alleles using conventional sequence analysis techniques—see e.g. Sorrells & Wilson (1997) *Crop Science* 37: 691-697.

A complete GGP-encoding gene nucleotide sequence or part thereof may be used to identify the homologous genomic sequence within various Capparales species as discussed above, and these may likewise be used to generate markers for the relevant species.

Primers are designed to amplify PCR products of different sizes from plant breeding lines containing different alleles. CAPS markers are developed by restricting amplified PCR products. In order to ensure there is no recombination within the relevant genes during crossing, typically a marker within the gene as well as two markers flanking each side of the gene will be assessed.

The markers are used in *Brassica* breeding programmes aimed at manipulating GSL content of the plants. These DNA markers are then used to rapidly screen progeny from a number of diverse breeding designs, e.g. backcrosses, intercrosses, recombinant inbred lines, for their genotype surrounding the GGP loci. The use of DNA markers within and linked to the GGP-encoding genes allows the rapid identification of individuals with the desired genotype without requiring phenotyping.

Example 8

Reconstitution of Long-Chain Aliphatic GSL Biosynthesis in *N. benthamiana*

Several long-chain aliphatic sulfinyl-glucosinolates ($C_7$ and $C_8$) have been shown to possess cancer-preventive properties in human nutrition. However, the extremely complex biosynthesis of these compounds, which involves as many as 32 intermediates, would make conventional chemical synthetic production of these compounds for use in e.g. intervention studies all but impossible using existing technologies.

This Example demonstrates the reconstitution of the biosynthetic pathway resulting in production of the cancer-preventive S-oxygenated sulfinyl-derivatives of both short-chain ($C_3$ and $C_4$) and long chain ($C_7$ and $C_8$) GSLs.

Cloning

MAM3 (NM_12208.3, NP_19769.3) was cloned from *Arabidopsis* (Col-0) cDNA using the Hotmaster polymerase and the primers ACAATTTCCCCACTATCTATCCTC (SEQ ID NO: 81) and TTTCCAATACTTTGGTGAAAATCA (SEQ ID NO: 82). PCR was performed using the CX-pfu polymerase and the following primers:

```
BCAT4:
GGCTTAAUGAATTCATGGCTCCTTCTGCGCA (SEQ ID NO: 23)
and

ACATCTCCUGCCAACTTAAGCAAATCAAAATTCAAAGTTTGACCAGAACC
GCCCTGGCGGTCAATC  (SEQ ID NO: 83),

MAM3:
AGGAGATGUGGAATCTAACCCAGGACCTATGGCTTCGTTACTTCTCACAT
(SEQ ID NO: 84) and

GGTTTAAUCTCGAGCTATCATACAACAGCGGAAATCTGAGG
(SEQ ID NO: 85).
```

The corresponding PCR fragments were purified and mixed to produce a BCAT4+MAM3 construct in the MP27 vector by USER-fusion based cloning as previously described (Gey-Flores et al., 2007) and sequenced. Positive clones were sequenced and transformed into *Agrobacterium tumefaciens* strain C58 by electroporation.

Production of the remaining genes and constructs used has been described previously (Mikkelsen et al., 2008).

Infiltration of *Nicotiana benthamiana*

*A. tumifaciens* cultures were grown at 28° C. in YEP media with 50 mg $L^{-1}$ Kanamycin and 34 mg $L^{-1}$ Rifampicilin. Cells were harvested by centrifugation, 10 minutes at 3000 g, and resuspended to a final OD of 0.75 in 10 mM MES buffer with 10 mM $MgCl_2$ and 100 µM Acetosyringone. Following a 150 minutes shaking incubation, 50 rpm at room temperature, the *A. tumefaciens* strains were mixed in roughly equimolar amounts and approximately one-quarter volume of the P19 suppressor-strain (Voinnet et al., 2003) was added. The *A. tumefaciens* were injected into the leaves of three-four weeks old *N. benthamiana* plants using a 1 mL syringe.

The constructs used were previously described for glucoraphanin (4-MSB) biosynthesis, except that MAM1 was substituted with MAM3 and the FMO was substituted with $FMO_{GS-OX5}$.

Glucosinolate Analysis

Glucosinolates were extracted by applying the total extract on a Sephadex DEAE A25 column, washed with 85% methanol, water, desulphonated with a *Helix pomatia* sulfatase and eluted with water. The resulting desulphoglucosinolates were analyzed by LC-MS as described previously (Mikkelsen and Halkier, 2003).

Results

*A. tumefaciens* strains harboring the following genes: BCAT4, MAM3, AC1, AC2, IPMDH, MAC-T, cBCAT4, CYP79F1, CYP83A1, GSTF11, SUR1, GGP1, UGT74C1, AtST5b and $FMO_{GS-OX5}$, were co-infiltrated into *N. benthamiana*. After seven days, glucosinolates were extracted and analyzed as their desulpho-glucosinolate derivatives by LC-MS. This identified at least five peaks not found in controls (FIG. 1). The peaks had [M+Na$^+$]=364, 380, 394, 422 and 436 corresponding to 3-methyl sulfinyl propyl GSL (3-SMP), 4-methyl sulfinyl butyl GSL (4-MSB), 5-methyl sulfinyl pentyl GSL (5-MSP), 7-methyl sulfinyl heptyl GSL (7-MSH) and 8-methyl sulfinyl octyl GSL (8-MSO), respectively. The ratios of these GSLs were similar to those found in *Arabidopsis* (Col-0), with highest amounts of 4-MSB, 8-MSO, lower amounts of 7-MSH and trace amounts of 5-MSP and 3-MSP. 6-methyl sulfinyl hexyl GSL could not be reliably detected.

Example 9

Reconstitution of Indole-3-Yl-Methyl Glucosinolate Biosynthesis in *Nicotiana benthamiana*

Introduction

Indole-3-yl-methyl glucosinolate (I3G) is a plant defense compound derived from tryptophan (for review see Halkier and Gershenzon, 2006). It is strongly induced by jasmonates (Mikkelsen et al., 2003) and in addition can be modified by CYP81F2 to produce 4-methoxyindole-3-yl-methyl glucosinolate, which has been shown to play a key role in the plant defense against microbes (Bednarek et al., 2009; Clay et al., 2009). Indole-glucosinolates (IGs) in general have also been shown to have beneficial effects in human nutrition and studies are being performed to address this issue (Olsen, 2008).

I3G is produced from tryptophan and is sequentially metabolized by seven enzymes: CYP79B2, CYP83B1, GSTF9, SUR1, GGP1, UGT74B1, AtST5a.

I3G is difficult to obtain. Chemical synthesis is very challenging and expensive. Purification from plants is hampered by either low concentration, or presence of other glucosinolates (GSLs) that are difficult to separate from I3G. Therefore, a source of I3G without the presence of other GSLs would be a great asset for specific intervention studies. Additionally, producing I3G in non-cruciferous plants would be a good tool for studying plant-insect and plant-microbe interaction as well as for studying the plant innate defense. Finally, production of I3G in *Nicotiana benthamina* would be an excellent platform for modifying the produced I3G to give hydroxylated I3M or even methoxylated I3M by using monooxygenases and methyltransferase-coding genes that can be obtained by one skilled in the art in the light of the disclosure herein as desired, for example based on the use of publicly available co-expression database (cf. Examples 11).

Cloning

CYP79B2 (NM_120158.2, NP_195705.1) and CYP83B1 coding sequences were amplified from *Arabidopsis* cDNA with the CX-pfu polymerase to incorporate USER-cloning sequences and 2A auto processing sequences using the following primers:

```
CYP79B2:
GGCTTAAUATGAACACTTTTACCTCAAACTCTTCG
(SEQ ID NO: 86) and

GGTTTAAUTCACTTCACCGTCGGGTAGA
(SEQ ID NO: 87)

CYP83B1:
GGCTTAAUATGGATCTCTTATTGATTATAGCCGGT
(SEQ ID NO: 88) and

GGCTTAAUTCAGATGTGTTTCGTTGGTGC
(SEQ ID NO: 89)
```

Each of the resulting fragments were mixed in approximately equal-molar ratios with the MP27-vector, USER-treated as described previously (Nour-Eldin et al., 2006), and transformed into *E. coli*. Resulting positive clones were sequenced and transformed into *Agrobacterium tumefaciens* strain C58 by electroporation.

Additional gene expression constructs harboring CYP79A2, GSTF9, SUR1, GGP1, AtST5a and UGT74B1 were kindly provided by F. Geu-Flores and M. T. Nielsen. Generation of these constructs was described previously (Geu-Flores et al., in press).

Infiltration of *N. benthamiana*

*A. tumefaciens* cultures were grown at 28° C. in YEP media with 50 mg L$^{-1}$ Kanamycin and 34 mg L$^{-1}$ Rifampicilin. Cells were harvested by centrifugation, 10 minutes at 3000 g, and resuspended to a final OD of 0.75 in 10 mM MES buffer with 10 mM MgCl$_2$ and 100 µM Acetosyringone. Following a 150 minutes shaking incubation, 50 rpm at room temperature, the *A. tumefaciens* strains were mixed in roughly equimolar amounts and approximately one-quarter volume of the P19 suppressor-strain (Voinnet et al., 2003) was added. The *A. tumefaciens* were injected into the leaves of three-four weeks old *N. benthamiana* plants using a 1 mL syringe.

Glucosinolate Analysis

Glucosinolates were extracted by applying the total extract on a Sephadex DEAE A25 column, washed with 85% methanol, water, desulphonated with a *Helix pomatia* sulfatase and eluted with water. The resulting desulphoglucosinolates were analyzed by LC-MS as described previously (Mikkelsen and Halkier, 2003).

Purification of intact I3G

I3G was extracted from *N. benthamiana* by boiling in 85% MeOH. The total MeOH extracts were applied to a Sephadex A-25 column, washed three times with 3:2:5 formic acid:isopropanol:water, four times with water and finally eluted with 0.5M K$_2$SO$_4$/3% isopropanol into an equal volume of EtOH. The supernatant was concentrated in vacuo.

Aliquots were desulphonated using a *H. pomatia* sulfatase and analyzed by HPLC as described previously (Sønderby et al., 2007).

Results

*Agrobacterium tumefaciens* strains containing constructs harboring CYP79B2, CYP83B1, GSTF9+GGP1+SUR1 and AtST5a+UGT74B1 were co-infiltrated into *Nicotiana benthamina* leaves. After seven days of incubation, glucosinolates were extracted and analyzed by LC-MS as their desulpho-glucosinolate derivatives. This identified a single peak of [M+Na$^+$]=391 corresponding to I3G (FIG. 1). The concentration of I3G was approximately 0.2 nmol/mg fresh weight, which is comparable to what has been reported for benzyl glucosinolate (BGSL; 0.213 nmol/mg fresh weight; Geu-Flores et al., in press).

I3G was purified intact from whole leaves of *N. benthamiana*. Approximately 2.5 µmol>95% pure I3G was obtained from a total of three infiltrated leaves in each of five plants (FIG. 2). Theoretically, 75 µmol I3G pr. m$^2$ could be produced, although this number would decrease with increasing number of plants.

Genes encoding the I3G biosynthetic pathway were co-infiltrated into *N. benthamiana* with CYP79A2, which catalyzes the first step in BGSL biosynthesis. The six downstream genes in both I3G and BGSL biosynthesis are identical. LC-MS analysis of desulpho-glucosinolates from plants expressing CYP79A2, CYP79B2 and the remaining GSL biosynthetic genes identified two peaks of [M+Na$^+$]=352 and 391 corresponding to BGSL and I3G, respectively. This shows that it is possible to produce more than one GSL at a time in *N. benthamiana*.

Example 10

Reconstitution of Aromatic GSL Biosynthesis in Stable Transgenic Tobacco Plants

Figure 18:
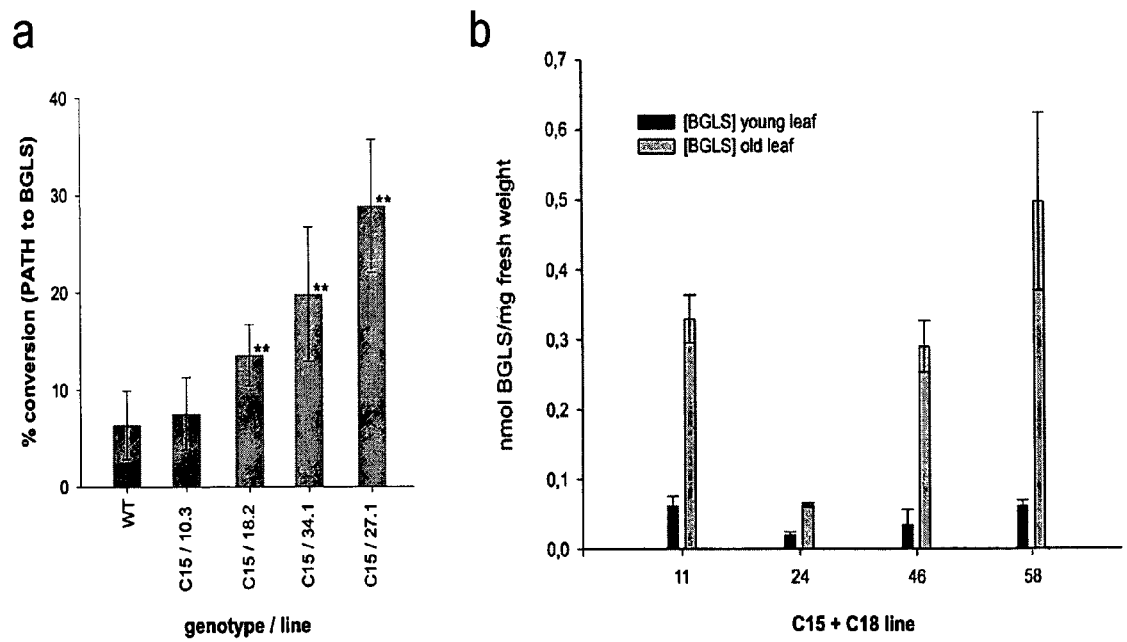

Construct C15 (carrying SUR1, UGT74B1, and AtST5a) was transformed into wildtype tobacco (*N. tabacum* L. cv. *Xanthi*) by *Agrobacterium*-mediated transformation of leaf explants (Horsch et al., 1985). C15 transgenic lines were selected by regenerating transformed explants on growth media containing kanamycin (100 mg/L) and by testing the regenerants for the presence of C15 by PCR on genomic DNA using primers ATGGAATCAAAGACAACCCAA (SEQ ID NO: 90) and GTCTCGTACCTAAGGAACA (SEQ ID NO: 91), which can amplify a fragment of AtST5a. To select the best C15 transgenic line, different lines were fed phenylacetothiohydroxamate (PATH) through cut petioles, and BGSL was analyzed 24 hours later. The line with the highest average PATH-to-BGSL conversion, C15-27.1, was selected for a subsequent transformation with construct 18 (FIG. 18*a*).

Construct C18 (carrying CYP79A2, CYP83B1, and GGP1) was transformed into transgenic line C15-27.1 by *Agrobacterium*-mediated transformation of leaf explants (Horsch et al., 1985). Transformed explants were regenerated in growth media containing both kanamycin (100 mg/L) and phosphinotricin (1.15 mg/L). From ~80 3-month-old regenerated plants, four were shown to contain BGSL in both young and old leaves, with old leaves having more BGSL (FIG. 18*b*). All of the four mentioned transgenic lines, named 11, 24, 46, and 58, were found to contain construct C18 in their genomes, as shown by PCR on genomic DNA using primers GAAGGTTAGCGAAAGGTATCTC (SEQ ID NO: 92) and TGTTTCTTGTTTAGGGCG (SEQ ID NO: 93), which can amplify a fragment of CYP83B1.

Example 11

For the efficient metabolic engineering of GSLs, the co-expression of relevant PAPS biosynthesis and regeneration genes may confer considerable benefits. This is based on the observation that in *Arabidopsis thaliana*, a plant that produces GSLs naturally, these genes are tightly co-regulated with GSL biosynthesis genes (not shown). Furthermore, unlike other co-substrates consumed during the biosynthesis of GSLs (like NADPH or UDP-Glc), PAPS is not considered a primary metabolite, and PAPS levels are unlikely to be regulated stringently. Accordingly, expression of GSL biosynthetic genes without co-expression of PAPS biosynthesis and regeneration genes may cause an accumulation of desulfoGSLs or derivatives of desulfoGSLs because of both a depletion of the PAPS pool (needed for the sulfotransferase reaction) and an accumulation of PAP (which inhibits the sulfotransferase reaction). Furthermore, the utilization of PAPS without the conversion of the byproduct PAP to AMP (and ultimately to ATP) is translated into the consumption of two molecules of ATP per sulfation cycle instead of a single one. Such a difference would be expected to cause an extra energetic burden in a target organism producing GSLs without expressing a PAP bisphosphatase.

Microarray-based co-expression databases have proven powerful for the identification of candidate genes associated to GSL biosynthesis in *Arabidopsis*, as exemplified by the discovery of GGP1 (see Example 4). In order to discover the genes coding for the ATPS and APK enzymes involved in GSL biosynthesis in *Arabidopsis*, a search was performed in the on-line database ATTED-II using SUR1 or CYP83B1 as query. Among the top-24 co-expressed genes for both queries were, in addition to many known GSL biosynthetic genes, ATP sulfurylase 1 (ATPS1, At3g22890), APS kinase 1 (APK1, At2g14750), APS kinase 2 (APK2, At4g39940), and SAL1 (At5g63980). The gene SAL1 is believed to code for the PAP bisphosphatase (Quintero et al. 1996; Gil-Mascarell et al. 1999).

These data were confirmed in another co-expression database, CressExpress, which allows up to 50 genes as query. This enabled a search for genes simultaneously co-expressing with five of the GSL biosynthetic genes, CYP83B1 (At4g31500), GGP1 (At4g30530), SUR1 (At2g20610), UTG74B1 (At1g24100) and AtST5c (At1g18590). Here, the pathway-level co-expression result had APK2 as first hit and APK1 and ATPS1 as hit 4 and 5 respectively, confirming the findings from ATTED-II.

The identified PAPS biosynthesis and regeneration genes code for proteins most probably containing chloroplast target peptides (Table 5).

TABLE 5

Prediction of subcellular localization of PAPS biosynthetic genes. Prediction was done with tools available in Aramemnon

| PAPS genes | AGI code | Gene SEQ ID | Protein SEQ ID | Predicted localization |
|---|---|---|---|---|
| ATPS1 | At3g22890 | NM_113189.4 | NP_188929.1 | chloroplast |
| APK1 | At2g14750 | NM_127039.3 | NP_179082.1 | chloroplast |
| APK2 | At4g39940 | NM_120157.3 | NP_195704.1 | chloroplast |
| SAL1 | At5g63980 | NM_125794.4 | NP_201203.2 | chloroplast mitochondrion |

It should be noted that the biosynthesis of GSLs is thought to occur in the cytosol. Particularly, the three desulfoGSL sulfotransferases in *Arabidopsis* have been shown to localize in the cytosol (Klein et al., 2006), which indicates the absence of sub-cellular targeting signals. This argues in favor of a chloroplast PAPS/PAP antiporter that would transport PAPS from the chloroplast to the cytosol and PAP from the cytosol to the chloroplast.

Accordingly, for the exploitation of the mentioned PAPS biosynthesis and regeneration genes in plants with engineered GSL pathways, the co-expression of a PAPS/PAP antiporter might be desirable. Several PAPS transporters have been identified in mammals (for example, the human PAPS transporter 1, with gene SEQ ID NM_005443.4, protein SEQ ID NP_005434.4), and their use as engineered versions that localize to the chloroplast might also be desirable. Alternatively, a suitable PAPS/PAP antiporter from *Arabidopsis* can be identified in the light of the disclosure herein using publicly available co-expression databases as shown for the PAPS biosynthesis and regeneration genes, or using homology-based criteria to the mammalian PAPS transporters.

REFERENCES

Bak S, Feyereisen R (2001) The involvement of two p450 enzymes, CYP83B1 and CYP83A1, in auxin homeostasis and glucosinolate biosynthesis. Plant Physiol. 127, 108-18.

Bednarek P, Piślewska-Bednarek M, Svatoŝ A, Schneider B, Doubský J, Mansurova M, Humphry M, Consonni C, Panstruga R, Sanchez-Vallet A, Molina A, Schulze-Lefert P (2009) A glucosinolates metabolism pathway in living plant cells mediates broad-spectrum antifungal defense. Science, 323, 101-6.

Bertoldi M, Cellini B, Clausen T, Voltattorni CB (2002) Spectroscopic and Kinetic Analyses Reveal the Pyridoxal 5'-Phosphate Binding Mode and the Catalytic Features of *Treponema denticola* Cystalysin. *Biochemistry* 41, 9153-9164

Chen S, Glawischnig E, Jorgensen K, Naur P, Jørgensen B, Olsen C E, Hansen C H, Rasmussen H, Pickett J A, Halkier B A (2003) CYP79F1 and CYP79F2 have distinct functions in the biosynthesis of aliphatic glucosinolates in *Arabidopsis*. Plant J. 33, 923-37.

Chu L, Xu X, Dong Z, Cappelli D, Ebersole J L (2003) Role for Recombinant gamma-Glutamyltransferase from *Treponema denticola* in Glutathione Metabolism. Infect Immun 71, 335-342.

Consonni C, Panstruga R, Sanchez-Vallet A, Molina A, Schulze-Lefert P (2009) A glucosinolates metabolism pathway in living plant cells mediates broad-spectrum antifungal defense. Science, 323, 101-6.

Clay N K, Adio A M, Denoux C, Jander G (2009) Glucosinolate metabolites required for an *Arabidopsis* innate immune response. Science, 323, 95-101.

Fahey J W, Zalcmann A T, Talalay P (2001) The chemical diversity and distribution of glucosinolates and isothiocyanates among plants. *Phytochem.* 56, 5-51.

Field B, Cardon G, Traka M, Botterman J, Vancanneyt G, Mithen R (2004) Glucosinolate and Amino Acid Biosynthesis in *Arabidopsis*. Plant Physiol. 135, 828-839.

Geu-Flores F, Nour-Eldin H H, Nielsen M T, Halkier B A (2007) USER fusion: a rapid and efficient method for simultaneous fusion and cloning of multiple PCR products. Nucleic Acids Res. 35(7):e55. Epub 2007 Mar. 27.

Gil-Mascarell, R., J. M. Lopez-Coronado, J. M. Belles, R. Serrano, & P. L. Rodriguez (1999): The *Arabidopsis* HAL2-like gene family includes a novel sodium-sensitive phosphatase. *Plant Journal*. Vol. 17, no. 4, pp. 373-383.

Hansen B G, Kliebenstein D J, Halkier B A (2007) Identification of a flavin-monooxygenase as the S-oxygenating enzyme in aliphatic glucosinolate biosynthesis in *Arabidopsis*. Plant J. 50, 902-10.

Hansen C H, Wittstock U, Olsen C E, Hick A J, Pickett J A, Halkier B A (2001) Cytochrome p450 CYP79F1 from arabidopsis catalyzes the conversion of dihomomethionine and trihomomethionine to the corresponding aldoximes in the biosynthesis of aliphatic glucosinolates. J Biol. Chem. 276, 11078-85.

Halkier B A, Gershenzon J. (2006) Biology and biochemistry of glucosinolates. Annu Rev Plant Biol. 57, 303-33.

Hansen C H, Du L, Naur P, Olsen C E, Axelsen K B, Hick A J, Pickett J A, Halkier B A (2001) CYP83B1 Is the Oxime-metabolizing Enzyme in the Glucosinolate Pathway in *Arabidopsis*. J Biol Chem 276, 24790-24796

Haseloff J, Siemering K R, Prasher D C, Hodge S (1997) Removal of a cryptic intron and subcellular localization of green fluorescent protein are required to mark transgenic *Arabidopsis* plantsábrightly. PNAS 94, 2122-2127

Horsch R B, Fry J E, HoVmann N L, Eichholtz D, Rogers S G, Fraly R T (1985) A simple and general method for transferring genes into plants. Science 227:1229-1231

Juge N, Mithen R F, Traka M (2007) Molecular basis for chemoprevention by sulforaphane: a comprehensive review. Cell Mol. Life. Sci., 64, 1105-1127.

Klein, M., M. Reichelt, J. Gershenzon, & J. Papenbrock (2006): The three desulfoglucosinolate sulfotransferase proteins in *Arabidopsis* have different substrate specificities and are differentially expressed. *FEBS Journal*. Vol. 273, no. 1, pp. 122-136.

Kliebenstein D J, Lambrix V M, Reichelt M, Gershenzon J, Mitchell-Olds T (2001) Gene Duplication in the Diversification of Secondary Metabolism: Tandem 2-Oxoglutarate—Dependent Dioxygenases Control Glucosinolate Biosynthesis in *Arabidopsis*. Plant Cell 13, 681-693.

Kliebenstein D J, D'Auria J C, Behere A S, Kim J H, Gunderson K L, Breen J N, Lee G, Gershenzon J, Last R L, Jander G (2007) Characterization of seed-specific benzoyloxyglucosinolate mutations in *Arabidopsis thaliana*. The Plant J. 51, 1062-1076. Knill T, Schuster J, Reichelt M, Gershenzon J, Binder S (2007) *Arabidopsis thaliana* branched-chain aminotransferase 3 (BCAT3) functions in both amino acid and glucosinolate biosynthesis. Plant Physiol. 2007 Dec. 27 [Epub ahead of print]

Kroymann J, Textor S, Tokuhisa J G, Falk K L, Bartram S, Gershenzon J, Mitchell-Olds T (2001) A gene controlling variation in *Arabidopsis* glucosinolate composition is part of the methionine chain elongation pathway. Plant Physiol. 127, 1077-88.

Leustek T, Saito K (1999) Sulfate Transport and Assimilation in Plants. Plant Physiol 120, 637-644

Massiere F, Badet-Denisot M A (1998) The mechanism of glutamine-dependent amidotransferases. Cell Mol Life Sci 54, 205-222

Mikkelsen M D, Halkier B A (2003) Metabolic engineering of valine- and isoleucine-derived glucosinolates in *Arabidopsis* expressing CYP79D2 from Cassava. Plant Physiol. 131, 773-9.

Mikkelsen M D, Naur P, Halkier B A (2004) *Arabidopsis* mutants in the C—S lyase of glucosinolate biosynthesis establish a critical role for indole-3-acetaldoxime in auxin homeostasis. Plant J. 37, 770-7.

Mikkelsen M D, Flores F G, Nielsen M T, Halkier B A (2008) Biosynthetic engineering of glucosinolates. US provisional patent, SMK/FP6525786.

Nour-Eldin H H, Hansen B G, Nørholm M H, Jensen J K, Halkier B A (2006) Advancing uracil-excision based cloning towards an ideal technique for cloning PCR fragments. Nucleic Acids Res. 34(18):e122. Epub 2006 Sep. 25.

Olsen N B (2008) Broccoli bekmper brystkrft, published online at http://ing.dk, December 15.

Piotrowski M, Schemenewitz A, Lopukhina A, Muller A, Janowitz T, Weiler E W, Oecking C (2004) Desulfoglucosinolate sulfotransferases from *Arabidopsis* thaliana catalyze the final step in the biosynthesis of the glucosinolate core structure. J Biol. Chem. 279, 50717-25. Quintero, F. J., B. Garciadeblas, & N. A. Rodriguez (1996): The SAL1 gene of *Arabidopsis*, encoding an enzyme with 3'(2'),5'-bisphosphate nucleotidase and inositol polyphosphate 1-phosphatase activities, increases salt tolerance in yeast. *Plant Cell*. Vol. 8, no. 3, pp. 529-537.

Rosenthal, E., Leustek, T. (1995) A multifunctional *Urechis caupo* protein, PAPS synthetase, has both ATP sulfurylase and APS kinase activities. Gene 165 (2) 243-248.

Schuster J, Knill T, Reichelt M, Gershenzon J, Binder S (2006) Branched-chain aminotransferase4 is part of the chain elongation pathway in the biosynthesis of methionine-derived glucosinolates in *Arabidopsis*. Plant Cell 18, 2664-79.

Tamura K, Dudley J, Nei M, Kumar S (2007) MEGA4: Molecular Evolutionary Genetics Analysis (MEGA) Software Version 4.0. Mol Biol Evol 24, 1596-1599

Textor S, de Kraker J W, Hause B, Gershenzon J, Tokuhisa J G (2007) MAM3 catalyzes the formation of all aliphatic glucosinolate chain lengths in *Arabidopsis*. Plant Physiol. 144, 60-71.

Thompson J D, Gibson T J, Plewniak F, Jeanmougin F, Higgins D G (1997) The CLUSTAL_X windows interface: flexible strategies for multiple sequence alignment aided by quality analysis tools. Nucleic Acids Res 25, 4876-4882

Topfer R, Matzeit V, Gronenborn B, Schell J, Steinbiss H H (1987) A set of plant expression vectors for transcriptional and translational fusions. Nucleic Acids Res 15, 5890

SønderbyIE, Hansen B G, Bjarnholt N, Ticconi C, Halkier B A, Kliebenstein D J (2007) A Systems Biology Approach Identifies a R2R3 MYB Gene Subfamily with Distinct and Overlapping Functions in Regulation of Aliphatic Glucosinolates. PLoS ONE 19;2(12):e1322.

Voinnet O, Rivas S, Mestre P and Baulcombe D (2003) An enhanced transient expression system in plants based on suppression of gene silencing by the p19 protein of tomato bushy stunt virus. The Plant J 33, 949-956.

Wittstock U, Halkier B A (2000) Cytochrome P450 CYP79A2 from *Arabidopsis thaliana* L. Catalyzes the Conversion of L-Phenylalanine to Phenylacetaldoxime in the Biosynthesis of Benzylglucosinolate. J Biol Chem 275: 14659-14666

Sequences and accession numbers of genes and proteins used in this study.

1:
NM_119199, At4g30530 defense-related protein, putative
CDS:

```
  1 ATGGTGGAGC AAAAGAGATA CGCTCTGTTT CTAGCGACTT TGGACTCAGA
 51 GTTCGTGAAG AAAACTTACG GAGGATACCA CAACGTGTTC GTGACGACGT
101 TCGGAGACGA AGGAGAGCAT TGGGACTCCT TTAGAGTCGT CAGCGGAGAG
151 TTTCCTGACG AGAAAGATCT GGAGAAATAC GATGGCTTCG TTATCAGCGG
201 AAGCTCTCAC GATGCCTTTG AGAATGATGA TTGGATCCTT AAGCTCTGTG
251 ATATTGTCAA GAAAATTGAT GAGATGAAGA AGAAAATTCT TGGCATCTGC
301 TTTGGTCATC AGATCATAGC CAGGGTAAGG GGAGGAACAG TCGGAAGAGC
351 AAAGAAGGGA CCAGAACTTA AACTTGGAGA CATAACCATC GTCAAGGATG
401 CGATTACGCC TGGAAGTTAC TTCGGAAACG AGATTCCTGA TAGCATAGCG
451 ATCATCAAAT GTCACCAGGA CGAAGTGTTG GTGCTGCCCG AAACTGCTAA
501 AGTGCTTGCG TATTCCAAGA ACTACGAGGT GGAGATGTAT TCGATTGAGG
551 ATCATTTGTT CTGTATCCAA GGACATCCTG AGTATAACAA AGAGATTCTC
601 TTCGAGATTG TTGATCGTGT TCTTGCTCTA GGCTACGTCA AGCAAGAATT
651 TGCTGATGCG GCTAAGGCAA CGATGGAGAA TAGGGGAGCA GACAGGAAGC
701 TTTGGGAGAC GATTTGCAAG AACTTCCTCA AAGGCAGAGT TCCAACTAAC
751 TAG
```

2:
NP_194782.1, NM_119199, At4g30530 defense-related protein, putative
Protein:

```
  1 MVEQKRYALF LATLDSEFVK KTYGGYHNVF VTTFGDEGEH WDSFRVVSGE
 51 FPDEKDLEKY DGFVISGSSH DAFENDDWIL KLCDIVKKID EMKKKILGIC
101 FGHQIIARVR GGTVGRAKKG PELKLGDITI VKDAITPGSY FGNEIPDSIA
151 IIKCHQDEVL VLPETAKVLA YSKNYEVEMY SIEDHLFCIQ GHPEYNKEIL
201 FEIVDRVLAL GYVKQEFADA AKATMENRGA DRKLWETICK NFLKGRVPTN
```

3:
NM_119201.2, At4g30550, *Arabidopsis thaliana* glutamine amidotransferase class-I domain-containing protein.
CDS

```
  1 ATGGTGGTTA TTGAGCAGAA GAAGAGGTTT GCTTTGTTTT TAGCGACGTG
 51 TGATTCAGAG TTCGTGAAGA AGACTTACGG TGGTTACTTC AATGTCTTCG
```

-continued

```
101 TTTCAACTTT CGGCGAAGAA GGTGAGCAAT GGGATCTATT CCGAGTCATC

151 GACGGACAAT TTCCCGACGA GAATGATTTA GACAAGTACG ACGGTTTCGT

201 TATCAGTGGT AGTCCACATG ATGCTTTCGG AGACGCCGAT GGATTGTTA

251 AGCTTTGCGA AGTTTGTCAG AAACTTGATC ACATGAAGAA GAAAGTTCTC

301 GGCATCTGCT TCGGCCACCA GATAATTACT AGAGTTAAAG GTGGGAAGAT

351 AGGAAGAGCA CTCAAAGGTG CAGATATGGG ACTTAGAAGC ATAACCATAG

401 CGAAAGACAA TGAAAAACTA CGAGGTTACT TTGGAGACGT TGAGGTCCCA

451 GCATCTTTAG CTATTATAAA ATGTCATCAG GATGAAGTGT TGGAACTTCC

501 TGAGTCTGCT ACACTACTTG CTTCTTCTGA GGTATGTAAC GTCGAGATGT

551 TCTCTATTGG AGATCATTTT TTCTGTATTC AAGGGCATCC AGAGTATAAC

601 AAAGAGATTC TGTTTGAGAT TGTGGACCGA GTCCTTAATA TGAAGCTGAT

651 GGAGCAAGAG TTTGCGGATA AGGCAAAGAG TACGATGGAG ACTGCGCAAC

701 CAGACAGGAT TCTATGGCAG AAGCTCTGCA AAACTTCCT GAAAGGTTGA
```

4:
NP_194784.1, NM_119201.2, At4g30550, *Arabidopsis thaliana* glutamine amidotransferase class-I domain-containing protein.

```
  1 MVVIEQKKRF ALFLATCDSE FVKKTYGGYF NVFVSTFGEE GEQWDLFRVI

51 DGQFPDENDL DKYDGFVISG SPHDAFGDAD WIVKLCEVCQ KLDHMKKKVL

101 GICFGHQIIT RVKGGKIGRA LKGADMGLRS ITIAKDNEKL RGYFGDVEVP

151 ASLAIIKCHQ DEVLELPESA TLLASSEVCN VEMFSIGDHF FCIQGHPEYN

201 KEILFEIVDR VLNMKLMEQE FADKAKSTME TAQPDRILWQ KLCKNFLKG
```

5:
NM_127958, AT2G23960 *Arabidopsis thaliana* defense-related protein, putative
CDS:

```
  1 ATGGCTGAAC AAAAGAAGTA CCTATTGTTT CTAGCGACAC CGGACTCGGA

51 GTTTGCGAAG AAGACATATG GAGGATACCA TAATGTGTTT GTTTCACTGC

101 TTGGCGATGA AGGAGAGCAA TGGGACTCTT TTAGAGTCGT GGACGGCGAG

151 TTTCCAGAAG AGAAGGATCT TGAGAAATAC GAAGGATTTG TAATCAGTGG

201 TAGCTCTCAT GATGCCTTTC AAGACACTGA TTGGATCTTA AAGCTCTGTG

251 ATATCATCAA GAAACTCGAT GACATGAACA AGAAAGTCCT CGGTATTTGC

301 TTTGGCCACC AGCTAATAGC TAGAGCGAAG GGAGGCAAAG TAGCGAGAGC

351 AAGGAAAGGA CCAGAGCTTT GCCTTGGAAA CATAACCATC GTGAAAGAGG

401 CAGTGATGCC GGAAAATTAC TTCGGCGAAG AAGTTCCAGC GAATCTGAGG

451 ATCATAAAAT GTCATCAGGA TGAAGTTTTG GAGCTTCCGG AAAATGCAAA

501 ACTGTTAGCA TATTCAAGCA TGTACGAGGT AGAGATGTAT TCAATCAAAG

551 ATAACTTCCT TTGCATTCAG GGACATCCTG AGTATAACCG TGACATCTTG
```

```
-continued
601 TTCGATATCA TTGATCGTGT TCTTGCCGGA GGCCACATTA AGCAAAACTT

651 TGCCGAAACG TCAAAGGCAA CAATGGAAAA GAATGAAGCA GACAGGAAGT

701 TTTGGCAGAA AATTTGCAAA AACTTCCTCA AACGTCAACC CTCCTTATTA

751 GTTTGA
```

6:
NP_179974.2, NM_127958, AT2G23960 *Arabidopsis thaliana* defense-related protein, putative
Protein:

```
  1 MAEQKKYLLF LATPDSEFAK KTYGGYHNVF VSLLGDEGEQ WDSFRVVDGE

51 FPEEKDLEKY EGFVISGSSH DAFQDTDWIL KLCDIIKKLD DMNKKVLGIC

101 FGHQLIARAK GGKVARARKG PELCLGNITI VKEAVMPENY FGEEVPANLR

151 IIKCHQDEVL ELPENAKLLA YSSMYEVEMY SIKDNFLCIQ GHPEYNRDIL

201 FDIIDRVLAG GHIKQNFAET SKATMEKNEA DRKFWQKICK NFLKRQPSLL

251 V
```

7:
NM_127959, AT2G23970, *Arabidopsis thaliana* defense-related protein, putative
CDS:

```
  1 ATGGTTAATG AGCAAAAGAG ATTTGCTTTG TTTCTTGCTA CGAGCGATTC

51 AACGTTCGTG AAGAAAGCGT ATGGAGGCTA TTTCAACGTG TTTGTTTCGA

101 CTTTTGGTGA AGATGGTGAG CAATGGGATC TGTTTCGAGT GATCGACGGC

151 GAGTTTCCTG ACGATAAGGA TCTGGATAAG TACGATGGTT TTGTTATTAG

201 TGGAAGCCTT AACGATGCTT TTGGTGATGA TGATTGGATC GTTAAGCTTT

251 GTTCTCTTTG CCAAAAGCTT GACGACATGA AGAAGAAGGT TCTTGGTATC

301 TGCTTTGGCC ACCAGATACT AAGTAGAATC AAAGGAGGGA AAGTCGGAAG

351 GGCGAGTAGA GGTTTGGATA TGGGACTAAG AAGCATAACA ATGGTTACAG

401 ACGCGGTGAA GCCAGGTGGT TACTTTGGAA GCCAGATTCC GAAATCACTA

451 GCCATTATAA AATGCCATCA AGATGAAGTT CTTGAACTCC CTGAATCAGC

501 CACATTGCTT GCTTATTCAG ACAAATACAA CGTTGAGATG TGTTCGTATG

551 GAAACCACTT GCTAGGCATC CAAGGCCATC CTGAGTACAA CAAAGAGATT

601 CTTTTCGAGA TCATTGATCG TGTCGTCAAT TTGAAGTTGA TGGAGCAAGA

651 TTTTGCGGAT AAGGCGAAGG CAACGATGGA AAACGCGGAA CCAGATCGGA

701 AGCAATGGCA GACTCTCTGC AAAAACTTTC TCAAAGGAAG ATCCGAGCAA

751 GTTTAA
```

8: NP_179975.1, NM_127959, AT2G23970, *Arabidopsis thaliana* defense-related protein, putative
Protein:

```
  1 MVNEQKRFAL FLATSDSTFV KKAYGGYFNV FVSTFGEDGE
    QWDLFRVIDG

51 EFPDDKDLDK YDGFVISGSL NDAFGDDDWI VKLCSLCQKL
    DDMKKKVLGI

101 CFGHQILSRI KGGKVGRASR GLDMGLRSIT MVTDAVKPGG
    YFGSQIPKSL

151 AIIKCHQDEV LELPESATLL AYSDKYNVEM CSYGNHLLGI
    QGHPEYNKEI

201 LFEIIDRVVN LKLMEQDFAD KAKATMENAE PDRKQWQTLC
    KNFLKGRSEQ

251 V
```

9:

NM_119200, AT4G30540 glutamine amidotransferase class-I domain-containing protein

CDS:

```
  1 ATGGTGAAGC AGATAAGAAG ATACGCTCTA TTTCAAGCCA
    CGCCAGATTC
 51 TGAGTTCGTG AAGGAGATGT ACGGAGGCTA CTTCAACGTA
    TTCGTGTCGG
101 CTTTCGGAGA CGAAGGAGAG CAATGGGATC TTTTCCGTGT
    GATCGACGGC
151 GAGTTTCCTC GCGACGAAGA TCTTGAGAAG TATGAGGGAT
    TCGTCATTAG
201 TGGGAGTTTA CATGACGCTT TCACAGAAGA GGATTGGATC
    ATTGAGCTTT
251 GCTCTGTTTG CAAAAAACTT GATGTGATGA AGAAGAAAAT
    TCTTGGCATA
301 TGCTTTGGTC ACCAGATCAT ATGTAGAGTA AGAGGTGGGA
    AAGTGGGAAG
351 GGCTCGTAAA GGACCAGACA TAGGCCTCGG TAACATAACG
    ATCGTTCAAG
401 ATGTGATCAA ACCGGGTGAT TACTTCGATC AAATCGAGTC
    ATTGTCGATC
451 ATACAATGTC ATCGAGACGA AGTACTTGAG CCTCCAGAGT
    CGGCTAGAGT
501 CATAGGATTC TCAGACAAAT GCGACGTTGA GATATTCTCA
    GTGGAAGATC
551 ACTTGCTTTG CTTTCAAGGT CATCCCGAGT ATAACAAAGA
    GATTCTCCTT
601 GAGATCATTG ATCGTGTCCA CAAGATCAAA TTTGTTGAGG
    AGGAAATTTT
651 GGAGAAAGCA AAGGATTCGA TCAAGAAGTT TGAACCAGAC
    ACGCAGCGTT
701 TGCACATGCT TTGCAAGAAT TTTCTGAAAG GACGAAGAAC
    CCACTAA
```

10:

NP_194783.1, NM_119200, AT4G30540 glutamine amidotransferase class-I domain-containing protein Protein:

```
  1 MVKQIRRYAL FQATPDSEFV KEMYGGYFNV FVSAFGDEGE
    QWDLFRVIDG
 51 EFPRDEDLEK YEGFVISGSL HDAFTEEDWI IELCSVCKKL
    DVMKKKILGI
101 CFGHQIICRV RGGKVGRARK GPDIGLGNIT IVQDVIKPGD
    YFDQIESLSI
151 IQCHRDEVLE PPESARVIGF SDKCDVEIFS VEDHLLCFQG
    HPEYNKEILL
201 EIIDRVHKIK FVEEEILEKA KDSIKKFEPD TQRLHMLCKN
    FLKGRRTH
```

11:

AY030296.1, *Brassica* carinata defense-related protein

CDS

```
   1 attgcacctc tctctttatt ctctctctgc taatcaacca
     ctctctctat ttacgttagc
  61 cggtaaaaaa atggttgagc agaaaaagtt cgctctgttt
     ctagcgactc ctgattcaga
 121 gttcgtgaag aaagagtacg gaggatacca caacgtgttc
     gtgtccacgt tcggtgacga
 181 aggagagcat tgggactcgt ttagagtcgt tgaaggcgag
     tttcccgacg agaaagatct
 241 tgacaagtac gacggtttcg ttattagtgg aagctctcac
     gattccttcg agaatgatcc
 301 ttggatcctt aggctatgtg agatcgtcaa gatactcgat
     gagaagaaga gaaaaattct
 361 tggcatatgc tttggtcacc agatcatagc cagagtaaga
     ggaggaacag tgggaagagc
 421 aaggaaggga ccagaactta gcttacaga cataaccatc
     gtgaaggatg cgattaaacc
 481 aggaagtttc ttcggaaacg agattccgga tagcatagcc
     atcctaaagt tacatcagga
 541 cgaagtgtta gtgttgcctg aatctgctaa agtactagct
     tattcagaaa agtacgaggt
 601 ggagatgttc tccattgagg atcatttatt ctgtattcaa
     ggacatcccg agtataacag
 661 agagattctc cacgagatcg ttgatcgtgt tcttcgtctt
     ggcttcatca aggaagattt
 721 tgcggatgcg gcaaaagcct cgatggagaa taggggagca
     gacaggaaac ttttggagac
 781 gatttgcaag aattttctca aaggcagagt tccagctaat
     taattagttt cactcccaaa
 841 ttatctattt ggctcttgtt atattggagc tagcacttat
     ggatttatta tcttgctgta
 901 ttgtattcaa tatataacct attaatctca tccttgtcaa
     ggaaacaaaa actcatatta
 961 atctcaatgt catatttatg tgttgttacc cataagtaaa
     attattcaat aaaaactata
1021 gttttgcaaa aaaaaaaaaa aaaa
```

12:

AAK50344.1, AY030296.1, *Brassica* carinata defense-related protein

Protein:

```
  1 mveqkkfalf latpdsefvk keyggyhnvf vstfgdegeh
    wdsfrvvege fpdekdldky
 61 dgfvisgssh dsfendpwil rlceivkild ekkkkilgic
    fghqiiarvr ggtvgrarkg
121 pelkltditi vkdaikpgsf fgneipdsia ilklhqdevl
    vlpesakvla ysekyevemf
181 siedhlfciq ghpeynreil heivdrvlrl gfikedfada
    akasmenrga drklletick
241 nflkgrvpan
```

13:
NM_129871.2, AT2G43100 aconitase C-terminal domain-containing protein, AC1
CDS:

```
  1 ATGGCGTATT CTCTTCCTAC ATTTCCCCAA GCCTTACCTT
    GCTCGTCAAC
 51 CAAAACTTCT TCCTCCTTGG CTACCTTCCG ATCTCCTTTC
    TTAAGATTCA
101 ATGGTTCCAC TTCCTTAATC CCCTCCTCTA TCTCCATCAC
    TTCACGTGGC
151 ACATCCTCCC CGACCATCAT CCCACGTGCT GCCGCCTCAG
    AATCCGACTC
201 TAACGAAGCC CTAGCCAACA CAACCTTCCA CGGCCTCTGC
    TATGTCTTGA
251 AAGACAACAT AGACACCGAC CAGATCATCC CAGCAGGAGC
    CGCTTGCACC
301 TTCCCATCGA ACCAGCAAGA GCGTGATGAG ATCGCCGCTC
    ACGCTCTCTC
351 TGGTCTACCA GACTTCCACA AAACACGGTT CATTGAGCCA
    GGAGAGAACA
401 GATCAAAGTA CTCAATCATA ATCGGCGGCG AAAACTTTGG
    TTGCGGATCG
451 TCACGTGAAC ATGCTCCGGT CTGTCTTGGA GCAGCTGGAG
    CTAAAGCCAT
501 AGTTGCTGAG TCTTACGCAA GAATCTTTTT CCGTAACTCG
    GTTGCTACAG
551 GAGAGGTGTT TCCGCTCGAG TCAGAGGTTA GAGTCTGTGA
    GGAGTGTAAG
601 ACAGGAGATA CGGTGACGAT CGAGCTGAGT GATAGTGGTG
    GTTTATTGAC
651 TAATCACACG ACCGGTAAAA ACTATAAGCT GAAGTCGATC
    GGTGATGCTG
701 GACCGGTTAT TGATGCTGGT GGTATTTTTG CTTATGCGAG
    GATGATGGGA
751 ATGATTCCAT CATTAGCTTA A
```

14: NP_181838.1, AT2G43100 aconitase C-terminal domain-containing protein, AC1
Protein:

```
  1 MAYSLPTFPQ ALPCSSTKTS SSLATFRSPF LRFNGSTSLI
    PSSISITSRG
 51 TSSPTIIPRA AASESDSNEA LANTTFHGLC YVLKDNIDTD
    QIIPAGAACT
101 FPSNQQERDE IAAHALSGLP DFHKTRFIEP GENRSKYSII
    IGGENFGCGS
151 SREHAPVCLG AAGAKAIVAE SYARIFFRNS VATGEVFPLE
    SEVRVCEECK
201 TGDTVTIELS DSGGLLTNHT TGKNYKLKSI GDAGPVIDAG
    GIFAYARMMG
251 MIPSLA
```

15: NM_115761.3, AT3G58990, aconitase C-terminal domain-containing protein, AC2
CDS:

```
  1 ATGGCGACTT CTCAGCAATT TTTAAACCCT ACACTCTTCA
    AATCCTTAGC
 51 TTCCTCAAAC AAAAACTCAT GTACTCTCTG CCCATCTCCT
    TTCTTGCAAC
101 TCAAGTCCGC CTCCACAATT TTCAATTACA AACCACTTAC
    TTCCTCCTCC
151 GCCACGATCA TCACACGCGT CGCTGCATCA TCCTCCGATT
    CAGGCGAGTC
201 AATAACCAGA GAGACTTTCC ACGGCCTCTG CTTCGTCTTG
    AAAGACAACA
251 TCGACACCGA TCAAATAATC CCCGCCGAGT ACGGCACTCT
    CATCCCTTCG
301 ATTCCAGAAG ATCGCGAGAA ACTCGGCTCT TTCGCGCTTA
    ACGGCTTACC
351 AAAATTCTAC AACGAACGTT TCGTTGTTCC AGGAGAGATG
    AAATCAAAGT
401 ACTCAGTCAT CATCGGCGGC GATAATTTCG GTTGCGGATC
    TTCCCGCGAA
451 CACGCTCCAG TTTGTCTCGG CGCGGCGGGA GCTAAAGCTG
    TGGTGGCGGA
501 ATCGTACGCT AGGATCTTTT TCAGGAACTG TGTAGCTACA
    GGTGAGATTT
551 TCCCGTTGGA ATCGGAGGTT AGGATTTGCG ACGAGTGCAA
    AACAGGGGAT
601 GTGGTGACAA TCGAACACAA GGAAGACGGT AGTAGTTTGC
    TGATCAATCA
651 TACGACGAGG AAAGAATACA AACTGAAACC GCTCGGTGAT
    GCCGGTCCGG
701 TGATCGACGC CGGTGGAATC TTCGCTTATG CAAGAAAAGC
    CGGCATGATT
751 CCTTCTGCTT GA
```

16: NP_191458.1, AT3G58990, aconitase C-terminal domain-containing protein, AC2
Protein:

```
  1 MATSQQFLNP TLFKSLASSN KNSCTLCPSP FLQLKSASTI
    FNYKPLTSSS
 51 ATIITRVAAS SSDSGESITR ETFHGLCFVL KDNIDTDQII
    PAEYGTLIPS
101 IPEDREKLGS FALNGLPKFY NERFVVPGEM KSKYSVIIGG
    DNFGCGSSRE
151 HAPVCLGAAG AKAVVAESYA RIFFRNCVAT GEIFPLESEV
    RICDECKTGD
201 VVTIEHKEDG SSLLINHTTR KEYKLKPLGD AGPVIDAGGI
    FAYARKAGMI
251 PSA
```

17: NM_102856.2, AT1G31180, 3-isopropylmalate dehydrogenase, IPMDH
CDS:

```
  1 ATGGCGGCGT TTTTGCAAAC TAACATCCGT CTGGAGATCA
    TACCGGGAAG

51 ATACAGTTCT CTCACCGATC ATAAGTTTCG TGCGCCGTAT
    CGAATTAGGT

101 GCGCCGCCGC TTCACCGGTG AAAAAACGGT ATAACATCAC
    TCTGCTTCCC

151 GGCGATGGTA TCGGTCCAGA AGTTATATCT GTTGCTAAGA
    ATGTGCTTCA

201 GAAAGCTGGA TTTCTCCAAG GACTAGAGTT TGATTTCCAG
    GAGATGCCTT

251 TCGGCGGAGC AGCTTTGGAT TTGGTCGGAG TTCCATTGCC
    GGAGGAAACT

301 TCCACTGCTG CTAAACAGTC TGATGCCATT CTTCTTGGAG
    CTATCGGAGG

351 GTACAAATGG GACAAGAATG AGAAACATCT GAGACCTGAG
    ATGGGTCTGC

401 TTAACATTCG AAGAGATCTC AATGTCTTTG CTAATTTGAG
    ACCTGCTACA

451 GTTTTACCAC AGCTAGTTGA TGCTTCCACA CTGAAGAAAG
    AAGTAGCACA

501 AGGTGTTGAT ATGATGATTG TAAGGGAGCT CACTGGAGGT
    ATTTACTTTG

551 GAGAGCCAAG AGGCATTACG ATCAACGAAA ATGGCGAAGA
    AGTCGGTTTT

601 AATACAGAGA TCTACGCTGC TCACGAGATT GACAGAATTG
    CTCGTGTTGC

651 ATTCGAGACT GCTAGGAAAA GGCGTGGCAA GCTGTGTTCT
    GTTGACAAAG

701 CCAATGTCTT GGATGCATCA ATATTGTGGA GGAAAAGAGT
    AACAGCTTTA

751 GCCTCTGAAT ATCCAGATGT TGAACTATCA CATATGTATG
    TCGATAATGC

801 TGCGATGCAG CTTGTCCGTG ACCCGAAACA GTTTGACACA
    ATCGTCACCA

851 ATAACATTTT TGGTGATATA TTGTCTGATG AAGCTTCAAT
    GATCACTGGT

901 AGCATTGGGA TGCTTCCATC TGCAAGTCTT GGTGAATCGG
    GACCTGGACT

951 CTTTGAACCT ATACATGGTT CAGCACCAGA TATAGCTGGA
    CAAGACAAGG

1001 CAAACCCATT GGCCACCATT CTCAGTGCGG CGATGCTTCT
     CAAGTATGGA

1051 CTTGGAGAAG AAAAGGCTGC AAAGATGATT GAAGACGCGG
     TCGTGGATGC

1101 TCTGAACAAA GGTTTCAGAA CCGGAGACAT CTACTCCCCC
     GGAAATAAAC

1151 TGGTGGGATG CAAGGAAATG GGTGAGGAGG TTCTCAAATC
     AGTGGACTCC

1201 AAAGTTCCTG TTTAA
```

18: NP_174403.1, AT1G31180, 3-isopropylmalate dehydrogenase, IPMDH
Protein:

```
  1 MAAFLQTNIR LEIIPGRYSS LTDHKFRAPY RIRCAAASPV
    KKRYNITLLP

51 GDGIGPEVIS VAKNVLQKAG FLQGLEFDFQ EMPFGGAALD
    LVGVPLPEET

101 STAAKQSDAI LLGAIGGYKW DKNEKHLRPE MGLLNIRRDL
    NVFANLRPAT

151 VLPQLVDAST LKKEVAQGVD MMIVRELTGG IYFGEPRGIT
    INENGEEVGF

201 NTEIYAAHEI DRIARVAFET ARKRRGKLCS VDKANVLDAS
    ILWRKRVTAL

251 ASEYPDVELS HMYVDNAAMQ LVRDPKQFDT IVTNNIFGDI
    LSDEASMITG

301 SIGMLPSASL GESGPGLFEP IHGSAPDIAG QDKANPLATI
    LSAAMLLKYG

351 LGEEKAAKMI EDAVVDALNK GFRTGDIYSP GNKLVGCKEM
    GEEVLKSVDS

401 KVPV
```

19: NM_202809.2, AT4G12030, methylthioalkyl α-ketoacid chloroplastidic transporter, MAC-T
CDS:

```
  1 ATGGGTGTGA TATCTCCGAC TGAAACTCTG TTCTTAAAGT
    CTCAACATCG

51 TCTTCTTCAA CCCTCGAAACT ATTCATACGC ACTTGCTTTT
    CACAGCACTC

101 GACGAGTTGC GAATTTCCCA CGCAACTCAT TCTCTTCTCT
    AGGATCATGT

151 TCTGTAGATT TTCCACTACG AAGTAACCCG ATTTCACAAA
    ATAGCAAGTC

201 AATTCATCCT TGGCGGAGAT ATGTATCCGA ATCTGACTCA
    AACGAGCTGT

251 ATCATAAGAA GGTTTCTTCT ATTATGGAAA CATTAAAGCA
    AGCCTACTCT

301 TTTATTCCTC ATGGAATTCT GTTAAGTACA ATATTAGCTC
    TTGTCTATCC

351 ACCTTCTTTC ACATGGTTCA AGCCAAGGTA CTTTGTACCT
    GGCTTAGGGT

401 TCATGATGTT TGCTGTTGGT ATCAACTCTA ATGAAAGAGA
    TTTTCTTGAA

451 GCACTTAAAA GACCAGATGC TATTTTTGCC GGTTACATCG
    GACAATACTT

501 GATTAAACCT CTCTTAGGTT ACATTTTCGG CGTAATTGCT
    GTCTCTCTTT

551 TCAATCTACC TACTTCTATA GGTGCTGGAA TCATGTTGGT
    CTCATGTGTT

601 AGTGGAGCTC AGCTATCAAA TTACACAACT TTCTTGACCG
    ATCCTTCACT

651 CGCGGCGCTT AGCATCGTCA TGACATCTAT CTCAACGGCC
    ACTGCGGTCC

701 TCGTTACACC TATGCTTTCA CTCTTACTCA TTGGTAAAAA
    GCTTCCCGTT
```

-continued

```
 751 GATGTGTTTG GGATGATCTC TAGCATTCTT CAAGTGGTGA
     TTACACCTAT

801 TGCCGCAGGA CTACTTCTGA ACCGGTTGTT TCCAAGGTTG
     TCTAATGCAA

851 TCAAACCATT TCTTCCGGCG TTAACAGTTA TCGATATGAG
     TTGTTGCATA

901 GGAGCACCCC TTGCTTTGAA TATAGATTCA ATCTTGTCTC
     CGTTTGGTGC

951 AACCATTTTG TTCCTCGTCA TCACGTTTCA TCTCTTGGCT
     TTTGTTGCTG

1001 GTTACTTTTT CACTGGTTTC TTCTTCAGCA AGGCACCTGA
     TGTAAAAGCT

1051 CTGCAAAGAA CAATTTCCTA TGAAACAGGA ATGCAAAGTA
     GTCTTCTCGC

1101 TCTGGCCCTC GCTACAAAGT TCTTTCAAGA TCCTCTCGTT
     GGAGTGCCTC

1151 CAGCAATCTC CACGGTTGTT ATGTCTCTAA TGGGCGTCTC
     GCTTGTTACC

1201 ATATGGAAAA ACAGAAAGGA GTAG
```

20: NP_974538.1, AT4G12030, methylthioalkyl α-ketoacid chloroplastidic transporter, MAC-T Protein:

```
  1 MGVISPTETL FLKSQHRLLQ PRNYSYALAF HSTRRVANFP
    RNSFSSLGSC

51 SVDFPLRSNP ISQNSKSIHP WRRYVSESDS NELYHKKVSS
    IMETLKQAYS

101 FIPHGILLST ILALVYPPSF TWFKPRYFVP GLGFMMFAVG
    INSNERDFLE

151 ALKRPDAIFA GYIGQYLIKP LLGYIFGVIA VSLFNLPTSI
    GAGIMLVSCV

201 SGAQLSNYTT FLTDPSLAAL SIVMTSISTA TAVLVTPMLS
    LLLIGKKLPV

251 DVFGMISSIL QVVITPIAAG LLLNRLFPRL SNAIKPFLPA
    LTVIDMSCCI

301 GAPLALNIDS ILSPFGATIL FLVITFHLLA FVAGYFFTGF
    FFSKAPDVKA

351 LQRTISYETG MQSSLLALAL ATKFFQDPLV GVPPAISTVV
    MSLMGVSLVT

401 IWKNRKE
```

21: NM_111189.2, AT3G03190, ATGSTF11 (GLUTATHIONE S-TRANSFERASE F11), GSTF11

CDS:

```
  1 ATGGTGGTCA AGTATATGG GCAGATAAAA GCAGCTAATC
    CACAAAGAGT

51 ATTGCTCTGC TTTTTGGAAA AAGACATCGA GTTTGAAGTA
    ATTCATGTCG

101 ATCTCGATAA ACTTGAACAG AAAAAACCAC AACATCTTCT
    TCGTCAGCCG

151 TTTGGTCAAG TTCCAGCTAT TGAAGATGGA TATCTGAAGC
    TTTTTGAATC

201 GCGAGCCATA GCGAGGTACT ACGCGACAAA GTATGCGGAC
    CAAGGAACGG

251 ACCTATTGGG CAAGACTTTG GAGGGACGAG CCATTGTGGA
    CCAGTGGGTG

301 GAAGTTGAGA ATAACTATTT CTACGCTGTG GCTCTACCCT
    TAGTTATGAA

351 CGTCGTCTTT AAGCCCAAGT CTGGTAAGCC ATGCGACGTC
    GCTTTGGTTG

401 AGGAGCTAAA GGTCAAGTTC GACAAGGTCC TGGATGTGTA
    TGAGAACCGG

451 TTAGCTACGA ACCGGTACTT GGGCGGTGAT GAATTCACAT
    TAGCTGATTT

501 GAGTCATATG CCCGGTATGA GATATATCAT GAATGAAACC
    AGTTTGAGTG

551 GTTTGGTTAC GTCTCGAGAG AATCTCAACC GGTGGTGGAA
    TGAGATTTCG

601 GCTAGACCGG CTTGGAAGAA GCTCATGGAA TTGGCTGCCT
    ATTAA
```

22: NP_186969.1, ATGSTF11 (GLUTATHIONE S-TRANSFERASE F11), GSTF11

Protein:

```
  1 MVVKVYGQIK AANPQRVLLC TLEKDIEFEV IHVDLDKLEQ
    KKPQHLLRQP

51 FGQVPAIEDG YLKLFESRAI ARYYATKYAD QGTDLLGKTL
    EGRAIVDQWV

101 EVENNYFYAV ALPLVMNVVF KPKSGKPCDV ALVEELKVKP
    DKVLDVYENR

151 LATNRYLGGD EFTLADLSHM PGMRYIMNET SLSGLVTSRE
    NLNRWWNEIS

201 ARPAWKKLME LAAY
```

The invention claimed is:

1. A method of converting a plant or microbial host from a phenotype whereby the host is unable to carry out glucosinolate (GSL) biosynthesis from an amino acid GSL-precursor to any GSL which is an aliphatic GSL selected from the group consisting of 3-methylthiopropyl glucosinolate, 4-methylthiobutyl glucosinolate, 7-methylthioheptyl glucosinolate and 8-methylthiooctyl glucosinolate, to a phenotype whereby the host carries out the GSL biosynthesis of at least one of said GSLs, the method comprising expressing a heterologous nucleic acid within the host or one or more cells thereof, following an earlier step of introducing the nucleic acid into the host or an ancestor of either, wherein the heterologous nucleic acid comprises a plurality of nucleotide sequences each of which encodes a polypeptide which in combination have the GSL biosynthesis activity, and wherein the heterologous nucleic acid encodes all of the following polypeptides:
a CYP83A1;
one of a CYP79F1, a CYP79F2, a CYP79D2 or a CYP79D1;
a sulfotransferase;
a UDP-glucosyl transferase;
a C—S lyase; and
a gamma-glutamyl peptidase polypeptide, wherein the gamma-glutamyl peptidase polypeptide is any one of SEQ ID NOs: 2, 4, 6, 8 or 10 or a gamma-glutamyl polypeptidase polypeptide sharing at least 95% identity with any one of SEQ ID NOs: 2, 4, 6, 8 or 10.

2. The method of claim 1, wherein the heterologous nucleic acid further encodes a glutathione-S-transferase polypeptide.

3. The method of claim 1, wherein the gamma-glutamyl peptidase polypeptide is any one of SEQ ID NOs: 2, 4, 6, 8, or 10.

4. The method of claim 1, wherein the amino acid GSL-precursor is a chain elongated amino acid GSL-precursor.

5. The method of claim 4, wherein the amino acid GSL-precursor is an n-homo methionine.

6. The method of claim 4, wherein the GSL is a valine- or isoleucine-derived glucosinolate.

7. The method of claim 1, wherein the nucleic acid further encodes one or more additional polypeptides that cause modification of the core-glucosinolate structure of the GSL biosynthesized in the host.

8. The method of claim 7, wherein the additional polypeptide is a flavin-containing monooxygenase (FMO) that oxidizes methyl-thio-alkyl glucosinolates to methyl-sulfinyl-alkyl glucosinolates.

9. The method of claim 7, wherein the nucleic acid comprises a gene selected from the group consisting of AOP2 and AOP3.

10. The method of claim 1, wherein the nucleic acid further encodes a polypeptide that causes hydrolysis or other degradation of the GSL biosynthesized in the host.

11. The method of claim 1, further comprising converting the host from a phenotype whereby the host is unable to carry out chain elongation of an amino acid that is a GSL precursor to a phenotype whereby the host is able carry out the chain elongation [by expressing a heterologous nucleic acid within the host or one or more cells thereof, following an earlier step of introducing the nucleic acid into the host or an ancestor of either, wherein the heterologous nucleic acid comprises a plurality of nucleotide sequences each of which encodes a polypeptide which, in combination, have GSL biosynthesis activity and amino acid chain elongation activity].

12. The method of claim 1, wherein the heterologous nucleic acid further encodes one or more of the following polypeptides: an ATP sulfurylase, an adenosine 5' phosphosulfate kinase, an adenosine 3',5'-bisphosphate bisphosphatase, an adenosine 3' phosphate 5'-phosphosulfate/adenosine 3',5'-bisphosphate antiporter, and/or an NADPH cytochrome P450 reductase.

13. The method of claim 8, wherein the FMO is encoded by a nucleotide sequence selected from the group consisting of SEQ ID NO: 94, SEQ ID NO: 95, SEQ ID NO: 96 and SEQ ID NO: 97.

14. The method of claim 11, wherein the chain elongated amino acid is an n-homo-methionine or homo-phenylalanine, and wherein the heterologous nucleic acid further encodes the following polypeptides: a transamination enzyme; a condensation enzyme; one or more aconitases; an isopropylmalate dehydrogenase; a methylthioalkyl alfa-ketoacid chloroplastidic transporter.

15. The method of claim 14 wherein the plurality of nucleotide sequences each of which encodes the polypeptide which, in combination, have amino acid chain elongation activity, comprises two or more different nucleic acid molecules.

16. The method of claim 15 wherein one or more of the polypeptides which, in combination, have amino acid chain elongation activity, is BCAT4, MAM1, AC1, AC2, IPMDH or MAC-T polypeptide.

17. The method of claim 14 wherein the condensation enzyme is a MAM3 enzyme.

18. A method of converting a plant or microbial host from a phenotype whereby the host is unable to carry out glucosinolate (GSL) biosynthesis from an amino acid GSL-precursor to any GSL which is a benzylglucosinolate or an indole-3-yl-methyl glucosinolate, to a phenotype whereby the host carries out the GSL biosynthesis of at least one of said GSLs, the method comprising expressing a heterologous nucleic acid within the host or one or more cells thereof, following an earlier step of introducing the nucleic acid into the host or an ancestor of either, wherein the heterologous nucleic acid comprises a plurality of nucleotide sequences each of which encodes a polypeptide which in combination have the GSL biosynthesis activity, and wherein the heterologous nucleic acid encodes all of the following polypeptides:
a CYP83B1;
one of a CYP79A2, a CYP79A1, a CYP79B2, or a CYP79B3;
a sulfotransferase;
a UDP-glucosyl transferase;
a C—S lyase; and
a gamma-glutamyl peptidase polypeptide, wherein the gamma-glutamyl peptidase polypeptide is anyone of SEQ ID NOs: 2, 4, 6, 8 or 10 or a gamma-glutamyl peptidase polypeptide sharing at least 95% identity with anyone of SEQ ID NOs: 2, 4, 6, 8 or 10.

* * * * *

SEQUENCE LISTING

<160> NUMBER OF SEQ ID NOS: 97

<210> SEQ ID NO 1
<211> LENGTH: 753
<212> TYPE: DNA
<213> ORGANISM: Arabidopsis thaliana

<400> SEQUENCE: 1
atggtggagc aaaagagata cgctctgttt ctagcgactt tggactcaga gttcgtgaag    60
aaaacttacg gaggatacca caacgtgttc gtgacgacgt tcggagacga aggagagcat    120

```
tgggactcct ttagagtcgt cagcggagag tttcctgacg agaaagatct ggagaaatac      180
gatggcttcg ttatcagcgg aagctctcac gatgcctttg agaatgatga ttggatcctt      240
aagctctgtg atattgtcaa gaaaattgat gagatgaaga gaaaattct tggcatctgc       300 tttggtcatc agatcatagc cagggtaagg ggaggaacag tcggaagagc aaagaaggga      360
ccagaactta aacttggaga cataaccatc gtcaaggatg cgattacgcc tggaagttac      420
ttcggaaacg agattcctga tagcatagcg atcatcaaat gtcaccagga cgaagtgttg      480
gtgctgcccg aaactgctaa agtgcttgcg tattccaaga actacgaggt ggagatgtat      540
tcgattgagg atcatttgtt ctgtatccaa ggacatcctg agtataacaa agagattctc      600
ttcgagattg ttgatcgtgt tcttgctcta ggctacgtca agcaagaatt tgctgatgcg      660
gctaaggcaa cgatggagaa tagggggagca gacaggaagc tttgggagac gatttgcaag     720
aacttcctca aggcagagt tccaactaac tag                                    753

<210> SEQ ID NO 2
<211> LENGTH: 250
<212> TYPE: PRT
<213> ORGANISM: Arabidopsis thaliana

<400> SEQUENCE: 2

Met Val Glu Gln Lys Arg Tyr Ala Leu Phe Leu Ala Thr Leu Asp Ser
1               5                   10                  15

Glu Phe Val Lys Lys Thr Tyr Gly Gly Tyr His Asn Val Phe Val Thr
                20                  25                  30

Thr Phe Gly Asp Glu Gly Glu His Trp Asp Ser Phe Arg Val Val Ser
            35                  40                  45

Gly Glu Phe Pro Asp Glu Lys Asp Leu Glu Lys Tyr Asp Gly Phe Val
        50                  55                  60

Ile Ser Gly Ser His Asp Ala Phe Glu Asn Asp Trp Ile Leu
65                  70                  75                  80

Lys Leu Cys Asp Ile Val Lys Lys Ile Asp Glu Met Lys Lys Lys Ile
                85                  90                  95

Leu Gly Ile Cys Phe Gly His Gln Ile Ile Ala Arg Val Arg Gly Gly
            100                 105                 110

Thr Val Gly Arg Ala Lys Lys Gly Pro Glu Leu Lys Leu Gly Asp Ile
        115                 120                 125

Thr Ile Val Lys Asp Ala Ile Thr Pro Gly Ser Tyr Phe Gly Asn Glu
    130                 135                 140

Ile Pro Asp Ser Ile Ala Ile Ile Lys Cys His Gln Asp Glu Val Leu
145                 150                 155                 160

Val Leu Pro Glu Thr Ala Lys Val Leu Ala Tyr Ser Lys Asn Tyr Glu
                165                 170                 175

Val Glu Met Tyr Ser Ile Glu Asp His Leu Phe Cys Ile Gln Gly His
            180                 185                 190

Pro Glu Tyr Asn Lys Glu Ile Leu Phe Glu Ile Val Asp Arg Val Leu
        195                 200                 205

Ala Leu Gly Tyr Val Lys Gln Glu Phe Ala Asp Ala Ala Lys Ala Thr
    210                 215                 220

Met Glu Asn Arg Gly Ala Asp Arg Lys Leu Trp Glu Thr Ile Cys Lys
225                 230                 235                 240

Asn Phe Leu Lys Gly Arg Val Pro Thr Asn
                245                 250
```

<210> SEQ ID NO 3
<211> LENGTH: 750
<212> TYPE: DNA
<213> ORGANISM: Arabidopsis thaliana

<400> SEQUENCE: 3

```
atggtggtta ttgagcagaa gaagaggttt gctttgtttt tagcgacgtg tgattcagag      60
ttcgtgaaga agacttacgg tggttacttc aatgtcttcg tttcaacttt cggcgaagaa     120
ggtgagcaat gggatctatt ccgagtcatc gacggacaat tcccgacga gaatgattta     180
gacaagtacg acggtttcgt tatcagtggt agtccacatg atgctttcgg agacgccgat     240
tggattgtta agctttgcga agtttgtcag aaacttgatc acatgaagaa gaaagttctc     300
ggcatctgct tcggccacca gataattact agagttaaag gtgggaagat aggaagagca     360
ctcaaaggtg cagatatggg acttagaagc ataaccatag cgaaagacaa tgaaaaacta     420
cgaggttact ttggagacgt tgaggtccca gcatctttag ctattataaa atgtcatcag     480
gatgaagtgt tggaacttcc tgagtctgct acactacttg cttcttctga ggtatgtaac     540
gtcgagatgt tctctattgg agatcatttt ttctgtattc aagggcatcc agagtataac     600
aaagagattc tgtttgagat tgtggaccga gtccttaata tgaagctgat ggagcaagag     660
tttgcggata aggcaaagag tacgatggag actgcgcaac cagacaggat tctatggcag     720
aagctctgca aaaacttcct gaaaggttga                                       750
```

<210> SEQ ID NO 4
<211> LENGTH: 249
<212> TYPE: PRT
<213> ORGANISM: Arabidopsis thaliana

<400> SEQUENCE: 4

```
Met Val Val Ile Glu Gln Lys Lys Arg Phe Ala Leu Phe Leu Ala Thr
1               5                   10                  15

Cys Asp Ser Glu Phe Val Lys Lys Thr Tyr Gly Gly Tyr Phe Asn Val
            20                  25                  30

Phe Val Ser Thr Phe Gly Glu Glu Gly Glu Gln Trp Asp Leu Phe Arg
        35                  40                  45

Val Ile Asp Gly Gln Phe Pro Asp Glu Asn Asp Leu Asp Lys Tyr Asp
    50                  55                  60

Gly Phe Val Ile Ser Gly Ser Pro His Asp Ala Phe Gly Asp Ala Asp
65                  70                  75                  80

Trp Ile Val Lys Leu Cys Glu Val Cys Gln Lys Leu Asp His Met Lys
                85                  90                  95

Lys Lys Val Leu Gly Ile Cys Phe Gly His Gln Ile Ile Thr Arg Val
            100                 105                 110

Lys Gly Gly Lys Ile Gly Arg Ala Leu Lys Gly Ala Asp Met Gly Leu
        115                 120                 125

Arg Ser Ile Thr Ile Ala Lys Asp Asn Glu Lys Leu Arg Gly Tyr Phe
    130                 135                 140

Gly Asp Val Glu Val Pro Ala Ser Leu Ala Ile Ile Lys Cys His Gln
145                 150                 155                 160

Asp Glu Val Leu Glu Leu Pro Glu Ser Ala Thr Leu Leu Ala Ser Ser
                165                 170                 175

Glu Val Cys Asn Val Glu Met Phe Ser Ile Gly Asp His Phe Phe Cys
            180                 185                 190

Ile Gln Gly His Pro Glu Tyr Asn Lys Glu Ile Leu Phe Glu Ile Val
```

Asp Arg Val Leu Asn Met Lys Leu Met Glu Gln Glu Phe Ala Asp Lys
    210                 215                 220

Ala Lys Ser Thr Met Glu Thr Ala Gln Pro Asp Arg Ile Leu Trp Gln
225                 230                 235                 240

Lys Leu Cys Lys Asn Phe Leu Lys Gly
                245

<210> SEQ ID NO 5
<211> LENGTH: 756
<212> TYPE: DNA
<213> ORGANISM: Arabidopsis thaliana

<400> SEQUENCE: 5
atggctgaac aaaagaagta cctattgttt ctagcgacac cggactcgga gtttgcgaag      60
aagacatatg gaggatacca taatgtgttt gtttcactgc ttggcgatga aggagagcaa     120
tgggactctt ttagagtcgt ggacggcgag tttccagaag agaaggatct tgagaaatac     180
gaaggatttg taatcagtgg tagctctcat gatgcctttc aagacactga ttggatctta     240
aagctctgtg atatcatcaa gaaactcgat gacatgaaca agaaagtcct cggtatttgc     300
tttggccacc agctaatagc tagagcgaag ggaggcaaag tagcgagagc aaggaaagga     360
ccagagcttt gccttggaaa cataaccatc gtgaaagagg cagtgatgcc ggaaaattac     420
ttcggcgaag aagttccagc gaatctgagg atcataaaat gtcatcagga tgaagttttg     480
gagcttccgg aaaatgcaaa actgttagca tattcaagca tgtacgaggt agagatgtat     540
tcaatcaaag ataacttcct tgcattcag ggacatcctg agtataaccg tgacatcttg     600
ttcgatatca ttgatcgtgt tcttgccgga ggccacatta gcaaaacctt gccgaaacg     660
tcaaaggcaa caatggaaaa gaatgaagca gacaggaagt tttggcagaa aatttgcaaa     720
aacttcctca acgtcaacc ctccttatta gtttga                               756

<210> SEQ ID NO 6
<211> LENGTH: 251
<212> TYPE: PRT
<213> ORGANISM: Arabidopsis thaliana

<400> SEQUENCE: 6

Met Ala Glu Gln Lys Lys Tyr Leu Leu Phe Leu Ala Thr Pro Asp Ser
1               5                   10                  15

Glu Phe Ala Lys Lys Thr Tyr Gly Gly Tyr His Asn Val Phe Val Ser
            20                  25                  30

Leu Leu Gly Asp Glu Gly Glu Gln Trp Asp Ser Phe Arg Val Val Asp
        35                  40                  45

Gly Glu Phe Pro Glu Glu Lys Asp Leu Glu Lys Tyr Glu Gly Phe Val
    50                  55                  60

Ile Ser Gly Ser His Asp Ala Phe Gln Asp Thr Asp Trp Ile Leu
65                  70                  75                  80

Lys Leu Cys Asp Ile Ile Lys Lys Leu Asp Asp Met Asn Lys Lys Val
                85                  90                  95

Leu Gly Ile Cys Phe Gly His Gln Leu Ile Ala Arg Ala Lys Gly Gly
            100                 105                 110

Lys Val Ala Arg Ala Arg Lys Gly Pro Glu Leu Cys Leu Gly Asn Ile
        115                 120                 125

Thr Ile Val Lys Glu Ala Val Met Pro Glu Asn Tyr Phe Gly Glu Glu
    130                 135                 140

Val Pro Ala Asn Leu Arg Ile Ile Lys Cys His Gln Asp Glu Val Leu
145                 150                 155                 160

Glu Leu Pro Glu Asn Ala Lys Leu Leu Ala Tyr Ser Ser Met Tyr Glu
                165                 170                 175

Val Glu Met Tyr Ser Ile Lys Asp Asn Phe Leu Cys Ile Gln Gly His
            180                 185                 190

Pro Glu Tyr Asn Arg Asp Ile Leu Phe Asp Ile Ile Asp Arg Val Leu
        195                 200                 205

Ala Gly Gly His Ile Lys Gln Asn Phe Ala Glu Thr Ser Lys Ala Thr
    210                 215                 220

Met Glu Lys Asn Glu Ala Asp Arg Lys Phe Trp Gln Lys Ile Cys Lys
225                 230                 235                 240

Asn Phe Leu Lys Arg Gln Pro Ser Leu Leu Val
                245                 250

<210> SEQ ID NO 7
<211> LENGTH: 756
<212> TYPE: DNA
<213> ORGANISM: Arabidopsis thaliana

<400> SEQUENCE: 7
atggttaatg agcaaaagag atttgctttg tttcttgcta cgagcgattc aacgttcgtg      60
aagaaagcgt atggaggcta tttcaacgtg tttgtttcga cttttggtga agatggtgag     120
caatgggatc tgtttcgagt gatcgacggc gagtttcctg acgataagga tctggataag     180
tacgatggtt ttgttattag tggaagcctt aacgatgctt ttggtgatga tgattggatc     240
gttaagcttt gttctctttg ccaaaagctt gacgacatga agaagaaggt tcttggtatc     300
tgctttggcc accagatact aagtagaatc aaaggaggga agtcggaag gcgagtaga      360
ggtttggata tgggactaag aagcataaca atggttacag acgcggtgaa gccaggtggt     420
tactttggaa gccagattcc gaaatcacta gccattataa aatgccatca agatgaagtt     480
cttgaactcc ctgaatcagc cacattgctt gcttattcag acaaatacaa cgttgagatg     540
tgttcgtatg gaaaccactt gctaggcatc caaggccatc ctgagtacaa caaagagatt     600
cttttcgaga tcattgatcg tgtcgtcaat ttgaagttga tggagcaaga ttttgcggat     660
aaggcgaagg caacgatgga aaacgcggaa ccagatcgga gcaatggca gactctctgc     720
aaaaactttc tcaaaggaag atccgagcaa gtttaa                              756

<210> SEQ ID NO 8
<211> LENGTH: 251
<212> TYPE: PRT
<213> ORGANISM: Arabidopsis thaliana

<400> SEQUENCE: 8

Met Val Asn Glu Gln Lys Arg Phe Ala Leu Phe Leu Ala Thr Ser Asp
1               5                   10                  15

Ser Thr Phe Val Lys Lys Ala Tyr Gly Gly Tyr Phe Asn Val Phe Val
                20                  25                  30

Ser Thr Phe Gly Glu Asp Gly Glu Gln Trp Asp Leu Phe Arg Val Ile
            35                  40                  45

Asp Gly Glu Phe Pro Asp Asp Lys Asp Leu Asp Lys Tyr Asp Gly Phe
        50                  55                  60

Val Ile Ser Gly Ser Leu Asn Asp Ala Phe Gly Asp Asp Asp Trp Ile
65                  70                  75                  80

```
Val Lys Leu Cys Ser Leu Cys Gln Lys Leu Asp Asp Met Lys Lys Lys
            85                  90                  95

Val Leu Gly Ile Cys Phe Gly His Gln Ile Leu Ser Arg Ile Lys Gly
            100                 105                 110

Gly Lys Val Gly Arg Ala Ser Arg Gly Leu Asp Met Gly Leu Arg Ser
            115                 120                 125

Ile Thr Met Val Thr Asp Ala Val Lys Pro Gly Gly Tyr Phe Gly Ser
            130                 135                 140

Gln Ile Pro Lys Ser Leu Ala Ile Ile Lys Cys His Gln Asp Glu Val
145                 150                 155                 160

Leu Glu Leu Pro Glu Ser Ala Thr Leu Leu Ala Tyr Ser Asp Lys Tyr
            165                 170                 175

Asn Val Glu Met Cys Ser Tyr Gly Asn His Leu Leu Gly Ile Gln Gly
            180                 185                 190

His Pro Glu Tyr Asn Lys Glu Ile Leu Phe Glu Ile Asp Arg Val
            195                 200                 205

Val Asn Leu Lys Leu Met Glu Gln Asp Phe Ala Asp Lys Ala Lys Ala
            210                 215                 220

Thr Met Glu Asn Ala Glu Pro Asp Arg Lys Gln Trp Gln Thr Leu Cys
225                 230                 235                 240

Lys Asn Phe Leu Lys Gly Arg Ser Glu Gln Val
            245                 250

<210> SEQ ID NO 9
<211> LENGTH: 747
<212> TYPE: DNA
<213> ORGANISM: Arabidopsis thaliana

<400> SEQUENCE: 9
atggtgaagc agataagaag atacgctcta tttcaagcca cgccagattc tgagttcgtg      60
aaggagatgt acggaggcta cttcaacgta ttcgtgtcgg ctttcggaga cgaaggagag     120
caatgggatc ttttccgtgt gatcgacggc gagtttcctc gcgacgaaga tcttgagaag     180
tatgagggat tcgtcattag tgggagttta catgacgctt tcacagaaga ggattggatc     240
attgagcttt gctctgtttg caaaaaactt gatgtgatga agaagaaaat tcttggcata     300
tgctttggtc accagatcat atgtagagta agaggtggga agtgggaag ggctcgtaaa      360 ggaccagaca taggcctcgg taacataacg atcgttcaag atgtgatcaa accgggtgat     420
tacttcgatc aaatcgagtc attgtcgatc atacaatgtc atcgagacga agtacttgag     480
cctccagagt cggctagagt cataggattc tcagacaaat gcgacgttga gatattctca     540
gtggaagatc acttgctttg ctttcaaggt catcccgagt ataacaaaga gattctcctt     600
gagatcattg atcgtgtcca caagatcaaa tttgttgagg aggaaatttt ggagaaagca     660
aaggattcga tcaagaagtt tgaaccagac acgcagcgtt tgcacatgct ttgcaagaat     720
tttctgaaag gacgaagaac ccactaa                                          747

<210> SEQ ID NO 10
<211> LENGTH: 248
<212> TYPE: PRT
<213> ORGANISM: Arabidopsis thaliana

<400> SEQUENCE: 10

Met Val Lys Gln Ile Arg Arg Tyr Ala Leu Phe Gln Ala Thr Pro Asp
1               5                   10                  15

Ser Glu Phe Val Lys Glu Met Tyr Gly Gly Tyr Phe Asn Val Phe Val
```

```
            20                  25                  30
Ser Ala Phe Gly Asp Glu Gly Glu Gln Trp Asp Leu Phe Arg Val Ile
            35                  40                  45

Asp Gly Glu Phe Pro Arg Asp Glu Asp Leu Glu Lys Tyr Glu Gly Phe
            50                  55                  60

Val Ile Ser Gly Ser Leu His Asp Ala Phe Thr Glu Glu Asp Trp Ile
 65                  70                  75                  80

Ile Glu Leu Cys Ser Val Cys Lys Lys Leu Asp Val Met Lys Lys Lys
                 85                  90                  95

Ile Leu Gly Ile Cys Phe Gly His Gln Ile Ile Cys Arg Val Arg Gly
            100                 105                 110

Gly Lys Val Gly Arg Ala Arg Lys Gly Pro Asp Ile Gly Leu Gly Asn
            115                 120                 125

Ile Thr Ile Val Gln Asp Val Ile Lys Pro Gly Asp Tyr Phe Asp Gln
            130                 135                 140

Ile Glu Ser Leu Ser Ile Ile Gln Cys His Arg Asp Glu Val Leu Glu
145                 150                 155                 160

Pro Pro Glu Ser Ala Arg Val Ile Gly Phe Ser Asp Lys Cys Asp Val
                165                 170                 175

Glu Ile Phe Ser Val Glu Asp His Leu Leu Cys Phe Gln Gly His Pro
            180                 185                 190

Glu Tyr Asn Lys Glu Ile Leu Leu Glu Ile Ile Asp Arg Val His Lys
            195                 200                 205

Ile Lys Phe Val Glu Glu Ile Leu Glu Lys Ala Lys Asp Ser Ile
            210                 215                 220

Lys Lys Phe Glu Pro Asp Thr Gln Arg Leu His Met Leu Cys Lys Asn
225                 230                 235                 240

Phe Leu Lys Gly Arg Arg Thr His
                245

<210> SEQ ID NO 11
<211> LENGTH: 1044
<212> TYPE: DNA
<213> ORGANISM: Brassica carinata

<400> SEQUENCE: 11
attgcacctc tctctttatt ctctctctgc taatcaacca ctctctctat ttacgttagc    60
cggtaaaaaa atggttgagc agaaaaagtt cgctctgttt ctagcgactc ctgattcaga   120
gttcgtgaag aaagagtacg aggatacca caacgtgttc gtgtccacgt tcggtgacga   180
aggagagcat tgggactcgt ttagagtcgt tgaaggcgag tttcccgacg agaaagatct   240
tgacaagtac gacggtttcg ttattagtgg aagctctcac gattccttcg agaatgatcc   300
ttggatcctt aggctatgtg agatcgtcaa gatactcgat gagaagaaga gaaaattct   360 tggcatatgc tttggtcacc agatcatagc cagagtaaga ggaggaacag tgggaagagc   420
aaggaaggga ccagaactta agcttacaga cataaccatc gtgaaggatg cgattaaacc   480
aggaagtttc ttcggaaacg agattccgga tagcatagcc atcctaaagt tacatcagga   540
cgaagtgtta gtgttgcctg aatctgctaa agtactagct tattcagaaa agtacgaggt   600
ggagatgttc tccattgagg atcatttatt ctgtattcaa ggacatcccg agtataacag   660
agagattctc cacgagatcg ttgatcgtgt tcttcgtctt ggcttcatca aggaagattt   720
tgcggatgcg gcaaaagcct cgatgggaa taggggagca gacaggaaac ttttggagac   780
gatttgcaag aatttttctca aaggcagagt tccagctaat taattagttt cactcccaaa   840
```

```
ttatctattt ggctcttgtt atattggagc tagcacttat ggatttatta tcttgctgta        900
ttgtattcaa tatataacct attaatctca tccttgtcaa ggaaacaaaa actcatatta        960
atctcaatgt catatttatg tgttgttacc cataagtaaa attattcaat aaaaactata       1020
gttttgcaaa aaaaaaaaaa aaaa                                              1044
```

```
<210> SEQ ID NO 12
<211> LENGTH: 250
<212> TYPE: PRT
<213> ORGANISM: Brassica carinata

<400> SEQUENCE: 12
```

```
Met Val Glu Gln Lys Lys Phe Ala Leu Phe Leu Ala Thr Pro Asp Ser
1               5                   10                  15

Glu Phe Val Lys Lys Glu Tyr Gly Gly Tyr His Asn Val Phe Val Ser
            20                  25                  30

Thr Phe Gly Asp Glu Gly Glu His Trp Asp Ser Phe Arg Val Val Glu
        35                  40                  45

Gly Glu Phe Pro Asp Glu Lys Asp Leu Asp Lys Tyr Asp Gly Phe Val
    50                  55                  60

Ile Ser Gly Ser Ser His Asp Ser Phe Glu Asn Asp Pro Trp Ile Leu
65                  70                  75                  80

Arg Leu Cys Glu Ile Val Lys Ile Leu Asp Glu Lys Lys Lys Lys Ile
                85                  90                  95

Leu Gly Ile Cys Phe Gly His Gln Ile Ile Ala Arg Val Arg Gly Gly
            100                 105                 110

Thr Val Gly Arg Ala Arg Lys Gly Pro Glu Leu Lys Leu Thr Asp Ile
        115                 120                 125

Thr Ile Val Lys Asp Ala Ile Lys Pro Gly Ser Phe Phe Gly Asn Glu
    130                 135                 140

Ile Pro Asp Ser Ile Ala Ile Leu Lys Leu His Gln Asp Glu Val Leu
145                 150                 155                 160

Val Leu Pro Glu Ser Ala Lys Val Leu Ala Tyr Ser Glu Lys Tyr Glu
                165                 170                 175

Val Glu Met Phe Ser Ile Glu Asp His Leu Phe Cys Ile Gln Gly His
            180                 185                 190

Pro Glu Tyr Asn Arg Glu Ile Leu His Glu Ile Val Asp Arg Val Leu
        195                 200                 205

Arg Leu Gly Phe Ile Lys Glu Asp Phe Ala Asp Ala Ala Lys Ala Ser
    210                 215                 220

Met Glu Asn Arg Gly Ala Asp Arg Lys Leu Leu Glu Thr Ile Cys Lys
225                 230                 235                 240

Asn Phe Leu Lys Gly Arg Val Pro Ala Asn
                245                 250
```

```
<210> SEQ ID NO 13
<211> LENGTH: 771
<212> TYPE: DNA
<213> ORGANISM: Arabidopsis thaliana

<400> SEQUENCE: 13
atggcgtatt ctcttcctac atttccccaa gccttacctt gctcgtcaac caaaacttct         60
tcctccttgg ctaccttccg atctcctttc ttaagattca atggttccac ttccttaatc        120
ccctcctcta tctccatcac ttcacgtggc acatcctccc cgaccatcat cccacgtgct        180
```

```
gccgcctcag aatccgactc taacgaagcc ctagccaaca caaccttcca cggcctctgc    240
tatgtcttga agacaacat agacaccgac cagatcatcc cagcaggagc cgcttgcacc     300
ttcccatcga accagcaaga gcgtgatgag atcgccgctc acgctctctc tggtctacca    360
gacttccaca aaacacggtt cattgagcca ggagagaaca gatcaaagta ctcaatcata    420
atcggcggcg aaaactttgg ttgcggatcg tcacgtgaac atgctccggt ctgtcttgga    480
gcagctggag ctaaagccat agttgctgag tcttacgcaa gaatcttttt ccgtaactcg    540
gttgctacag gagaggtgtt tccgctcgag tcagaggtta gagtctgtga ggagtgtaag    600
acaggagata cggtgacgat cgagctgagt gatagtggtg gtttattgac taatcacacg    660
accggtaaaa actataagct gaagtcgatc ggtgatgctg gaccggttat tgatgctggt    720
ggtatttttg cttatgcgag gatgatggga atgattccat cattagctta a             771
```

```
<210> SEQ ID NO 14
<211> LENGTH: 256
<212> TYPE: PRT
<213> ORGANISM: Arabidopsis thaliana

<400> SEQUENCE: 14

Met Ala Tyr Ser Leu Pro Thr Phe Pro Gln Ala Leu Pro Cys Ser Ser
1               5                   10                  15

Thr Lys Thr Ser Ser Ser Leu Ala Thr Phe Arg Ser Pro Phe Leu Arg
            20                  25                  30

Phe Asn Gly Ser Thr Ser Leu Ile Pro Ser Ser Ile Ser Ile Thr Ser
        35                  40                  45

Arg Gly Thr Ser Ser Pro Thr Ile Ile Pro Arg Ala Ala Ala Ser Glu
    50                  55                  60

Ser Asp Ser Asn Glu Ala Leu Ala Asn Thr Thr Phe His Gly Leu Cys
65                  70                  75                  80

Tyr Val Leu Lys Asp Asn Ile Asp Thr Asp Gln Ile Ile Pro Ala Gly
                85                  90                  95

Ala Ala Cys Thr Phe Pro Ser Asn Gln Gln Glu Arg Asp Glu Ile Ala
            100                 105                 110

Ala His Ala Leu Ser Gly Leu Pro Asp Phe His Lys Thr Arg Phe Ile
        115                 120                 125

Glu Pro Gly Glu Asn Arg Ser Lys Tyr Ser Ile Ile Ile Gly Gly Glu
    130                 135                 140

Asn Phe Gly Cys Gly Ser Ser Arg Glu His Ala Pro Val Cys Leu Gly
145                 150                 155                 160

Ala Ala Gly Ala Lys Ala Ile Val Ala Glu Ser Tyr Ala Arg Ile Phe
                165                 170                 175

Phe Arg Asn Ser Val Ala Thr Gly Glu Val Phe Pro Leu Glu Ser Glu
            180                 185                 190

Val Arg Val Cys Glu Glu Cys Lys Thr Gly Asp Thr Val Thr Ile Glu
        195                 200                 205

Leu Ser Asp Ser Gly Gly Leu Leu Thr Asn His Thr Thr Gly Lys Asn
    210                 215                 220

Tyr Lys Leu Lys Ser Ile Gly Asp Ala Gly Pro Val Ile Asp Ala Gly
225                 230                 235                 240

Gly Ile Phe Ala Tyr Ala Arg Met Met Gly Met Ile Pro Ser Leu Ala
                245                 250                 255

<210> SEQ ID NO 15
<211> LENGTH: 762
```

<212> TYPE: DNA
<213> ORGANISM: Arabidopsis thaliana

<400> SEQUENCE: 15

```
atggcgactt ctcagcaatt tttaaaccct acactcttca aatccttagc ttcctcaaac      60
aaaaactcat gtactctctg cccatctcct tcttgcaac tcaagtccgc ctccacaatt     120
ttcaattaca aaccacttac ttcctcctcc gccacgatca tcacacgcgt cgctgcatca     180
tcctccgatt caggcgagtc aataaccaga gagactttcc acggcctctg cttcgtcttg     240
aaagacaaca tcgacaccga tcaaataatc cccgccgagt acggcactct catcccttcg     300
attccagaag atcgcgagaa actcggctct ttcgcgctta cggcttacc aaaattctac      360
aacgaacgtt tcgttgttcc aggagagatg aaatcaaagt actcagtcat catcggcggc     420
gataatttcg gttgcggatc ttcccgcgaa cacgctccag tttgtctcgg cgcggcggga     480
gctaaagctg tggtggcgga atcgtacgct aggatctttt tcaggaactg tgtagctaca     540
ggtgagattt tcccgttgga atcggaggtt aggatttgcg acgagtgcaa aacaggggat     600
gtggtgacaa tcgaacacaa ggaagacggt agtagtttgc tgatcaatca tacgacgagg     660
aaagaataca aactgaaacc gctcggtgat gccggtccgg tgatcgacgc cggtggaatc     720
ttcgcttatg caagaaaagc cggcatgatt ccttctgctt ga                        762
```

<210> SEQ ID NO 16
<211> LENGTH: 253
<212> TYPE: PRT
<213> ORGANISM: Arabidopsis thaliana

<400> SEQUENCE: 16

```
Met Ala Thr Ser Gln Gln Phe Leu Asn Pro Thr Leu Phe Lys Ser Leu
1               5                   10                  15

Ala Ser Ser Asn Lys Asn Ser Cys Thr Leu Cys Pro Ser Pro Phe Leu
                20                  25                  30

Gln Leu Lys Ser Ala Ser Thr Ile Phe Asn Tyr Lys Pro Leu Thr Ser
            35                  40                  45

Ser Ser Ala Thr Ile Ile Thr Arg Val Ala Ser Ser Ser Asp Ser
    50                  55                  60

Gly Glu Ser Ile Thr Arg Glu Thr Phe His Gly Leu Cys Phe Val Leu
65                  70                  75                  80

Lys Asp Asn Ile Asp Thr Asp Gln Ile Ile Pro Ala Glu Tyr Gly Thr
                85                  90                  95

Leu Ile Pro Ser Ile Pro Glu Asp Arg Glu Lys Leu Gly Ser Phe Ala
            100                 105                 110

Leu Asn Gly Leu Pro Lys Phe Tyr Asn Glu Arg Phe Val Val Pro Gly
        115                 120                 125

Glu Met Lys Ser Lys Tyr Ser Val Ile Ile Gly Gly Asp Asn Phe Gly
    130                 135                 140

Cys Gly Ser Ser Arg Glu His Ala Pro Val Cys Leu Gly Ala Ala Gly
145                 150                 155                 160

Ala Lys Ala Val Val Ala Glu Ser Tyr Ala Arg Ile Phe Phe Arg Asn
                165                 170                 175

Cys Val Ala Thr Gly Glu Ile Phe Pro Leu Ser Glu Val Arg Ile
            180                 185                 190

Cys Asp Glu Cys Lys Thr Gly Asp Val Val Thr Ile Glu His Lys Glu
        195                 200                 205

Asp Gly Ser Ser Leu Leu Ile Asn His Thr Thr Arg Lys Glu Tyr Lys
```

```
            210                 215                 220
Leu Lys Pro Leu Gly Asp Ala Gly Pro Val Ile Asp Ala Gly Gly Ile
225                 230                 235                 240

Phe Ala Tyr Ala Arg Lys Ala Gly Met Ile Pro Ser Ala
                245                 250
```

<210> SEQ ID NO 17
<211> LENGTH: 1215
<212> TYPE: DNA
<213> ORGANISM: Arabidopsis thaliana

<400> SEQUENCE: 17

```
atggcggcgt ttttgcaaac taacatccgt ctggagatca taccgggaag atacagttct       60
ctcaccgatc ataagtttcg tgcgccgtat cgaattaggt gcgccgccgc ttcaccggtg      120
aaaaaacggt ataacatcac tctgcttccc ggcgatggta tcggtccaga agttatatct      180
gttgctaaga atgtgcttca gaaagctgga tttctccaag gactagagtt tgatttccag      240
gagatgcctt tcggcggagc agctttggat ttggtcggag ttccattgcc ggaggaaact      300
tccactgctg ctaaacagtc tgatgccatt cttcttggag ctatcggagg gtacaaatgg      360
gacaagaatg agaaacatct gagacctgag atgggtctgc ttaacattcg aagagatctc      420
aatgtctttg ctaatttgag acctgctaca gttttaccac agctagttga tgcttccaca      480
ctgaagaaag aagtagcaca aggtgttgat atgatgattg taagggagct cactggaggt      540
atttactttg gagagccaag aggcattacg atcaacgaaa atggcgaaga agtcggtttt      600
aatacagaga tctacgctgc tcacgagatt gacagaattg ctcgtgttgc attcgagact      660
gctaggaaaa ggcgtggcaa gctgtgttct gttgacaaag ccaatgtctt ggatgcatca      720
atattgtgga ggaaaagagt aacagcttta gcctctgaat atccagatgt tgaactatca      780
catatgtatg tcgataatgc tgcgatgcag cttgtccgtg acccgaaaca gtttgacaca      840
atcgtcacca ataacatttt tggtgatata ttgtctgatg aagcttcaat gatcactggt      900
agcattggga tgcttccatc tgcaagtctt ggtgaatcgg gacctggact ctttgaacct      960
atacatggtt cagcaccaga tatagctgga caagacaagg caaacccatt ggccaccatt     1020
ctcagtgcgg cgatgcttct caagtatgga cttggagaag aaaaggctgc aaagatgatt     1080
gaagacgcgg tcgtggatgc tctgaacaaa ggtttcagaa ccggagacat ctactccccc     1140
ggaaataaac tggtgggatg caaggaaatg ggtgaggagg ttctcaaatc agtggactcc     1200
aaagttcctg tttaa                                                     1215
```

<210> SEQ ID NO 18
<211> LENGTH: 404
<212> TYPE: PRT
<213> ORGANISM: Arabidopsis thaliana

<400> SEQUENCE: 18

```
Met Ala Ala Phe Leu Gln Thr Asn Ile Arg Leu Glu Ile Ile Pro Gly
1               5                   10                  15

Arg Tyr Ser Ser Leu Thr Asp His Lys Phe Arg Ala Pro Tyr Arg Ile
                20                  25                  30

Arg Cys Ala Ala Ala Ser Pro Val Lys Lys Arg Tyr Asn Ile Thr Leu
            35                  40                  45

Leu Pro Gly Asp Gly Ile Gly Pro Glu Val Ile Ser Val Ala Lys Asn
        50                  55                  60

Val Leu Gln Lys Ala Gly Phe Leu Gln Gly Leu Glu Phe Asp Phe Gln
```

```
                65                  70                  75                  80
        Glu Met Pro Phe Gly Gly Ala Ala Leu Asp Leu Val Gly Val Pro Leu
                            85                  90                  95

Pro Glu Glu Thr Ser Thr Ala Ala Lys Gln Ser Asp Ala Ile Leu Leu
                        100                 105                 110

Gly Ala Ile Gly Gly Tyr Lys Trp Asp Lys Asn Glu Lys His Leu Arg
                    115                 120                 125

Pro Glu Met Gly Leu Leu Asn Ile Arg Arg Asp Leu Asn Val Phe Ala
                130                 135                 140

Asn Leu Arg Pro Ala Thr Val Leu Pro Gln Leu Val Asp Ala Ser Thr
        145                 150                 155                 160

Leu Lys Lys Glu Val Ala Gln Gly Val Asp Met Met Ile Val Arg Glu
                        165                 170                 175

Leu Thr Gly Gly Ile Tyr Phe Gly Glu Pro Arg Gly Ile Thr Ile Asn
                    180                 185                 190

Glu Asn Gly Glu Glu Val Gly Phe Asn Thr Glu Ile Tyr Ala Ala His
                195                 200                 205

Glu Ile Asp Arg Ile Ala Arg Val Ala Phe Glu Thr Ala Arg Lys Arg
            210                 215                 220

Arg Gly Lys Leu Cys Ser Val Asp Lys Ala Asn Val Leu Asp Ala Ser
        225                 230                 235                 240

Ile Leu Trp Arg Lys Arg Val Thr Ala Leu Ala Ser Glu Tyr Pro Asp
                        245                 250                 255

Val Glu Leu Ser His Met Tyr Val Asp Asn Ala Ala Met Gln Leu Val
                    260                 265                 270

Arg Asp Pro Lys Gln Phe Asp Thr Ile Val Thr Asn Asn Ile Phe Gly
                275                 280                 285

Asp Ile Leu Ser Asp Glu Ala Ser Met Ile Thr Gly Ser Ile Gly Met
            290                 295                 300

Leu Pro Ser Ala Ser Leu Gly Glu Ser Gly Pro Gly Leu Phe Glu Pro
        305                 310                 315                 320

Ile His Gly Ser Ala Pro Asp Ile Ala Gly Gln Asp Lys Ala Asn Pro
                        325                 330                 335

Leu Ala Thr Ile Leu Ser Ala Ala Met Leu Leu Lys Tyr Gly Leu Gly
                    340                 345                 350

Glu Glu Lys Ala Ala Lys Met Ile Glu Asp Ala Val Val Asp Ala Leu
                355                 360                 365

Asn Lys Gly Phe Arg Thr Gly Asp Ile Tyr Ser Pro Gly Asn Lys Leu
            370                 375                 380

Val Gly Cys Lys Glu Met Gly Glu Glu Val Leu Lys Ser Val Asp Ser
        385                 390                 395                 400

Lys Val Pro Val

<210> SEQ ID NO 19
<211> LENGTH: 1224
<212> TYPE: DNA
<213> ORGANISM: Arabidopsis thaliana

<400> SEQUENCE: 19
atgggtgtga tatctccgac tgaaactctg ttcttaaagt ctcaacatcg tcttcttcaa    60
cctcgaaact attcatacgc acttgctttt cacagcactc gacgagttgc gaatttccca   120
cgcaactcat tctcttctct aggatcatgt tctgtagatt ttccactacg aagtaacccg   180
atttcacaaa atagcaagtc aattcatcct tggcggagat atgtatccga atctgactca   240
```

```
aacgagctgt atcataagaa ggtttcttct attatggaaa cattaaagca agcctactct    300
tttattcctc atggaattct gttaagtaca atattagctc ttgtctatcc accttctttc    360
acatggttca agccaaggta ctttgtacct ggcttagggt tcatgatgtt tgctgttggt    420
atcaactcta atgaaagaga ttttcttgaa gcacttaaaa gaccagatgc tattttgcc     480 ggttacatcg gacaatactt gattaaacct ctcttaggtt acattttcgg cgtaattgct    540
gtctctcttt tcaatctacc tacttctata ggtgctggaa tcatgttggt ctcatgtgtt    600
agtggagctc agctatcaaa ttacacaact tcttgaccg atccttcact cgcggcgctt     660
agcatcgtca tgcatctat ctcaacggcc actgcggtcc tcgttacacc tatgctttca     720
ctcttactca ttggtaaaaa gcttcccgtt gatgtgtttg ggatgatctc tagcattctt    780
caagtggtga ttacacctat tgccgcagga ctacttctga accggttgtt tccaaggttg    840
tctaatgcaa tcaaaccatt tcttccggcg ttaacagtta tcgatatgag ttgttgcata    900
ggagcacccc ttgctttgaa tatagattca atcttgtctc cgtttggtgc aaccattttg    960
ttcctcgtca tcacgtttca tctcttggct tttgttgctg gttactttt cactggtttc    1020 ttcttcagca aggcacctga tgtaaaagct ctgcaaagaa caatttccta tgaaacagga    1080
atgcaaagta gtcttctcgc tctggccctc gctacaaagt tctttcaaga tcctctcgtt    1140
ggagtgcctc cagcaatctc cacggttgtt atgtctctaa tgggcgtctc gcttgttacc    1200
atatggaaaa acagaaagga gtag                                           1224

<210> SEQ ID NO 20
<211> LENGTH: 407
<212> TYPE: PRT
<213> ORGANISM: Arabidopsis thaliana

<400> SEQUENCE: 20

Met Gly Val Ile Ser Pro Thr Glu Thr Leu Phe Leu Lys Ser Gln His
1               5                   10                  15

Arg Leu Leu Gln Pro Arg Asn Tyr Ser Tyr Ala Leu Ala Phe His Ser
            20                  25                  30

Thr Arg Arg Val Ala Asn Phe Pro Arg Asn Ser Phe Ser Ser Leu Gly
        35                  40                  45

Ser Cys Ser Val Asp Phe Pro Leu Arg Ser Asn Pro Ile Ser Gln Asn
    50                  55                  60

Ser Lys Ser Ile His Pro Trp Arg Arg Tyr Val Ser Glu Ser Asp Ser
65                  70                  75                  80

Asn Glu Leu Tyr His Lys Lys Val Ser Ser Ile Met Glu Thr Leu Lys
                85                  90                  95

Gln Ala Tyr Ser Phe Ile Pro His Gly Ile Leu Leu Ser Thr Ile Leu
            100                 105                 110

Ala Leu Val Tyr Pro Pro Ser Phe Thr Trp Phe Lys Pro Arg Tyr Phe
        115                 120                 125

Val Pro Gly Leu Gly Phe Met Met Phe Ala Val Gly Ile Asn Ser Asn
    130                 135                 140

Glu Arg Asp Phe Leu Glu Ala Leu Lys Arg Pro Asp Ala Ile Phe Ala
145                 150                 155                 160

Gly Tyr Ile Gly Gln Tyr Leu Ile Lys Pro Leu Leu Gly Tyr Ile Phe
                165                 170                 175

Gly Val Ile Ala Val Ser Leu Phe Asn Leu Pro Thr Ser Ile Gly Ala
            180                 185                 190
```

```
Gly Ile Met Leu Val Ser Cys Val Ser Gly Ala Gln Leu Ser Asn Tyr
            195                 200                 205

Thr Thr Phe Leu Thr Asp Pro Ser Leu Ala Ala Leu Ser Ile Val Met
    210                 215                 220

Thr Ser Ile Ser Thr Ala Thr Ala Val Leu Val Thr Pro Met Leu Ser
225                 230                 235                 240

Leu Leu Leu Ile Gly Lys Lys Leu Pro Val Asp Val Phe Gly Met Ile
                245                 250                 255

Ser Ser Ile Leu Gln Val Val Ile Thr Pro Ile Ala Ala Gly Leu Leu
            260                 265                 270

Leu Asn Arg Leu Phe Pro Arg Leu Ser Asn Ala Ile Lys Pro Phe Leu
    275                 280                 285

Pro Ala Leu Thr Val Ile Asp Met Ser Cys Cys Ile Gly Ala Pro Leu
290                 295                 300

Ala Leu Asn Ile Asp Ser Ile Leu Ser Pro Phe Gly Ala Thr Ile Leu
305                 310                 315                 320

Phe Leu Val Ile Thr Phe His Leu Leu Ala Phe Val Ala Gly Tyr Phe
                325                 330                 335

Phe Thr Gly Phe Phe Phe Ser Lys Ala Pro Asp Val Lys Ala Leu Gln
            340                 345                 350

Arg Thr Ile Ser Tyr Glu Thr Gly Met Gln Ser Ser Leu Leu Ala Leu
    355                 360                 365

Ala Leu Ala Thr Lys Phe Phe Gln Asp Pro Leu Val Gly Val Pro Pro
370                 375                 380

Ala Ile Ser Thr Val Val Met Ser Leu Met Gly Val Ser Leu Val Thr
385                 390                 395                 400

Ile Trp Lys Asn Arg Lys Glu
                405

<210> SEQ ID NO 21
<211> LENGTH: 645
<212> TYPE: DNA
<213> ORGANISM: Arabidopsis thaliana

<400> SEQUENCE: 21
atggtggtca agtatatgg gcagataaaa gcagctaatc cacaaagagt attgctctgc      60
tttttggaaa aagacatcga gtttgaagta attcatgtcg atctcgataa acttgaacag     120
aaaaaaccac aacatcttct tcgtcagccg tttggtcaag ttccagctat tgaagatgga     180
tatctgaagc tttttgaatc gcgagccata gcgaggtact acgcgacaaa gtatgcggac     240
caaggaacgg acctattggg caagactttg gagggacgag ccattgtgga ccagtgggtg     300
gaagttgaga ataactattt ctacgctgtg gctctaccct agttatgaa cgtcgtcttt      360 aagcccaagt ctggtaagcc atgcgacgtc gctttggttg aggagctaaa ggtcaagttc     420
gacaaggtcc tggatgtgta tgagaaccgg ttagctacga accggtactt gggcggtgat     480
gaattcacat tagctgattt gagtcatatg cccggtatga gatatatcat gaatgaaacc     540
agtttgagtg gtttggttac gtctcgagag aatctcaacc ggtggtggaa tgagatttcg     600
gctagaccgg cttggaagaa gctcatggaa ttggctgcct attaa                    645

<210> SEQ ID NO 22
<211> LENGTH: 214
<212> TYPE: PRT
<213> ORGANISM: Arabidopsis thaliana

<400> SEQUENCE: 22
```

-continued

```
Met Val Val Lys Val Tyr Gly Gln Ile Lys Ala Ala Asn Pro Gln Arg
1               5                   10                  15

Val Leu Leu Cys Phe Leu Glu Lys Asp Ile Glu Phe Glu Val Ile His
            20                  25                  30

Val Asp Leu Asp Lys Leu Glu Gln Lys Pro Gln His Leu Leu Arg
        35                  40                  45

Gln Pro Phe Gly Gln Val Pro Ala Ile Glu Asp Gly Tyr Leu Lys Leu
    50                  55                  60

Phe Glu Ser Arg Ala Ile Ala Arg Tyr Tyr Ala Thr Lys Tyr Ala Asp
65                  70                  75                  80

Gln Gly Thr Asp Leu Leu Gly Lys Thr Leu Gly Arg Ala Ile Val
                85                  90                  95

Asp Gln Trp Val Glu Val Glu Asn Asn Tyr Phe Tyr Ala Val Ala Leu
                100                 105                 110

Pro Leu Val Met Asn Val Val Phe Lys Pro Lys Ser Gly Lys Pro Cys
        115                 120                 125

Asp Val Ala Leu Val Glu Glu Leu Lys Val Lys Phe Asp Lys Val Leu
    130                 135                 140

Asp Val Tyr Glu Asn Arg Leu Ala Thr Asn Arg Tyr Leu Gly Gly Asp
145                 150                 155                 160

Glu Phe Thr Leu Ala Asp Leu Ser His Met Pro Gly Met Arg Tyr Ile
                165                 170                 175

Met Asn Glu Thr Ser Leu Ser Gly Leu Val Thr Ser Arg Glu Asn Leu
                180                 185                 190

Asn Arg Trp Trp Asn Glu Ile Ser Ala Arg Pro Ala Trp Lys Lys Leu
            195                 200                 205

Met Glu Leu Ala Ala Tyr
    210
```

<210> SEQ ID NO 23
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 23
ggcttaauga attcatggct ccttctgcgc a                               31

<210> SEQ ID NO 24
<211> LENGTH: 66
<212> TYPE: DNA
<213> ORGANISM: Artificial sequence
<220> FEATURE:
<223> OTHER INFORMATION: Synthetic sequence: Primer

<400> SEQUENCE: 24
acatctccug ccaacttaag caaatcaaaa ttcaaagttt gaccagaacc gccctggcgg    60
tcaatc                                                              66

<210> SEQ ID NO 25
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 25
ggtttaauct cgagctatca gccctggcgg tcaatc                36

<210> SEQ ID NO 26
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 26
actctctcut accttatggc tccttctgcg ca                   32

<210> SEQ ID NO 27
<211> LENGTH: 48
<212> TYPE: DNA
<213> ORGANISM: Artificial sequence
<220> FEATURE:
<223> OTHER INFORMATION: Synthetic sequence: Primer

<400> SEQUENCE: 27
aggagatgug aatctaacc caggacctat ggcttcatcg cttctgac   48

<210> SEQ ID NO 28
<211> LENGTH: 60
<212> TYPE: DNA
<213> ORGANISM: Artificial sequence
<220> FEATURE:
<223> OTHER INFORMATION: Synthetic sequence: Primer

<400> SEQUENCE: 28
accacaaguc aaaagagaac ctctaccttc accagaaccc acattcgatg aaacctgagg   60

<210> SEQ ID NO 29
<211> LENGTH: 41
<212> TYPE: DNA
<213> ORGANISM: Artificial sequence
<220> FEATURE:
<223> OTHER INFORMATION: Synthetic sequence: Primer

<400> SEQUENCE: 29
ggtttaauct cgagctatca cacattcgat gaaacctgag g         41

<210> SEQ ID NO 30
<211> LENGTH: 39
<212> TYPE: DNA
<213> ORGANISM: Artificial sequence
<220> FEATURE:
<223> OTHER INFORMATION: Synthetic sequence: Primer

<400> SEQUENCE: 30
ggcttaaugg atccatggcg tattctcttc ctacatttc            39

<210> SEQ ID NO 31
<211> LENGTH: 74
<212> TYPE: DNA
<213> ORGANISM: Artificial sequence
<220> FEATURE:
<223> OTHER INFORMATION: Synthetic sequence: Primer

<400> SEQUENCE: 31
acatctccug ccaacttaag caaatcaaaa ttcaaagttt gaccagaacc agctaatgat   60
ggaatcattc ccat                                       74

<210> SEQ ID NO 32
<211> LENGTH: 63

```
<212> TYPE: DNA
<213> ORGANISM: Artificial sequence
<220> FEATURE:
<223> OTHER INFORMATION: Synthetic sequence: Primer

<400> SEQUENCE: 32
accacaaguc aaaagagaac ctctaccttc accagaacca gctaatgatg gaatcattcc    60
cat                                                                  63

<210> SEQ ID NO 33
<211> LENGTH: 48
<212> TYPE: DNA
<213> ORGANISM: Artificial sequence
<220> FEATURE:
<223> OTHER INFORMATION: Synthetic sequence: Primer

<400> SEQUENCE: 33
aggagatgug gaatctaacc caggacctat ggcgacttct cagcaatt                 48

<210> SEQ ID NO 34
<211> LENGTH: 58
<212> TYPE: DNA
<213> ORGANISM: Artificial sequence
<220> FEATURE:
<223> OTHER INFORMATION: Synthetic sequence: Primer

<400> SEQUENCE: 34
accacaaguc aaaagagaac ctctaccttc accagaacca gcagaaggaa tcatgccg      58

<210> SEQ ID NO 35
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 35
ggcttaaugg atccatggcg acttctcagc aatt                                34

<210> SEQ ID NO 36
<211> LENGTH: 49
<212> TYPE: DNA
<213> ORGANISM: Artificial sequence
<220> FEATURE:
<223> OTHER INFORMATION: Synthetic sequence: Primer

<400> SEQUENCE: 36
acttgtggug atgtcgaaga aaatccaggc ccaatggcgg cgttttgc                 49

<210> SEQ ID NO 37
<211> LENGTH: 43
<212> TYPE: DNA
<213> ORGANISM: Artificial sequence
<220> FEATURE:
<223> OTHER INFORMATION: Synthetic sequence: Primer

<400> SEQUENCE: 37
ggtttaaucc gcggtcacta aacaggaact ttggagtcca ctg                      43

<210> SEQ ID NO 38
<211> LENGTH: 58
<212> TYPE: DNA
<213> ORGANISM: Artificial sequence
<220> FEATURE:
<223> OTHER INFORMATION: Synthetic sequence: Primer
```

<400> SEQUENCE: 38
acttgtggug atgtcgaaga aaatccaggc ccaatgatgg gtgtgatatc tccgactg      58

<210> SEQ ID NO 39
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 39
ggtttaauct cgagctatca ctcctttctg tttttccata tggt      44

<210> SEQ ID NO 40
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 40
ggcttaaugg atccatggag agagcagcaa ttctcc      36

<210> SEQ ID NO 41
<211> LENGTH: 77
<212> TYPE: DNA
<213> ORGANISM: Artificial sequence
<220> FEATURE:
<223> OTHER INFORMATION: Synthetic sequence: Primer

<400> SEQUENCE: 41
acatctccug ccaacttaag caaatcaaaa ttcaaagttt gaccagaacc actaagattc      60
acagtccatt tcatgtt      77

<210> SEQ ID NO 42
<211> LENGTH: 50
<212> TYPE: DNA
<213> ORGANISM: Artificial sequence
<220> FEATURE:
<223> OTHER INFORMATION: Synthetic sequence: Primer

<400> SEQUENCE: 42
aggagatgug gaatctaacc caggacctat ggagagagca gcaattctcc      50

<210> SEQ ID NO 43
<211> LENGTH: 66
<212> TYPE: DNA
<213> ORGANISM: Artificial sequence
<220> FEATURE:
<223> OTHER INFORMATION: Synthetic sequence: Primer

<400> SEQUENCE: 43
accacaaguc aaaagagaac ctctaccttc accagaacca ctaagattca cagtccattt      60
catgtt      66

<210> SEQ ID NO 44
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 44
agagagaguc tcaaacttct tctttcc      27

```
<210> SEQ ID NO 45
<211> LENGTH: 38
<212> TYPE: DNA
<213> ORGANISM: Artificial sequence
<220> FEATURE:
<223> OTHER INFORMATION: Synthetic sequence: Primer

<400> SEQUENCE: 45
ggcttaauga attcatggct tcctctatgc tctcttcc                              38

<210> SEQ ID NO 46
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 46
ggcttaaugg atccatggaa tcagaaaccc taacc                                 35

<210> SEQ ID NO 47
<211> LENGTH: 71
<212> TYPE: DNA
<213> ORGANISM: Artificial sequence
<220> FEATURE:
<223> OTHER INFORMATION: Synthetic sequence: Primer

<400> SEQUENCE: 47
acatctccug ccaacttaag caaatcaaaa ttcaaagttt gaccagaacc tttaccatgt      60
tcaagcaagc c                                                          71

<210> SEQ ID NO 48
<211> LENGTH: 50
<212> TYPE: DNA
<213> ORGANISM: Artificial sequence
<220> FEATURE:
<223> OTHER INFORMATION: Synthetic sequence: Primer

<400> SEQUENCE: 48
aggagatgug gaatctaacc caggacctat gagtgaagca aagaagggtc                 50

<210> SEQ ID NO 49
<211> LENGTH: 63
<212> TYPE: DNA
<213> ORGANISM: Artificial sequence
<220> FEATURE:
<223> OTHER INFORMATION: Synthetic sequence: Primer

<400> SEQUENCE: 49
accacaaguc aaagagaac ctctaccttc accagaacca gtcaaaagag caacaaactc       60
atc                                                                   63

<210> SEQ ID NO 50
<211> LENGTH: 54
<212> TYPE: DNA
<213> ORGANISM: Artificial sequence
<220> FEATURE:
<223> OTHER INFORMATION: Synthetic sequence: Primer

<400> SEQUENCE: 50
acttgtggug atgtcgaaga aaatccaggc ccaatgagcg aagaacaacc acac            54

<210> SEQ ID NO 51
```

```
<211> LENGTH: 48
<212> TYPE: DNA
<213> ORGANISM: Artificial sequence
<220> FEATURE:
<223> OTHER INFORMATION: Synthetic sequence: Primer

<400> SEQUENCE: 51
ggtttaaucc gcggtcacta catttcgaga ttattatcac tcagtttc            48

<210> SEQ ID NO 52
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 52
ggcttaautc tagaatggtg gagcaaaaga gatacg                         36

<210> SEQ ID NO 53
<211> LENGTH: 63
<212> TYPE: DNA
<213> ORGANISM: Artificial sequence
<220> FEATURE:
<223> OTHER INFORMATION: Synthetic sequence: Primer

<400> SEQUENCE: 53
accacaaguc aaaagagaac ctctaccttc accagaaccg ttagttggaa ctctgccttt    60
gag                                                             63

<210> SEQ ID NO 54
<211> LENGTH: 55
<212> TYPE: DNA
<213> ORGANISM: Artificial sequence
<220> FEATURE:
<223> OTHER INFORMATION: Synthetic sequence: Primer

<400> SEQUENCE: 54
acttgtggug atgtcgaaga aaatccaggc ccaatggtgg tcaaagtata tgggc        55

<210> SEQ ID NO 55
<211> LENGTH: 40
<212> TYPE: DNA
<213> ORGANISM: Artificial sequence
<220> FEATURE:
<223> OTHER INFORMATION: Synthetic sequence: Primer

<400> SEQUENCE: 55
ggtttaaucc gcggtcacta ataggcagcc aattccatga                     40

<210> SEQ ID NO 56
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 56
ggcttaautc tagaatggaa gatatcatca tcggc                          35

<210> SEQ ID NO 57
<211> LENGTH: 66
<212> TYPE: DNA
<213> ORGANISM: Artificial sequence
<220> FEATURE:
<223> OTHER INFORMATION: Synthetic sequence: Primer
```

<400> SEQUENCE: 57
accacaaguc aaaagagaac ctctaccttc accagaacca tacttgttca ctttctctgg    60
aacaag                                                                66

<210> SEQ ID NO 58
<211> LENGTH: 56
<212> TYPE: DNA
<213> ORGANISM: Artificial sequence
<220> FEATURE:
<223> OTHER INFORMATION: Synthetic sequence: Primer

<400> SEQUENCE: 58
acttgtggug atgtcgaaga aaatccaggc ccaatgatga gctttaccac atcatt        56

<210> SEQ ID NO 59
<211> LENGTH: 42
<212> TYPE: DNA
<213> ORGANISM: Artificial sequence
<220> FEATURE:
<223> OTHER INFORMATION: Synthetic sequence: Primer

<400> SEQUENCE: 59
ggtttaaugg atcctcacta aggacggaac tttggataaa gg                        42

<210> SEQ ID NO 60
<211> LENGTH: 37
<212> TYPE: DNA
<213> ORGANISM: Artificial sequence
<220> FEATURE:
<223> OTHER INFORMATION: Synthetic sequence: Primer

<400> SEQUENCE: 60
ggcttaautc tagaatgatg agctttacca catcatt                              37

<210> SEQ ID NO 61
<211> LENGTH: 53
<212> TYPE: DNA
<213> ORGANISM: Artificial sequence
<220> FEATURE:
<223> OTHER INFORMATION: Synthetic sequence: Primer

<400> SEQUENCE: 61
acttgtggug atgtcgaaga aaatccaggc ccaatgctcg cgtttattat agg            53

<210> SEQ ID NO 62
<211> LENGTH: 45
<212> TYPE: DNA
<213> ORGANISM: Artificial sequence
<220> FEATURE:
<223> OTHER INFORMATION: Synthetic sequence: Primer

<400> SEQUENCE: 62
ggtttaaugc atgcactagt ttaggttgga tacacatgtg gagct                     45

<210> SEQ ID NO 63
<211> LENGTH: 60
<212> TYPE: DNA
<213> ORGANISM: Artificial sequence
<220> FEATURE:
<223> OTHER INFORMATION: Synthetic sequence: Primer

<400> SEQUENCE: 63
aggagaugtg gaatctaacc caggacctat ggatctctta ttgattatag ccggtttagt    60

<210> SEQ ID NO 64
<211> LENGTH: 47
<212> TYPE: DNA
<213> ORGANISM: Artificial sequence
<220> FEATURE:
<223> OTHER INFORMATION: Synthetic sequence: Primer

<400> SEQUENCE: 64
ggcttaauga attcactagt atggatctct tattgattat agccggt         47

<210> SEQ ID NO 65
<211> LENGTH: 65
<212> TYPE: DNA
<213> ORGANISM: Artificial sequence
<220> FEATURE:
<223> OTHER INFORMATION: Synthetic sequence: Primer

<400> SEQUENCE: 65
accacaaguc aaaagagaac ctctaccttc accagaaccg atgtgtttcg ttggtgcaag    60
aacga                                                               65

<210> SEQ ID NO 66
<211> LENGTH: 40
<212> TYPE: DNA
<213> ORGANISM: Artificial sequence
<220> FEATURE:
<223> OTHER INFORMATION: Synthetic sequence: Primer

<400> SEQUENCE: 66
ggcttaauga attcactagt atggtggagc aaaagagata                          40

<210> SEQ ID NO 67
<211> LENGTH: 68
<212> TYPE: DNA
<213> ORGANISM: Artificial sequence
<220> FEATURE:
<223> OTHER INFORMATION: Synthetic sequence: Primer

<400> SEQUENCE: 67
atctccugcc aacttaagca aatcaaaatt caaagtttga ccagaaccgt tagttggaac    60
tctgcctt                                                            68

<210> SEQ ID NO 68
<211> LENGTH: 43
<212> TYPE: DNA
<213> ORGANISM: Artificial sequence
<220> FEATURE:
<223> OTHER INFORMATION: Synthetic sequence: Primer

<400> SEQUENCE: 68
ggtttaaucg catgcactag tctagttagt tggaactctg cct                      43

<210> SEQ ID NO 69
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 69
ggcttaauat gagcgaagaa caaccacacg cca                                 33

<210> SEQ ID NO 70
<211> LENGTH: 35

```
<212> TYPE: DNA
<213> ORGANISM: Artificial sequence
<220> FEATURE:
<223> OTHER INFORMATION: Synthetic sequence: Primer

<400> SEQUENCE: 70
ggtttaautt acatttcgag attattatca ctcag                               35

<210> SEQ ID NO 71
<211> LENGTH: 54
<212> TYPE: DNA
<213> ORGANISM: Artificial sequence
<220> FEATURE:
<223> OTHER INFORMATION: Synthetic sequence: Primer

<400> SEQUENCE: 71
atgcgggacg tcgaggagaa tcctggccca atgagcgaag aacaaccaca cgcc          54

<210> SEQ ID NO 72
<211> LENGTH: 55
<212> TYPE: DNA
<213> ORGANISM: Artificial sequence
<220> FEATURE:
<223> OTHER INFORMATION: Synthetic sequence: Primer

<400> SEQUENCE: 72
aataacgagc tcggtacctt acatttcgag attattatca ctcagtttca aagct         55

<210> SEQ ID NO 73
<211> LENGTH: 70
<212> TYPE: DNA
<213> ORGANISM: Artificial sequence
<220> FEATURE:
<223> OTHER INFORMATION: Synthetic sequence: Primer

<400> SEQUENCE: 73
acgtggagcc aacccagggc cttggtctca tcctcaattt gaaaagatgg cggaaacaac    60
tcccaaagtg                                                           70

<210> SEQ ID NO 74
<211> LENGTH: 62
<212> TYPE: DNA
<213> ORGANISM: Artificial sequence
<220> FEATURE:
<223> OTHER INFORMATION: Synthetic sequence: Primer

<400> SEQUENCE: 74
accgcagtta gcagacttcc tctgccctcc ttccctaaac tctctataaa ctcgttaatg    60
ct                                                                   62

<210> SEQ ID NO 75
<211> LENGTH: 68
<212> TYPE: DNA
<213> ORGANISM: Artificial sequence
<220> FEATURE:
<223> OTHER INFORMATION: Synthetic sequence: Primer

<400> SEQUENCE: 75
aataacgaat tcccatggct caccaccacc accaccacat ggaatcaaag acaacccaaa    60
acggatcc                                                             68

<210> SEQ ID NO 76
<211> LENGTH: 76
<212> TYPE: DNA
```

-continued

```
<213> ORGANISM: Artificial sequence
<220> FEATURE:
<223> OTHER INFORMATION: Synthetic sequence: Primer

<400> SEQUENCE: 76
actccacgct cccgccaact tgagaaggtc aaaattcaaa gtctggttat catgttgaag      60
caagccagta tctttg                                                     76

<210> SEQ ID NO 77
<211> LENGTH: 20
<212> TYPE: DNA
<213> ORGANISM: Artificial sequence
<220> FEATURE:
<223> OTHER INFORMATION: Synthetic sequence: Primer

<400> SEQUENCE: 77
aataacgaat tcccatggct                                                 20

<210> SEQ ID NO 78
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 78
aataacgagc tcggtacctt ac                                              22

<210> SEQ ID NO 79
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 79
aataacactc gagatggtgg agcaaaagag atac                                 34

<210> SEQ ID NO 80
<211> LENGTH: 37
<212> TYPE: DNA
<213> ORGANISM: Artificial sequence
<220> FEATURE:
<223> OTHER INFORMATION: Synthetic sequence: Primer

<400> SEQUENCE: 80
aataacagaa ttcctagtta gttggaactc tgcctttt                              37

<210> SEQ ID NO 81
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 81
acaatttccc cactatctat cctc                                            24

<210> SEQ ID NO 82
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 82
```
tttccaatac tttggtgaaa atca                                         24

<210> SEQ ID NO 83
<211> LENGTH: 66
<212> TYPE: DNA
<213> ORGANISM: Artificial sequence
<220> FEATURE:
<223> OTHER INFORMATION: Synthetic sequence: Primer

<400> SEQUENCE: 83
acatctccug ccaacttaag caaatcaaaa ttcaaagttt gaccagaacc gccctggcgg    60
tcaatc                                                              66

<210> SEQ ID NO 84
<211> LENGTH: 50
<212> TYPE: DNA
<213> ORGANISM: Artificial sequence
<220> FEATURE:
<223> OTHER INFORMATION: Synthetic sequence: Primer

<400> SEQUENCE: 84
aggagatgug gaatctaacc caggacctat ggcttcgtta cttctcacat               50

<210> SEQ ID NO 85
<211> LENGTH: 41
<212> TYPE: DNA
<213> ORGANISM: Artificial sequence
<220> FEATURE:
<223> OTHER INFORMATION: Synthetic sequence: Primer

<400> SEQUENCE: 85
ggtttaauct cgagctatca tacaacagcg gaaatctgag g                       41

<210> SEQ ID NO 86
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 86
ggcttaauat gaacactttt acctcaaact cttcg                              35

<210> SEQ ID NO 87
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 87
ggtttaautc acttcaccgt cgggtaga                                      28

<210> SEQ ID NO 88
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 88
ggcttaauat ggatctctta ttgattatag ccggt                              35

<210> SEQ ID NO 89

```
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 89
ggcttaautc agatgtgttt cgttggtgc                                    29

<210> SEQ ID NO 90
<211> LENGTH: 21
<212> TYPE: DNA
<213> ORGANISM: Artificial sequence
<220> FEATURE:
<223> OTHER INFORMATION: Synthetic sequence: Primer

<400> SEQUENCE: 90
atggaatcaa agacaaccca a                                            21

<210> SEQ ID NO 91
<211> LENGTH: 19
<212> TYPE: DNA
<213> ORGANISM: Artificial sequence
<220> FEATURE:
<223> OTHER INFORMATION: Synthetic sequence: Primer

<400> SEQUENCE: 91
gtctcgtacc taaggaaca                                               19

<210> SEQ ID NO 92
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 92
gaaggttagc gaaaggtatc tc                                           22

<210> SEQ ID NO 93
<211> LENGTH: 18
<212> TYPE: DNA
<213> ORGANISM: Artificial sequence
<220> FEATURE:
<223> OTHER INFORMATION: Synthetic sequence: Primer

<400> SEQUENCE: 93
tgtttcttgt ttagggcg                                                18

<210> SEQ ID NO 94
<211> LENGTH: 1576
<212> TYPE: DNA
<213> ORGANISM: Arabidopsis thaliana

<400> SEQUENCE: 94
atcttgccat taaaatatag tatttatatt tggcctgaag ctgatgcaac ttatacacaa    60
aacctactat tattaagatt tgacaaaata tggcaccagc tcaaaaccaa atcacttcta   120
aacacgtggc agtgatcgga gccgaccag ccggtctcat aacgtctagg agctccgtc    180 gtgaaggtca cagtgtagtt gtgtttgaac gggagaaaca agtcggtggt ctatgggttt   240
acacacctaa atccgattcc gatccactta gccttgaccc cacccgatcc aaagtccact   300
cgagcatcta cgagtctctc cgaaccaatg tcccgagaga agtatgggt gtcagggact   360 tcccgttttt gccacgtttc gatgacgagt caagagacgc gagacgttat ccaaatcata   420
```

```
gggaagttct tgcgtatatt caagactttg ctagagagtt taaaatagag gagatgatcc    480
ggttcgagac cgaggtggtt cgcgttgaac cggttgacaa cgggaactgg agggtccagt    540
cgaaaaactc cggcgggttc ttggaagatg agatctatga cgccgtcgtg gtttgcaatg    600
gtcactatac agaaccaaat attgctcata ttcctggtat aaaatcgtgg ccaggaaagc    660
agattcatag ccacaactat agagttcctg atccattcga aaacgaggtg gtggtggtga    720
taggaaattt tgcgagtggt gccgatatta gtagggacat agctaaggtc gcaaaagaag    780
tccacattgc gtctagagca agggaacccc acacatacga aagatttcc gttccccaaa     840
acaatctatg gatgcattcc gaaatcgaca ccacccatga ggatgggtcg attgttttca    900
aaaacgggaa ggtgatattt gctgatagca ttgtgtattg caccgggtac aagtataact    960
tcccatttct tgaaacaaat ggctatttgc gcattgatga aaaacgtgtt gaacctctat    1020
acaagcatgt ctttccacca gcgcttgccc ctggacttgc tttcgttggt ttgccagcaa    1080
tggggatagt atttgttatg tttgaaatcc aaagcaaatg ggtggcagca gtcttgtcag    1140
gacgagttac acttccctca acagataaga tgatggaaga tattaatgcg tggtatgcgt    1200
cgcttgatgc cttaggtatt cccaagagac atactcatac gataggtaga attcagagtg    1260
agtacctcaa ttgggtcgcg aaagaatctg gttgtgaact cgtagaacgt tggagaggtc    1320
aagaagttga cggcggatac ctgagacttg tggcccatcc agaaacttac cgtgatgaat    1380
gggacgacga tgaactcata gaagaagcgt acaatgattt ttctaggaag aagttgatta    1440
gtgttgatcc ttcttattac ctcgaaaatg gaagatgatc tgcgccaata gtgccgactt    1500
gttttctttt tctggtaggt gggttgattc caagccttca ataaattgca aaactattgt    1560
aagctttaca atttac                                                   1576

<210> SEQ ID NO 95
<211> LENGTH: 1591
<212> TYPE: DNA
<213> ORGANISM: Arabidopsis thaliana

<400> SEQUENCE: 95
aaaacatatt gtttcacatt cctaaataaa tgaaaatcaa acatatcata gaaatttaat     60
aaaataaatg gcaccaactc aaaacacaat ctgttcgaaa cacgtggcag tgattggagc    120
cggagctgcc ggtctcgtaa cggctaggga acttcgtcgt gaaggtcaca ctgtcgttgt    180
ctttgaccgg gaaaaacaag tgggaggtct ctggaactac tcatctaaag ctgactctga    240
cccgcttagc ctcgacacaa cccgaaccat agtccacacg agcatctacg agtctctccg    300
aaccaacctc ccgagagaat gtatgggttt tacggacttt cctttcgtgc cacgcattca    360
tgacatctcg agagactcga gacggtatcc gagtcacaga gaagttcttg cgtatcttca    420
agactttgct agagagttta aaatagagga gatggtccgg ttcgagacag aggtggtttg    480
tgttgagccg gttaacggga atggagtgt ccggtccaag aattccgttg gtttcgccgc     540
ccatgaaatc tttgatgccg tcgttgtttg tagtggtcac tttacagaac taacgttgc     600
tcatattcct gggataaaat cgtggccagg aaagcagatc catagccaca actacagagt    660
tcctggtcca ttcaataacg aggtagtggt ggtgatcgga aattatgcga gcggtgctga    720
tattagtagg gatatagcta aggtcgcgaa agaagttcac attgcctcta gagcgagtga    780
atctgatacg taccgaaagc ttccagtgcc caaaacaat ctatgggttc attccgagat     840
agacttcgcc catcaggatg gatccattct tttcaaaaat gggaaggtgg tatatgctga    900
```

| | |
|---|---|
| taccattgtg cattgcactg ggtacaaata ttactttcca tttcttgaaa ccaatggcta | 960 |
| tataaacatt aatgaaaacc gcgtcgaacc tctatacaag catgtctttc tacccgcgct | 1020 |
| agcccccagt ctttctttca tcggtttacc tggaatggcc atacaattcg ttatgtttga | 1080 |
| aattcaaagc aaatgggtgg ctgcagtctt gtccggacga gttatacttc cctcgcaaga | 1140 |
| caagatgatg gaagatatta ttgagtggta tgcaacgctt gatgtgttag gaattcccaa | 1200 |
| aagcatacg cataaattgg gtaaaatttc gtgtgagtac ctcaactgga tcgcggaaga | 1260 |
| atgtcattgt tcgccagttg aaaattggag aattcaagaa gttgagcgtg gattccagag | 1320 |
| aatggtctcc cacccagaaa tttaccgcga tgaatgggat gatgatgatc ttatggaaga | 1380 |
| agcgtacaag gattttgcta ggaagaagtt aattagttct catccttctt atttcctcga | 1440 |
| atcatgatga tgatctgcga caaatattgt ccaaaaatta aaaatcgctt gtttcgttct | 1500 |
| ttcttatagt cttaagtagc agctggactt gttttttaat tttgtttgtg tgttccagta | 1560 |
| acttaaagtt gatactctta tttatgttca t | 1591 |

<210> SEQ ID NO 96
<211> LENGTH: 1779
<212> TYPE: DNA
<213> ORGANISM: Arabidopsis thaliana

<400> SEQUENCE: 96

| | |
|---|---|
| acacaacaat ccttcttaca tttctaccaa caaaacacaa aacacaaaca tagcattcaa | 60 |
| aactttgaaa aatggcacca gctcctagtc caatcaattc tcaacacgtg gcggtgatcg | 120 |
| gagccggagc agccggtttta gtagcagcca gagagcttcg tcgtgaaggt cacaccgtcg | 180 |
| ttgtccttga ccgagagaaa caagtaggtg gtctttgggt ttacacacct gaaaccgagt | 240 |
| ccgacgagct tggtcttgac ccgacccgac ccatagtcca ctcgagcgtc tacaagtctc | 300 |
| tccgaaccaa tctccctaga gaatgtatgg gttacaagga tttcccttc gtgccacgtg | 360 |
| gcgatgatcc gtcaagagac tctagaaggt atccgagtca cagggaagtt cttgcgtacc | 420 |
| ttcaagactt tgctacagag tttaacatag aggagatgat ccggttcgag actgaggttc | 480 |
| ttcgtgttga accggttaat ggtaaatgga ggtccagtc taaaaccggc ggcggttttt | 540 |
| ccaacgatga gatctatgac gccgttgtaa tgtgttgtgg acatttcgca gaaccaaaca | 600 |
| tcgctcaaat tcctggaatt gagtcatggc cggggaggca aacacacagc cacagttatc | 660 |
| gagttcctga tccattcaaa gatgaggtgg tggtagtaat cgggaatttt gcgagtggag | 720 |
| ccgatatcag tagagacata tctaaagtcg caaaagaagt tcatatcgca tctagagcaa | 780 |
| gtaaatccaa cactttcgaa aaacgtcctg tacctaataa caatctctgg atgcactctg | 840 |
| agatagacac cgcccacgag gatggtacca ttgttttaa aaatgggaag gtggtacatg | 900 |
| ctgataccat tgtccattgt accgggtaca agtattactt tccatttctt gagaccaata | 960 |
| attatatgag agttgatgac aatcgcgttg aacctctcta caagcatatt tttccacctg | 1020 |
| cgctagctcc cggactttct ttcattggtt tacctgcaat gggtctacaa ttctatatgt | 1080 |
| ttgaagtcca aagcaaatgg gttgctgcag tcttgtctgg acgagttaca cttccttcgg | 1140 |
| tagatgaaat gatggacgat cttaagttgt cgtatgaaac acaagaagcg ttaggtattc | 1200 |
| ccaaaagata tacacataag ttgggtaaat ctcagtgtga gtacctcgat tggatcgcag | 1260 |
| acctgtgtgg attcccacat gttgaacatt ggagagatca agaagtaact cgcggttacc | 1320 |
| agagacttgg taatcaacca gaaacttccc gtgatgaatg gatgatgat gatctcatgg | 1380 |
| aagaagcata cgaagatttt gctagactaa atctgatcaa ttttcatcct tctcgttttc | 1440 |

-continued

| | |
|---|---|
| tcgaatccgg aagatgaagt ttgactacga ttgtaattgt gtctacttgt ttggatttaa | 1500 |
| agtacattgc attataaaaa taatgtgtga gtaaatagtt tataagagtg tgaaggtctt | 1560 |
| cttggctagg gttacatgtt gttcgatctc cggaattagc ttcatggtgt ctagaaactt | 1620 |
| ttgttttta gaccaatatg ttaagaataa agtatgtag ttaattcccg taagttttta | 1680 |
| tgaatccctg gttcattgtg caaatgtttt ttttttgtt attgttctgt taatatcaaa | 1740 |
| gagtgtcctt aaatgtatgc ataattccct cttttggc | 1779 |

<210> SEQ ID NO 97
<211> LENGTH: 1740
<212> TYPE: DNA
<213> ORGANISM: Arabidopsis thaliana

<400> SEQUENCE: 97

| | |
|---|---|
| taaccaaaac acagagatca tacgacagtc tcctaccaaa taaagaaaaa tccaccatac | 60 |
| cataaagttc aaatatatgg caccagctca aaacccgatc agttctcaac acgtggtagt | 120 |
| catcggagcc ggagcagccg gtctcgtagc ggctagggag ctcagtcgtg aaggtcacac | 180 |
| tgttgtcgta ttagagcggg agaaagaagt aggaggtctc tggatctatt cacccaaagc | 240 |
| cgaatccgac ccgcttagcc ttgacccaac ccgttccata gtccactcga gcgtgtacga | 300 |
| gtctctccga accaacctcc cacgagaatg tatgggtttc acggacttcc cttttgtgcc | 360 |
| tcgtttcgat gacgagtcaa gagactcgag acggtatccg agccacatgg aagttcttgc | 420 |
| gtaccttcaa gactttgcta gagagtttaa cctagaggag atggttcggt tcgagatcga | 480 |
| ggtggttcgg gttaaccgg ttaacgggaa atggagggtc tggtctaaaa cctctggcgg | 540 |
| tgtttcccac gatgagatct ttgacgccgt tgttgtttgc agtggacact atacagaacc | 600 |
| aaacgttgct catattcctg gtataaaatc gtggccagga aagcagatcc atagccacaa | 660 |
| ctacagagtt cctgggccat tcgaaaacga ggtggtggtg gtcatcggaa attttgctag | 720 |
| cggtgccgat attagtaggg acatagctaa ggtcgcgaaa aagttcaca ttgcatctag | 780 |
| agcgagtgaa tttgatacat acgaaaagct tcccgtgcct cggaacaatc tatggattca | 840 |
| ttcggaaata gacacggcat atgaagatgg gtccattgtt ttcaaaaacg ggaaggtggt | 900 |
| atatgctgat agcattgtgt attgcactgg atataaatat cgcttcacat tccttgaaac | 960 |
| caatggctat atgaacattg atgaaaaccg cgtagaacat ctatacaagc atgtatttcc | 1020 |
| acctgcgctt tctcctggtc tttcattcgt tggtttacca tcgatgggca tacaatttgt | 1080 |
| tatgtttgaa atccaaagca aatgggtggc agcagtcttg tcaaggcggg ttacacttcc | 1140 |
| cacagaagat aagatgatgg aagatattag tgcgtggtat gcatcgcttg atgcggtagg | 1200 |
| cattcctaaa agatatacac ataaattggg taaaattcag agtgagtacc tcaattgggt | 1260 |
| cgcagaagaa tgtggttgtc cgctcgttga acattggaga aatcaacaaa tcgtccgcgg | 1320 |
| ataccagaga cttgtctcac acccagaaac ttatcgcgat gaatgggacg acaatgacct | 1380 |
| tatggaagaa gcttacgagg actttgctag gaagaaatta attagtttcc atccttccca | 1440 |
| tatcctctaa tcaagaaaat gattttgtg tttttacttt gggggtgggt gtattgtatt | 1500 |
| taagaagcat aaggaaggat ggattctttc cttttcaggg ttgattgcta aactattgaa | 1560 |
| agctttgaat aaataggagg gtttatctct aaggcatgat gccctgattg ttattttct | 1620 |
| ttgtgtgtgt ttgttttgt ttgcatttga gtttttattt attttgtgct tatgtttgaa | 1680 |
| ttttacactg attatgttca ccacgtatag atgcaaatat tacttccgtt tcttgaaacc | 1740 |